US008563808B2

(12) United States Patent
Carozzi et al.

(10) Patent No.: US 8,563,808 B2
(45) Date of Patent: *Oct. 22, 2013

(54) AXMI-003, A DELTA-ENDOTOXIN GENE AND METHODS FOR ITS USE

(75) Inventors: Nadine Carozzi, Raleigh, NC (US); Tracy Hargiss, Cary, NC (US); Michael G. Koziel, Raleigh, NC (US); Nicholas B. Duck, Apex, NC (US); Brian Carr, Raleigh, NC (US)

(73) Assignee: Athenix Corporation, Morrisville, NC (US)

( * ) Notice: Subject to any disclaimer, the term of this patent is extended or adjusted under 35 U.S.C. 154(b) by 1039 days.

This patent is subject to a terminal disclaimer.

(21) Appl. No.: 11/765,491

(22) Filed: Jun. 20, 2007

(65) Prior Publication Data

US 2007/0240239 A1    Oct. 11, 2007

Related U.S. Application Data

(63) Continuation of application No. 10/926,819, filed on Aug. 26, 2004, now Pat. No. 7,253,343.

(60) Provisional application No. 60/498,518, filed on Aug. 28, 2003.

(51) Int. Cl.
    *A01H 5/00*     (2006.01)
    *A01H 5/10*     (2006.01)
    *C12N 15/82*     (2006.01)
    *C12N 1/21*     (2006.01)
    *C12N 15/32*     (2006.01)

(52) U.S. Cl.
    USPC ................ 800/302; 536/23.71; 435/320.1; 435/252.3; 435/418; 424/93.2; 800/279

(58) Field of Classification Search
    None
    See application file for complete search history.

(56) References Cited

U.S. PATENT DOCUMENTS 5,985,267 A    11/1999    Payne et al.
5,986,177 A    11/1999    Osman et al.
6,232,439 B1    5/2001    Osman et al.

FOREIGN PATENT DOCUMENTS

WO    WO 01/19859    3/2001

OTHER PUBLICATIONS

NCBI Database Report for Accession No. AAA22345, Jul. 27, 1993.
NCBI Database Report for Accession No. AAA82114, Submitted Mar. 10, 1994.
NCBI Database Report for Accession No. AAB00958, May 28, 1996.
NCBI Database Report for Accession No. AAC36999, Submitted Sep. 19, 1994.
NCBI Database Report for Accession No. AAC62933, Submitted Mar. 31, 1998.
NCBI Database Report for Accession No. AAD44366, Submitted Feb. 10, 1998.
NCBI Database Report for Accession No. AAE71691, May 15, 2001.
NCBI Database Report for Accession No. AAK66742, Submitted Apr. 24, 2001.
NCBI Database Report for Accession No. AAM73516, Submitted Jun. 15, 2000.
NCBI Database Report for Accession No. AF047579, Submitted Feb. 10, 1998.
NCBI Database Report for Accession No. AF056933, Submitted Mar. 31, 1998.
NCBI Database Report for Accession No. AF076953, Submitted Jul. 6, 1998.
NCBI Database Report for Accession No. AF211190, Submitted Dec. 3, 1999.
NCBI Database Report for Accession No. AY262167, Submitted Mar. 25, 2003.
NCBI Database Report for Accession No. CAA44633, Submitted Oct. 14, 1991.
NCBI Database Report for Accession No. CAA71024, Submitted Oct. 15, 1996.
NCBI Database Report for Accession No. CAC85964, Submitted Jun. 26, 2001.
NCBI Database Report for Accession No. 087404, Submitted Mar. 1998.
NCBI Database Report for Accession No. Q45709, May 30, 2000.
NCBI Database Report for Accession No. Q45752, May 30, 2000.
NCBI Database Report for Accession No. Q9XDL1, Oct. 16, 2001.
Genseq Online Database Report for Accession No. ADM74716, Jun. 3, 2004, Abstract (XP-002325395).
WPI/Derwent Database Report for Accession No. AN-2003-442339, Aug. 20, 2001 (XP-002325397).
De Maagd, R. A., et al., "How *Bacillus thuringiensis* has Evolved Specific Toxins to Colonize the Insect World," *Trends in Genetics*, Apr. 2001, pp. 193-199, vol. 17, No. 4.
Donovan, W. P., et al., "Characterization of Two Genes Encoding *Bacillus thuringiensis* Insecticidal Crystal Proteins Toxic to *Coleoptera* Species," *Applied and Environmental Microbiology*, Dec. 1992, pp. 3921-3927, vol. 58, No. 12.
Song, F., et al., "Identification of cryII-Type Genes from *Bacillus thuringiensis* Strains and Characterization of a Novel cryII-Type Gene," *Applied and Environmental Microbiology*, Sep. 2003, pp. 5207-5211, vol. 69, No. 9.
Lazar, E., et al., "Transforming Growth Factor α: Mutation of Aspartic Acid 47 and Leucine 48 Results in Different Biological Activities", 1988, Mol. Cell. Biol. 8:1247-1252.

(Continued)

*Primary Examiner* — Anne Kubelik

(57) ABSTRACT

Compositions and methods for conferring pesticidal activity to bacteria, plants, plant cells, tissues and seeds are provided. Compositions comprising a coding sequence for a delta-endotoxin polypeptide are provided. The coding sequences can be used in DNA constructs or expression cassettes for transformation and expression in plants and bacteria. Compositions also comprise transformed bacteria, plants, plant cells, tissues, and seeds. In particular, isolated delta-endotoxin nucleic acid molecules are provided. Additionally, amino acid sequences corresponding to the polynucleotides are encompassed. In particular, the present invention provides for isolated nucleic acid molecules comprising nucleotide sequences encoding the amino acid sequence shown in SEQ ID NO:2 or 4, or the nucleotide sequence set forth in SEQ ID NO:1 or 3, as well as variants thereof.

15 Claims, 6 Drawing Sheets

(56) References Cited

OTHER PUBLICATIONS

Hill, M., et al., "Functional Analysis of Conserved Histidines in ADP-Glucose Pyrophosphorylase from *Escherichia coli*" 1998, Biochem. Biophys. Res. Comm. 244:573-577.

Guo, H., et al., "Protein Tolerance to Random Amino Acid Change", 2004, Proc. Natl. Acad. Sci USA 101:9205-9210.

De Maagd, R., et al., "Identification of *Bacillus thuringiensis* Delta-Endotoxin CryI C Domain III Amino Acid Residues Involved in Insect Specificity", 1999, Appl. Environ. Microbiol. 65:4369-4374.

Tounsi, S. et al., "Cloning and Study of the Expression of a Novel *cryIIa*-Type Gene from *Bacillus thuringiensis* subsp. *kurstaki*" 2003, J. Appl. Microbiol. 95:23-28.

Angsuthanasombat, C., et al., "Directed Mutagenesis of the *Bacillus thuringiensis* CrIy 11A Toxin Reveals a Crucial Role in Larvicidal Activity of Arginine-136 in Helix 4" 2001, J. Biochem. Mol. Biol. 34:402-407.

Shin, B. et al., "Distribution of *cryV*-Type Insecticidal Protein Genes in *Bacillus thuringiensis* and Cloning of *cryV*-Type Genes from *Bacillus thuringiensis* subsp. *korsakov* and *Bacillus thuringiensis* subsp. *etomocidus*", 1995, Appl. Environ. Microbiol. 61:2402-2407.

Porcar et al., 2002, GenBank Accession No. AF278797.

```
AXMI-003  : TDVTDYHIDQVSNLVESLSDEFYLDEKRELFEIVKYVKQLNIERDM : 719
cry1Ae    : TDVTDYHIDQVSNLVECLSDEFCLDEKQELSEKVKHAKRLSDERNL : 682
cry1Ab    : TDVTDYHIDQVSNLVECLSDEFCLDEKKELSEKVKHAKRLSDERNL : 683
cry1Ac    : TNVTDYHIDQVSNLVTYLSDEFCLDEKRELSEKVKHAKRLSDERNL : 684
cry1Ba    : TDVTDYHIDQVSNLVACLSDEFCLDEKRELLEKVKYAKRLSDERNL : 711
cry1Ca    : TDVTDYHIDQVSNLVDCLSDEFCLDEKRELSEKVKHAKRLSDERNL : 691
cry1Fa    : TDVTDYHIDQVSNLVDCLSDEFCLDEKRELSEKVKHAKRLSDERNL : 676
cry1Ia    : TDVKDYHIDQVSNLVESLSDEFYLDEKRELFEIVKYAKQLHIERNM : 719
cry2Ab    : ------------------------------------------- : -
cry3Aa1   : ------------------------------------------- : -
cry7Ae    : KDVTDYKVDQVSILVDCISGDLYPNEKRELQMLVKYAKRLSYSRNL : 711
cry8Aa    : PGVTDYEVNQAANLVECLSDDLYPNEKRLLFDAVREAKRLSGARNL : 736
cry10Aa   : ------------------------------------------- : -
```

AXMI-003, A DELTA-ENDOTOXIN GENE AND METHODS FOR ITS USE

CROSS REFERENCE TO RELATED APPLICATION

This application is a Continuation of U.S. application Ser. No. 10/926,819, filed Aug. 26, 2004, (now U.S. Pat. No. 7,253,343), which claims priority to U.S. Provisional Application Ser. No. 60/498,518, filed Aug. 28, 2003, the contents of which are hereby incorporated in their entirety by reference herein.

FIELD OF THE INVENTION

This invention relates to the field of molecular biology. Provided are novel genes that encode pesticidal proteins. These proteins and the nucleic acid sequences that encode them are useful in preparing pesticidal formulations and in the production of transgenic pest-resistant plants.

BACKGROUND OF THE INVENTION

*Bacillus thuringiensis* is a Gram-positive spore forming soil bacterium characterized by its ability to produce crystalline inclusions that are specifically toxic to certain orders and species of insects, but are harmless to plants and other non-targeted organisms. For this reason, compositions including *Bacillus thuringiensis* strains or their insecticidal proteins can be used as environmentally-acceptable insecticides to control agricultural insect pests or insect vectors for a variety of human or animal diseases.

Crystal (Cry) proteins (delta-endotoxins) from *Bacillus thuringiensis* have potent insecticidal activity against predominantly Lepidopteran, Dipteran, and Coleopteran larvae. These proteins also have shown activity against Hymenoptera, Homoptera, Phthiraptera, Mallophaga, and Acari pest orders, as well as other invertebrate orders such as Nemathelminthes, Platyhelminthes, and Sarcomastigorphora (Feitelson (1993) The *Bacillus Thuringiensis* family tree. In Advanced Engineered Pesticides. Marcel Dekker, Inc., New York, N.Y.) These proteins were originally classified as CryI to CryV based primarily on their insecticidal activity. The major classes were Lepidoptera-specific (I), Lepidoptera- and Diptera-specific (II), Coleoptera-specific (III), Diptera-specific (IV), and nematode-specific (V) and (VI). The proteins were further classified into subfamilies; more highly related proteins within each family were assigned divisional letters such as Cry1A, Cry1B, Cry1C, etc. Even more closely related proteins within each division were given names such as Cry1C1, Cry1C2, etc.

A new nomenclature was recently described for the Cry genes based upon amino acid sequence homology rather than insect target specificity (Crickmore et al. (1998) *Microbiol. Mol. Biol. Rev.* 62:807-813). In the new classification, each toxin is assigned a unique name incorporating a primary rank (an Arabic number), a secondary rank (an uppercase letter), a tertiary rank (a lowercase letter), and a quaternary rank (another Arabic number). In the new classification, Roman numerals have been exchanged for Arabic numerals in the primary rank.

The crystal protein does not exhibit insecticidal activity until it has been ingested and solubilized in the insect midgut. The ingested protoxin is hydrolyzed by proteases in the insect digestive tract to an active toxic molecule. (Höfte and Whiteley (1989) *Microbiol. Rev.* 53:242-255). This toxin binds to apical brush border receptors in the midgut of the target larvae and inserts into the apical membrane creating ion channels or pores, resulting in larval death.

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in 'jelly-roll' formation (de Maagd et al., 2001, supra). Domains II and III are involved in receptor recognition and binding, and are therefore considered determinants of toxin specificity.

Because of the devastation that insects can confer there is a continual need to discover new forms of *Bacillus thuringiensis* delta-endotoxins.

SUMMARY OF INVENTION

Compositions and methods for conferring pesticide resistance to bacteria, plants, plant cells, tissues and seeds are provided. Compositions include nucleic acid molecules encoding sequences for delta-endotoxin polypeptides, vectors comprising those nucleic acid molecules, and host cells comprising the vectors. Compositions also include the isolated or recombinant polypeptide sequences of the endotoxin, and antibodies to those polypeptides. The nucleotide sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise transformed bacteria, plants, plant cells, tissues, and seeds.

In particular, isolated nucleic acid molecules corresponding to delta-endotoxin nucleic acid sequences are provided. Additionally, amino acid sequences corresponding to the polynucleotides are encompassed. In particular, the present invention provides for isolated nucleic acid molecules comprising a nucleotide sequence encoding the amino acid sequence shown in SEQ ID NO:2 or 4, or the nucleotide sequence set forth in SEQ ID NO:1 or 3, as well as variants and fragments thereof.

Methods are provided for producing the polypeptides of the invention, and for using those polypeptides for controlling or killing a Lepidopteran or Coleopteran pest.

The compositions and methods of the invention are useful for the production of organisms with pesticide resistance, specifically bacteria and plants. These organisms and compositions derived from them are desirable for agricultural purposes. The compositions of the invention are also useful for generating altered or improved delta-endotoxin proteins that have pesticidal activity, or for detecting the presence of delta-endotoxin proteins or nucleic acids in products or organisms.

DESCRIPTION OF FIGURES

FIGS. 1A-1C show an alignment of AXMI-003 (SEQ ID NO:2) with cry1Aa (SEQ ID NO:5), cry1Ab (SEQ ID NO:6), cry1Ac (SEQ ID NO:7), cry1Ba (SEQ ID NO:8), cry1Ca (SEQ ID NO:9), cry1Fa (SEQ ID NO:10), cry1Ia (SEQ ID NO:11), cry2Ab (SEQ ID NO:12), cry3Aa1 (SEQ ID NO:13), cry7Aa (SEQ ID NO:14), cry8Aa (SEQ ID NO:15), and cry10Aa (SEQ ID NO:16). Toxins having C-terminal non-toxic domains were artificially truncated as shown. The alignment shows the most highly conserved amino acid residues marked with an asterisk (*), and highly conserved amino acid residues marked with a colon (:). Conserved group 1 is found from about amino acid residue 181 to about 202 of SEQ ID NO:2. Conserved group 2 is found from about amino acid residue 254 to about 296 of SEQ ID NO:2. Conserved group 3 is found from about amino acid residue 491 to about 536 of SEQ ID NO:2. Conserved group 4 is found from about amino acid residue 557 to about 567 of SEQ ID NO:2. Conserved group 5 is found from about amino acid residue 633 to about 643 of SEQ ID NO:2.

FIGS. 2A-2C show an alignment of AXMI-003 (SEQ ID NO:2) with cry11e1 (SEQ ID NO:17), cry11a (SEQ ID NO:11), cry11a1 (SEQ ID NO:18), cry11a2 (SEQ ID NO:19), cry11a3 (SEQ ID NO:20), cry11a4 (SEQ ID NO:21), cry11a5 (SEQ ID NO:22), cry11a7 (SEQ ID NO:23), cry11a8 (SEQ ID NO:24), cry11b (SEQ ID NO:25), cry11b1 (SEQ ID NO:26), cry11c (SEQ ID NO:27), cry11c1 (SEQ ID NO:28), cry11c2 (SEQ ID NO:29), cry11d (SEQ ID NO:30), and cry11d1 (SEQ ID NO:31). The alignment shows the most highly conserved amino acid residues marked with an asterisk (*), and highly conserved amino acid residues marked with a colon (:).

DETAILED DESCRIPTION

The present invention is drawn to compositions and methods for regulating pest resistance in organisms, particularly plants or plant cells. The methods involve transforming organisms with a nucleotide sequence encoding a delta-endotoxin protein of the invention. In particular, the nucleotide sequences of the invention are useful for preparing plants and microorganisms that possess pesticidal activity. Thus, transformed bacteria, plants, plant cells, plant tissues and seeds are provided. Compositions are delta-endotoxin nucleic acids and proteins of *Bacillus thuringiensis*. The sequences find use in the construction of expression vectors for subsequent transformation into organisms of interest, as probes for the isolation of other delta-endotoxin genes, and for the generation of altered pesticidal proteins by methods known in the art, such as domain swapping or DNA shuffling. The proteins find use in controlling or killing Lepidopteran or Coleopteran pest populations and for producing compositions with pesticidal activity.

DEFINITIONS

By "delta-endotoxin" is intended a toxin from *Bacillus thuringiensis* that has toxic activity against one or more pests, including, but not limited to, members of the Lepidoptera, Diptera, and Coleoptera orders. In some cases, delta-endotoxin proteins have been isolated from other organisms, including *Clostridium bifermentans* and *Paenibacillus popilliae*. Delta-endotoxin proteins include amino acid sequences deduced from the full-length nucleotide sequences disclosed herein, and amino acid sequences that are shorter than the full-length sequences, either due to the use of an alternate downstream start site, or due to processing that produces a shorter protein having pesticidal activity. Processing may occur in the organism the protein is expressed in, or in the pest after ingestion of the protein. Delta-endotoxins include proteins identified as cry1 through cry43, cyt1 and cyt2, and Cyt-like toxin. There are currently over 250 known species of delta-endotoxins with a wide range of specificities and toxicities. For an expansive list see Crickmore et al. (1998), *Microbiol. Mol. Biol. Rev.* 62:807-813, and for regular updates see Crickmore et al. (2003) "*Bacillus thuringiensis* toxin nomenclature," at www.biols.susx.ac.uk/Home/Neil_Crickmore/Bt/index.

Bacterial genes, such as the AXMI-003 gene of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. Furthermore, it is not often determined a priori which of these codons are used naturally in the bacterium. Thus, it is understood that use of one of the alternate methionine codons may also lead to generation of delta-endotoxin proteins that encode pesticidal activity. For example, an alternate start site for a delta-endotoxin protein of the invention is at base pair 22 of SEQ ID NO:1. Translation from this alternate start site results in the amino acid sequence found in SEQ ID NO:4. These delta-endotoxin proteins are encompassed in the present invention and may be used in the methods of the present invention.

By "plant cell" is intended all known forms of plant, including undifferentiated tissue (e.g. callus), suspension culture cells, protoplasts, leaf cells, root cells, phloem cells, plant seeds, pollen, propagules, embryos and the like. By "plant expression cassette" is intended a DNA construct that is capable of resulting in the expression of a protein from an open reading frame in a plant cell. Typically these contain a promoter and a coding sequence. Often, such constructs will also contain a 3' untranslated region. Such constructs may contain a 'signal sequence' or 'leader sequence' to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. By "leader sequence" is intended any sequence that when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like.

By "plant transformation vector" is intended a DNA molecule that is necessary for efficient transformation of a plant cell. Such a molecule may consist of one or more plant expression cassettes, and may be organized into more than one 'vector' DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell.

"Transgenic plants" or "transformed plants" or "stably transformed plants or cells or tissues" refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

"Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Provided herein are novel isolated nucleotide sequences that confer pesticidal activity. Also provided are the amino acid sequences of the delta-endotoxin proteins. The protein resulting from translation of this gene allows cells to control or kill pests that ingest it.

An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated delta-endotoxin encoding nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A delta-endotoxin protein that is substantially free of cellular material includes preparations of protein having less than about 30%, 20%, 10%, or 5% (by dry weight) of non-delta-endotoxin protein (also referred to herein as a "contaminating protein"). Various aspects of the invention are described in further detail in the following subsections.

Isolated Nucleic Acid Molecules, and Variants and Fragments Thereof

One aspect of the invention pertains to isolated nucleic acid molecules comprising nucleotide sequences encoding delta-endotoxin proteins and polypeptides or biologically active portions thereof, as well as nucleic acid molecules sufficient for use as hybridization probes to identify delta-endotoxin encoding nucleic acids. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

Nucleotide sequences encoding the proteins of the present invention include the sequences set forth in SEQ ID NOS:1 and 3, and complements thereof. By "complement" is intended a nucleotide sequence that is sufficiently complementary to a given nucleotide sequence such that it can hybridize to the given nucleotide sequence to thereby form a stable duplex. The corresponding amino acid sequences for the delta-endotoxin proteins encoded by these nucleotide sequences are set forth in SEQ ID NOS:2 and 4.

Nucleic acid molecules that are fragments of these delta-endotoxin encoding nucleotide sequences are also encompassed by the present invention. By "fragment" is intended a portion of the nucleotide sequence encoding a delta-endotoxin protein. A fragment of a nucleotide sequence may encode a biologically active portion of a delta-endotoxin protein, or it may be a fragment that can be used as a hybridization probe or PCR primer using methods disclosed below. Nucleic acid molecules that are fragments of a delta-endotoxin nucleotide sequence comprise at least about 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150 nucleotides, or up to the number of nucleotides present in a full-length delta-endotoxin encoding nucleotide sequence disclosed herein (for example, 2157 nucleotides for SEQ ID NO:1 and 2136 for SEQ ID NO:3) depending upon the intended use. Fragments of the nucleotide sequences of the present invention will encode protein fragments that retain the biological activity of the delta-endotoxin protein and, hence, retain pesticidal activity. By "retains activity" is intended that the fragment will have at least about 30%, preferably at least about 50%, more preferably at least about 70%, even more preferably at least about 80% of the pesticidal activity of the delta-endotoxin protein. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat No. 5,743, 477, all of which are herein incorporated by reference in their entirety.

A fragment of a delta-endotoxin encoding nucleotide sequence that encodes a biologically active portion of a protein of the invention will encode at least about 15, 25, 30, 50, 75, 100, 125, 150, 175, 200, 250, 300, 350, 400, 450, 500, 550, 600, 650, or 700 contiguous amino acids, or up to the total number of amino acids present in a full-length delta-endotoxin protein of the invention (for example, 719 amino acids for SEQ ID NO:2, and 712 amino acids for SEQ ID NO:4).

Preferred delta-endotoxin proteins of the present invention are encoded by a nucleotide sequence sufficiently identical to the nucleotide sequence of SEQ ID NO:1 or 3. By "sufficiently identical" is intended an amino acid or nucleotide sequence that has at least about 60% or 65% sequence identity, preferably about 70% or 75% sequence identity, more preferably about 80% or 85% sequence identity, most preferably about 90%, 91%, 92%, 93%, 94%, 95%, 96%, 97%, 98% or 99% sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acid sequences, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to delta-endotoxin nucleic acid molecules of the invention. BLAST protein searches can be performed with the BLASTX program, score=50, wordlength=3, to obtain amino acid sequences homologous to delta-endotoxin protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al., 1997, supra. When utilizing BLAST, Gapped BLAST, and PSI-Blast programs, the default parameters of the respective programs (e.g., BLASTX and BLASTN) can be used. See www.ncbi.nlm.nih.gov. Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the vector NTi Program Suite (Informax, Inc). After alignment of amino acid sequences with ClustalW, the percent amino acid identity can be assessed. A non-limiting example of a software program useful for analysis of ClustalW alignments is GeneDoc™. Genedoc™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package (available from Accelrys, Inc., 9865 Scranton Rd., San Diego, Calif., USA). When utilizing the ALIGN program for comparing amino acid sequences, a PAM120 weight residue table, a gap length penalty of 12, and a gap penalty of 4 can be used.

A preferred program is GAP version 10, which uses the algorithm of Needleman and Wunsch, 1970, supra. GAP Version 10 may be used with the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 Scoring Matrix. Equivalent programs may also be used. By "equivalent program" is intended any sequence comparison program that, for any two sequences in question, generates an alignment having identical nucleotide or amino acid residue matches and an identical percent sequence identity when compared to the corresponding alignment generated by GAP Version 10.

The invention also encompasses variant nucleic acid molecules. "Variants" of the delta-endotoxin encoding nucleotide sequences include those sequences that encode the delta-endotoxin proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the delta-endotoxin proteins disclosed in the present invention as discussed below. Variant proteins encompassed by the present invention are biologically active, that is they continue to possess the desired biological activity of the native protein, that is, retaining pesticidal activity. By "retains activity" is intended that the variant will have at least about 30%, preferably at least about 50%, more preferably at least about 70%, even more preferably at least about 80% of the pesticidal activity of the native protein. Methods for measuring pesticidal activity are well known in the art. See, for example, Czapla and Lang (1990) *J. Econ. Entomol.* 83: 2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

The skilled artisan will further appreciate that changes can be introduced by mutation into the nucleotide sequences of the invention thereby leading to changes in the amino acid sequence of the encoded delta-endotoxin proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, preferably, conservative amino acid substitutions may be made at one or more predicted, preferably nonessential amino acid residues. A "nonessential" amino acid residue is a residue that can be altered from the wild-type sequence of a delta-endotoxin protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

There are generally five highly conserved regions among the delta-endotoxin proteins, concentrated largely in the center of the domain or at the junction between domains (Rajamohan et al. (1998) *Prog. Nucleic Acid Res. Mol. Biol.* 60:1-23). The blocks of conserved amino acids for various delta-endotoxins as well as consensus sequences may be found in Schnepf et al. (1998) *Microbio. Mol. Biol. Rev.* 62:775-806 and Lereclus et al. (1989) Role, Structure, and Molecular Organization of the Genes Coding for the Parasporal d-endotoxins of *Bacillus thuringiensis*. In Regulation of Procaryotic Development. Issar Smit, Slepecky, R. A., Setlow, P. American Society for Microbiology, Washington, D.C. 20006. It has been proposed that delta-endotoxins having these conserved regions may share a similar structure, consisting of three domains (Li et al. (1991) *Nature* 353:

815-821). Domain I has the highest similarity between delta-endotoxins (Bravo (1997) *J. Bacteriol.* 179:2793-2801).

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in the alignment of FIGS. 1A-1D. Examples of residues that are conserved but that may allow conservative amino acid substitutions and still retain activity include, for example, residues that have only conservative substitutions between all proteins contained in the alignment of FIGS. 1A-1D. However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

Using methods such as PCR, hybridization, and the like corresponding delta-endotoxin sequences can be identified, such sequences having substantial identity to the sequences of the invention. See, for example, Sambrook J., and Russell, D. W. (2001) *Molecular Cloning: A Laboratory Manual.* (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the delta-endotoxin nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known delta-endotoxin-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, preferably about 25, more preferably at least about 50, 75, 100, 125, 150, 175, 200, 250, 300, 350, or 400 consecutive nucleotides of delta-endotoxin encoding nucleotide sequence of the invention or a fragment or variant thereof. Preparation of probes for hybridization is generally known in the art and is disclosed in Sambrook and Russell, 2001, supra, herein incorporated by reference.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the delta-endotoxin sequence of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire delta-endotoxin sequence disclosed herein, or one or more portions thereof, may be used as a probe capable of specifically hybridizing to corresponding delta-endotoxin-like sequences and messenger RNAs. To achieve specific hybridization under a variety of conditions, such probes include sequences that are unique and are preferably at least about 10 nucleotides in length, and most preferably at least about 20 nucleotides in length. Such probes may be used to amplify corresponding delta-endotoxin sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Isolated Proteins and Variants and Fragments Thereof

Delta-endotoxin proteins are also encompassed within the present invention. By "delta-endotoxin protein" is intended a protein having the amino acid sequence set forth in SEQ ID NO:2 or 4. Fragments, biologically active portions, and variants thereof are also provided, and may be used to practice the methods of the present invention.

"Fragments" or "biologically active portions" include polypeptide fragments comprising a portion of an amino acid sequence encoding a delta-endotoxin protein as set forth in SEQ ID NO:2 or 4 and that retain pesticidal activity. A biologically active portion of a delta-endotoxin protein can be a polypeptide that is, for example, 10, 25, 50, 100 or more amino acids in length. Such biologically active portions can be prepared by recombinant techniques and evaluated for pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety. As used here, a fragment comprises at least 8 contiguous amino acids of SEQ ID NO:2 or 4. The invention encompasses other fragments, however, such as any fragment in the protein greater than about 10, 20, 30, 50, 100, 150, 200, 250, 300, 350, 400, 450, 500, 550, 600, 650 and 700 amino acids.

By "variants" is intended proteins or polypeptides having an amino acid sequence that is at least about 60%, 65%, preferably about 70%, 75%, more preferably about 80%, 85%, most preferably about 90%, 91%, 92%, 93%, 94%, 95%, 96%, 97%, 98% or 99% identical to the amino acid sequence of SEQ ID NO:2 or 4. Variants also include polypeptides encoded by a nucleic acid molecule that hybridizes to the nucleic acid molecule of SEQ ID NO:1 or 3, or a complement thereof, under stringent conditions. Such variants generally retain pesticidal activity. Variants include polypeptides that differ in amino acid sequence due to mutagenesis. Variant proteins encompassed by the present invention are biologically active, that is they continue to possess the desired biological activity of the native protein, that is, retaining pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

Altered or Improved Variants

It is recognized that DNA sequences of a delta-endotoxin may be altered by various methods, and that these alterations may result in DNA sequences encoding proteins with amino acid sequences different than that encoded by the delta-endotoxin of the present invention. This protein may be altered in various ways including amino acid substitutions, deletions, truncations, and insertions. Methods for such manipulations are generally known in the art. For example, amino acid sequence variants of the delta-endotoxin protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of delta-endotoxin to confer pesticidal activity may be improved by the use of such techniques upon the compositions of this invention. For example, one may express delta-endotoxin in host cells that exhibit high rates of base misincorporation during DNA replication, such as XL-1 Red (Stratagene). After propagation in such strains, one can isolate the delta-endotoxin DNA (for example by preparing plasmid DNA, or by amplifying by PCR and cloning the resulting PCR fragment into a vector), culture the delta-endotoxin mutations in a non-mutagenic strain, and identify mutated delta-endotoxin genes with pesticidal activity, for example by performing an assay to test for pesticidal activity. Generally, the protein is mixed and used in feeding assays. See, for example Marrone et al. (1985) *J. of Economic Entomology* 78:290-293. Such assays can include contacting plants with one or more pests and determining the plant's ability to survive and/or cause the death of the pests. Examples of mutations that result in increased toxicity are found in Schnepf et al. (1998) *Microbiol. Mol. Biol. Rev.* 62:775-806.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different delta-endotoxin protein coding regions can be used to create a new delta-endotoxin protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the delta-endotoxin gene of the invention and other known delta-endotoxin genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered delta-endotoxin proteins. Domains II and III may be swapped between delta-endotoxin proteins, resulting in hybrid or chimeric toxins with improved pesticidal activity or target spectrum. Methods for generating recombinant proteins and testing them for pesticidal activity are well known in the art (see, for example, Naimov et al. (2001) *Appl. Environ. Microbiol.* 67:5328-5330; de Maagd et al. (1996) *Appl. Environ. Microbiol.* 62:1537-1543; Ge et al. (1991) *J. Biol. Chem.* 266:17954-17958; Schnepf et al. (1990) *J. Biol. Chem.* 265:20923-20930; Rang et al. 91999) *Appl. Environ. Micriobiol.* 65:2918-2925).

Plant Transformation

Transformation of plant cells can be accomplished by one of several techniques known in the art. First, one engineers the delta-endotoxin gene in a way that allows its expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this ‘plant expression cassette’ will be inserted into a ‘plant transformation vector’. This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as ‘binary vectors’. Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a ‘gene of interest’ (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the gene of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as in understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Generation of transgenic plants may be performed by one of several methods, including but not limited to introduction of heterologous DNA by *Agrobacterium* into plant cells (*Agrobacterium*-mediated transformation), bombardment of plant cells with heterologous foreign DNA adhered to particles, and various other non-particle direct-mediated methods (e.g. Hiei et al. (1994) *The Plant Journal* 6:271-282; Ishida et al. (1996) *Nature Biotechnology* 14:745-750; Ayres and Park (1994) *Critical Reviews in Plant Science* 13:219-239; Bommineni and Jauhar (1997) *Maydica* 42:107-120) to transfer DNA.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. No. 5,563,055; U.S. Pat. No. 5,981,840), direct gene transfer (Paszkowski et al. (1984) *EMBO J.* 3:2717-2722), and ballistic particle acceleration (see, for example, U.S. Pat. No. 4,945,050; U.S. Pat. No. 5,879,918; U.S. Pat. No. 5,886,244; U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); aerosol beam transformation (U.S. Published Application No. 20010026941; U.S. Pat. No. 4,945,050; International Publication No. WO 91/00915; U.S. Published Application No. 2002015066); and Lec1 transformation (WO 00/28058). Also see Weissinger et al. (1988) *Ann. Rev. Genet.* 22:421-477; Sanford et al. (1987) *Particulate Science and Technology* 5:27-37; Christou et al. (1988) *Plant Physiol.* 87:671-674; McCabe et al. (1988) *Bio/Technology* 6:923-926; Finer and McMullen (1991) *In Vitro Cell Dev. Biol.* 27P:175-182; Singh et al. (1998) *Theor. Appl. Genet.* 96:319-324; Datta et al. (1990) *Biotechnology* 8:736-740; Klein et al. (1988) *Proc. Natl. Acad. Sci. USA* 85:4305-4309; U.S. Pat. No. 5,240,855; U.S. Pat. Nos. 5,322,783 and 5,324,646; Klein et al. (1988) *Plant Physiol.* 91:440-444; Hooykaas-Van Slogteren et al. (1984) *Nature (London)* 311:763-764; U.S. Pat. No. 5,736,369; Bytebier et al. (1987) *Proc. Natl. Acad. Sci. USA* 84:5345-5349; De Wet et al. (1985) in *The Experimental Manipulation of Ovule Tissues*, ed. Chapman et al. (Longman, New York), pp. 197-209; Kaeppler et al. (1990) *Plant Cell Reports* 9:415-418 and Kaeppler et al. (1992) *Theor. Appl. Genet.* 84:560-566; D'Halluin et al. (1992) *Plant Cell* 4:1495-1505; Li et al. (1993) *Plant Cell Reports* 12:250-255 and Christou and Ford (1995) *Annals of Botany* 75:407-413; Osjoda et al. (1996) *Nature Biotechnology* 14:745-750; all of which are herein incorporated by reference.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Then molecular and biochemical methods will be used for confirming the presence of the integrated heterologous gene of interest in the genome of transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

The delta-endotoxin sequences of the invention may be provided in expression cassettes for expression in the plant of interest. The cassette will include 5' and 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the delta-endotoxin sequence to be under the transcriptional regulation of the regulatory regions.

The expression cassette will include in the 5'-3' direction of transcription, a transcriptional and translational initiation region (i.e., a promoter), a DNA sequence of the invention, and a transcriptional and translational termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

In one embodiment, the nucleic acids of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR Analysis:

PCR analysis is a rapid method to screen transformed cells, tissue or shoots for the presence of incorporated gene at the earlier stage before transplanting into the soil (Sambrook and Russell (2001) *Molecular Cloning: A Laboratory Manual*. Cold Spring Harbor Laboratory Press, Cold Spring Harbor, N.Y.). PCR is carried out using oligonucleotide primers specific to the gene of interest or *Agrobacterium* vector background, etc.

Southern Analysis:

Plant transformation is confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" then is probed with, for example, radiolabeled $^{32}P$ target DNA fragment to confirm the integration of introduced gene in the plant genome according to standard techniques (Sambrook and Russell, 2001, supra).

Northern Analysis:

RNA is isolated from specific tissues of transformant, fractionated in a formaldehyde agarose gel, blotted onto a nylon filter according to standard procedures that are routinely used in the art (Sambrook and Russell, 2001, supra). Expression of RNA encoded by the delta-endotoxin is then tested by hybridizing the filter to a radioactive probe derived from a delta-endotoxin, by methods known in the art (Sambrook and Russell, 2001, supra).

Western Blot and Biochemical Assays:

Western blot and biochemical assays and the like may be carried out on the transgenic plants to confirm the presence of protein encoded by the delta-endotoxin gene by standard procedures (Sambrook and Russell, 2001, supra) using antibodies that bind to one or more epitopes present on the delta-endotoxin protein.

Pesticidal Activity in Plants

In another aspect of the invention, one may generate transgenic plants expressing delta-endotoxin that have pesticidal activity. Methods described above by way of example may be utilized to generate transgenic plants, but the manner in which the transgenic plant cells are generated is not critical to this invention. Methods known or described in the art such as *Agrobacterium*-mediated transformation, aerosol beam, biolistic transformation, and non-particle-mediated methods may be used at the discretion of the experimenter. Plants expressing delta-endotoxin may be isolated by common methods described in the art, for example by transformation of callus, selection of transformed callus, and regeneration of fertile plants from such transgenic callus. In such process, one may use any gene as a selectable marker so long as its expression in plant cells confers ability to identify or select for transformed cells.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene).

Fertile plants expressing delta-endotoxin may be tested for pesticidal activity, and the plants showing optimal activity selected for further breeding. Methods are available in the art to assay for pest activity. Generally, the protein is mixed and used in feeding assays. See, for example Marrone et al. (1985) *J. of Economic Entomology* 78:290-293.

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Cucumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape., etc.).

Use in Pesticidal Control

General methods for employing the strains of the invention in pesticide control or in engineering other organisms as pesticidal agents are known in the art. See, for example U.S. Pat. No. 5,039,523 and EP 0480762A2.

The *Bacillus* strains of the invention or the microorganisms that have been genetically altered to contain the pesticidal gene and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticide is produced by introducing a heterologous gene into a cellular host. Expression of the heterologous gene results, directly or indirectly, in the intracellular production and maintenance of the pesticide. In one aspect of this invention, these cells are then treated under conditions that prolong the activity of the toxin produced in the cell when the cell is applied to the environment of target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein. Alternatively, one may formulate the cells expressing the genes of this invention such as to allow application of the resulting material as a pesticide.

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Preferred methods of applying an active ingredient of the present invention or an agrochemical composition of the present invention that contains at least one of the pesticidal proteins produced by the bacterial strains of the present invention are leaf application, seed coating and soil application. The number of applications and the rate of application depend on the intensity of infestation by the corresponding pest.

The composition may be formulated as a powder, dust, pellet, granule, spray, emulsion, colloid, solution, or such like, and may be preparable by such conventional means as desiccation, lyophilization, homogenation, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

Lepidopteran or Coleopteran pests may be killed or reduced in numbers in a given area by the methods of the invention, or may be prophylactically applied to an environmental area to prevent infestation by a susceptible pest. Preferably the pest ingests, or is contacted with, a pesticidally-effective amount of the polypeptide. By "pesticidally-effective amount" is intended an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference.

"Pest" includes but is not limited to, insects, fungi, bacteria, nematodes, mites, ticks, and the like. Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid;

*Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Praylenchus* pp.

The following examples are offered by way of illustration and not by way of limitation.

EXPERIMENTAL

Example 1

Extraction of Plasmid DNA

A pure culture of strain ATX13002 was grown in large quantities of rich media. The culture was spun to harvest the cell pellet. The cell pellet was then prepared by treatment with SDS allowing breakage of the cell wall and release of DNA. Proteins and large genomic DNA was then precipitated by a high salt concentration. The plasmid DNA was then precipitated by standard ethanol precipitation. The plasmid DNA was separated from any remaining chromosomal DNA by high-speed centrifugation through a cesium chloride gradient. The DNA was visualized in the gradient by UV light and the band of lower density (i.e. the lower band) was extracted using a syringe. This band contained the plasmid DNA from strain ATX13002. The quality of the DNA was checked by visualization on an agarose gel.

Example 2

Cloning of Genes

The purified plasmid DNA was sheared into 5-10 kb sized fragments and the 5' and 3' single-stranded overhangs repaired using T4 DNA polymerase and Klenow fragment in the presence of all four dNTPs, as known in the art. Phosphates were then attached to the 5' ends by treatment with T4 polynucleotide kinase, as known in the art. The repaired DNA fragments were then ligated overnight into a standard high copy vector (i.e. pBluescript SK+), suitably prepared to accept the inserts as known in the art (for example by digestion with a restriction enzyme producing blunt ends).

The quality of the library was analyzed by digesting a subset of clones with a restriction enzyme known to have a cleavage site flanking the cloning site. A high percentage of clones were determined to contain inserts, with an average insert size of 5-6 kb.

Example 3

High Throughput Sequencing of Library Plates

Once the shotgun library quality was checked and confirmed, colonies were grown in a rich broth in 2 ml 96-well blocks overnight at 37° C. at a shaking speed of 350 rpm. The blocks were spun to harvest the cells to the bottom of the block. The blocks were then prepared by standard alkaline lysis prep in a high throughput format.

The end sequences of clones from this library were then determined for a large number of clones from each block in the following way: The DNA sequence of each clone chosen for analysis was determined using the fluorescent dye terminator sequencing technique (Applied Biosystems) and standard primers flanking each side of the cloning site. Once the reactions had been carried out in the thermocycler, the DNA was precipitated using standard ethanol precipitation. The DNA was resuspended in water and loaded onto a capillary sequencing machine. Each library plate of DNA was sequenced from either end of the cloning site, yielding two reads per plate over each insert.

Example 4

Assembly and Screening of Sequencing Data

DNA sequences obtained were compiled into an assembly project and aligned together to form contigs. This can be done efficiently using a computer program, such as Vector NTi, or alternatively by using the Pred/Phrap suite of DNA alignment and analysis programs. These contigs, along with any individual read that may not have been added to a contig, were compared to a compiled database of all classes of known pesticidal genes. Contigs or individual reads identified as having identity to a known endotoxin or pesticidal gene were analyzed further. Among the sequences obtained, clone pAX003 contained DNA identified as having homology to known endotoxin genes. Therefore, pAX003 was selected for further sequencing.

Example 5

Sequencing of pAX003, and Identification of AXMI-003

Primers were designed to anneal to pAX003, in a manner such that DNA sequences generated from such primers will overlap existing DNA sequence of the clone(s). This process, known as "oligo walking", is well known in the art. This process was utilized to determine the entire DNA sequence of the region exhibiting homology to a known endotoxin gene. In the case of pAX003, this process was used to determine the DNA sequence of the entire clone, resulting in a single nucleotide sequence. The completed DNA sequence was then placed back into the original large assembly for further validation. This allowed incorporation of more DNA sequence reads into the contig, resulting in multiple reads of coverage over the entire region.

Analysis of the DNA sequence of pAX003 by methods known in the art identified an open reading frame with homology to known delta endotoxin genes. This open reading frame is designated as AXMI-003. The DNA sequence of AXMI-003 is provided as SEQ ID NO:1 and SEQ ID NO:3, and the amino acid sequence of the predicted AXMI-003 protein is provided in SEQ ID NO:2 and SEQ ID NO:4.

Example 6

Homology of AXMI-003 to Known Endotoxin Genes

Searches of DNA and protein databases with the DNA sequence and amino acid sequence of AXMI-003 reveal that AXMI-003 is homologous to known endotoxins.

Blast searches identify members of the cry1I family of endotoxins as having the strongest block of homology to AXMI-003. AXMI-003 protein (SEQ ID NO:2) was aligned with a large set of holotype endotoxin genes (Crickmore et al. (1998) *Biology Reviews* 62:807-813). This alignment shows that AXMI-003 has the conserved domains typical of an endotoxin. A subset of the alignment is shown in FIG. 1. Table 1 shows the percent identity of the AXMI-003 protein to several endotoxins. This alignment demonstrates that the AXMI-003 protein (SEQ ID NO:2) is most homologous to the cry1I family of endotoxins. The overall amino acid identity of AXMI-003 to cry1Ia (SEQ Id NO:11) is 90% (see Table 1). The endotoxin family with the next highest homology to AXMI-003 is cry1Ba (SEQ ID NO:8), which is 57% identical to AXMI-003 over the length of the AXMI-003 protein. Inspection of the amino acid sequence of AXMI-003 suggests that it does not contain a C-terminal non-toxic domain as is present in several endotoxin families. By removing this C-terminal protein of the toxins from the alignment, the alignment reflects the amino acid identity present solely in the toxin domains (see Table 1, column three). This 'trimmed' alignment of AXMI-003 with several exemplary endotoxins is shown in FIG. 1.

Alignment of AXMI-003 protein (SEQ ID NO:2) to a set of cry1I toxins is shown in FIG. 2. AXMI-003 has the highest homology to cry1IE1 (95% identity; U.S. Pat. No. 5,985,267; SEQ ID NO:17). However, there are clear differences between AXMI-003 and the existing cry1I toxins, including cry1IE1.

TABLE 1

Amino Acid Identity of AXMI-003 with Exemplary Endotoxin Classes

| Endotoxin | Amino Acid Identity of Truncated Toxins to AXMI-003 (SEQ ID NO: 2) |
|---|---|
| cry1Aa (SEQ ID NO: 5) | 39% |
| cry1Ab (SEQ ID NO: 6) | 39% |
| cry1Ac (SEQ ID NO: 7) | 33% |
| cry1Ba (SEQ ID NO: 8) | 59% |
| cry1Ca (SEQ ID NO: 9) | 36% |
| cry1Fa (SEQ ID NO: 10) | 37% |
| cry1Ia (SEQ ID NO: 11) | 90% |
| cry2Ab (SEQ ID NO: 12) | 12% |
| cry3Aa1 (SEQ ID NO: 13) | 31% |
| cry7Aa (SEQ ID NO: 14) | 36% |
| cry8Aa (SEQ ID NO: 15) | 43% |
| cry10Aa (SEQ ID NO: 16) | 20% |

Example 7

Construction of pAX300 and pAX303 pAX300 is an expression vector derived from pMal-2cx (New England Biolabs) by digesting pMAl-2cx with the restriction enzymes NdeI and EcoICRI, converting the overhangs to blunt ends by treatment with T4 polymerase and dNTPs, and religating the vector. pAX303 is a variant of pAX300 that confers kanamycin resistance rather than ampicillin resistance. pAX303 was generated from pAX300 by (1) digesting pAX300 with BspHI to remove beta-lactamase, converting the overhangs to blunt ends by treatment with T4 DNA polymerase and dNTPs, and removing the 5' phosphates with calf intestinal phosphatase (New England Biolabs), (2) isolating the kanamycin resistance marker from pUC4K (Amersham Biosciences) by digestion with PstI, converting the 5' overhangs to blunt ends with T4 DNA polymerase and dNTPs, and gel-purifying the blunt-ended fragment, (3) ligating the fragment from pUC4K to the phosphatase-treated vector, and identifying kanamycin resistant clones. The resulting vector is pAX303.

Example 8

Expression of AXMI-003 Open Reading Frame in *E. coli*

AXMI-003 was engineered for expression in *E. coli* in the following manner. AXMI-003 was amplified by PCR, and cloned into pGEX-4T1 (Amersham Biosciences), which was digested with BamHI and SalI to yield pAX413. AXMI-003 is organized such that the AXMI-003 open reading frame is translated as a fusion with the GST protein of the pGEX vector.

pAX413 was digested with BamHI and SalI, and the restriction fragment containing the AXMI-003 purified by agarose gel electrophoresis. pAX303 was digested with BamHI and SalI, and the AXMI-containing insert ligated to pAX303, to yield pAX900. The ligation was transformed into *E. coli* by electroporation.

Example 9

Bioassay of *E. coli* Construct Expressing AXMI-003 on European Corn Borer

*E. coli* cells containing pAX900 were grown in media, and AXMI-003 protein expression induced by addition of 1 mM IPTG to the growth media. Cells from AXMI-003 expressing cells or vector controls were pelleted by centrifugation, and lysed. Lysed cells were topically applied to artificial insect diet, and the diet allowed to dry. Once the diet was dry, neonate larvae of *Ostrinia nubilulis* (European corn borer) were placed in the wells, and incubated for 4 days. At the end of 4 days, the percent mortality was assessed.

TABLE 2

Percent Mortality of AXMI-003 on European Corn Borer

| Construct | Percent Mortality (4 days) |
|---|---|
| AXMI-003 Trial #1 | 100% |
| AXMI-003 Trial #2 | 100% |
| Vector Alone | 0% |

Example 10

Expression of AXMI-003 in *Bacillus*

The 2,160 base pair insecticidal AXMI-003 gene was digested from pAX900 using the restriction enzymes BamHI and SalI. The DNA fragment was gel purified from the vector backbone and cloned into the *Bacillus* expression vector pAX916 by methods well known in the art. The resulting clone, pAX964, expressed AXMI-003 protein when transformed into cells of a cry(−) *Bacillus thuringiensis* strain. The *Bacillus* strain containing pAX964 and expressing the 79 kD AXMI-003 insecticidal protein may be cultured on a variety of conventional growth media. A *Bacillus* strain containing pAX964 was grown in CYS media (10 g/l Bacto-casitone; 3 g/l yeast extract; 6 g/l $KH_2PO_4$; 14 g/l $K_2HPO_4$; 0.5 mM $MgSO_4$; 0.05 mM $MnCl_2$; 0.05 mM $FeSO_4$), until sporulation was evident by microscopic examination. Soluble protein ampules were prepared, and AXMI-003 was tested for insecticidal activity in bioassay against several species.

Example 11

Bioassay of *Bacillus*-Expressed AXMI-003 on Insect Pests

Insecticidal activity of AXMI-003 was established utilizing accepted bioassay procedures using a sporulated *Bacillus* cell culture lysate expressing AXMI-003. The *Bacillus* culture was grown in 50 ml CYS media for 3 days at 30° C., 250 rpm until the cells were sporulated. Sporulation was confirmed by microscopic examination for the presence of spores. AXMI-003 protein samples were prepared by centrifugation of the sporulated cultures at 12,000×g for 10 min. The pellet was collected and resuspended in 50 ml 20 mM Tris-HCl, pH 8.0. The suspension was centrifuged again to collect the cell pellet. The pellet was resuspended in 50 ml of solubilization buffer (50 mM sodium carbonate, pH 10). The protein concentration of the sample was determined by electrophoresis on an SDS 4-20% gradient acrylamide gel along with a known quantity of bovine serum albumin (BSA). The concentration of AXMI-003 was determined to be 10 ng/ul.

AXMI-003 insecticidal activity was tested using a surface treatment bioassay with artificial diet (Multiple Species diet, Southland Products, Lake Village, Ark.) prepared as known in the art. Bioassays were carried out by applying the *Bacillus* culture expressing AXMI-003 to the diet surface and allowing the surface to air-dry. Standard bioassays utilized five to ten eggs or neonate larvae per well, depending on the species. $LC_{50}$ bioassays utilized five neonate insect larvae per well. The eggs or larvae were applied using a fine tip paintbrush. Standard surface bioassays were carried out in 24-well tissue culture plates. 40 µl of each sample was applied to each well. Since each well has a surface area of 2 $cm^2$ (plate source), a 40 µl cell lysate sample contained approximately 0.4 µg of AXMI-003. The final amount of AXMI-003 protein in each bioassay was approximately 0.2 µg/$cm^2$. Bioassay trays were sealed with Breathe Easy Sealing Tape (Diversified Biotech, Boston Mass.). Control samples included media only samples, and wells that were not treated with samples. Bioassays were then held for five days in the dark at 25° C. and 65% relative humidity and results recorded.

TABLE 3

Insecticidal Activity of AXMI-003

| Insect (Latin Name) | Common Name | Activity of AXMI-004 |
|---|---|---|
| *Ostrinia nubilalis* | European Corn Borer | 100% mortality |
| *Pectinophora gossypiella* | Pink Bollworm | 100% mortality |
| *Manduca sexta* | Tobacco Hornworm | 100% mortality |
| *Spodoptera exigua* | Beet Armyworm | stunting |
| *Spodoptera frugiperda* | Fall Armyworm | stunting |

AXMI-003 showed strong insecticidal activity (100% mortality) against *Ostrinia nubilalis, Pectinophora gossypiella* and *Manduca sexta*. AXMI-003 also severely stunted the growth of *Spodoptera exigua* and *Spodoptera frugiperda* at concentrations over 4.8 µg/$cm^2$.

Example 12

Additional Assays for Pesticidal Activity

The ability of a pesticidal protein to act as a pesticide upon a pest is often assessed in a number of ways. One way well known in the art is to perform a feeding assay. In such a feeding assay, one exposes the pest to a sample containing either compounds to be tested, or control samples. Often this is performed by placing the material to be tested, or a suitable dilution of such material, onto a material that the pest will ingest, such as an artificial diet. The material to be tested may be composed of a liquid, solid, or slurry. The material to be tested may be placed upon the surface and then allowed to dry. Alternatively, the material to be tested may be mixed with a molten artificial diet, then dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouth parts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson, J. L. & H. K. Preisler. 1992. *Pesticide bioassays with arthropods*. CRC, Boca Raton, Fla. Alternatively, assays are commonly described in the journals "Arthropod Management Tests" and "Journal of Economic Entomology" or by discussion with members of the Entomological Society of America (ESA).

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A recombinant nucleic acid molecule selected from the group consisting of:
   a) a nucleic acid molecule comprising a nucleotide sequence having at least 99% sequence identity across the entirety of the nucleotide sequence of SEQ ID NO:1 or 3, wherein said nucleotide sequence encodes a polypeptide having pesticidal activity; and,
   b) a nucleic acid molecule that encodes a polypeptide comprising an amino acid sequence having at least 98% sequence identity across the entirety of the amino acid sequence of SEQ ID NO:2 or 4, wherein said polypeptide has pesticidal activity.

2. The recombinant nucleic acid molecule of claim 1, wherein said nucleotide sequence is a synthetic sequence that has been designed for expression in a plant.

3. A vector comprising the nucleic acid molecule of claim 1.

4. The vector of claim 3, further comprising a nucleic acid molecule encoding a heterologous polypeptide.

5. A host cell that contains the vector of claim 3.

6. The host cell of claim 5 that is a bacterial host cell.

7. The host cell of claim 5 that is a plant cell.

8. A transgenic plant comprising the host cell of claim 7.

9. The transgenic plant of claim 8, wherein said plant is selected from the group consisting of maize, sorghum, wheat, sunflower, tomato, crucifers, peppers, potato, cotton, rice, soybean, cabbage sugarbeet, sugarcane, tobacco, barley, and oilseed rape.

10. A transformed seed comprising the nucleic acid molecule of claim 1.

11. A method for producing a polypeptide with pesticidal activity, comprising culturing the host cell of claim 5 under conditions in which the nucleic acid molecule encoding the polypeptide is expressed.

12. A plant having stably incorporated into its genome a DNA construct comprising a nucleotide sequence that encodes a protein having pesticidal activity, wherein said nucleotide sequence is selected from the group consisting of:
   a) a nucleic acid molecule comprising a nucleotide sequence having at least 99% sequence identity across the entirety of the nucleotide sequence of SEQ ID NO:1 or 3, wherein said nucleotide sequence encodes a polypeptide having pesticidal activity; and,
   b) a nucleic acid molecule that encodes a polypeptide comprising an amino acid sequence having at least 99% sequence identity across the entirety of the amino acid sequence of SEQ ID NO:2 or 4, wherein said polypeptide has pesticidal activity;

wherein said nucleotide sequence is operably linked to a promoter that drives expression of a coding sequence in a plant cell.

13. A plant cell having stably incorporated into its genome a DNA construct comprising a nucleotide sequence that encodes a protein having pesticidal activity, wherein said nucleotide sequence is selected from the group consisting of:
   a) a nucleic acid molecule comprising a nucleotide sequence having at least 99% sequence identity across the entirety of the nucleotide sequence of SEQ ID NO:1 or 3, wherein said nucleotide sequence encodes a polypeptide having pesticidal activity; and,
   b) a nucleic acid molecule that encodes a polypeptide comprising an amino acid sequence having at least 99% sequence identity across the entirety of the amino acid sequence of SEQ ID NO:2 or 4, wherein said polypeptide has pesticidal activity;

wherein said nucleotide sequence is operably linked to a promoter that drives expression of a coding sequence in a plant cell.

14. A method for expressing a nucleotide sequence in a plant, said method comprising introducing into a plant cell an expression cassette, said expression cassette comprising a promoter and operably linked to said promoter a heterologous nucleotide sequence of interest, wherein said nucleotide sequence of interest comprises a nucleotide sequence selected from the group consisting of:
   a) a nucleic acid molecule comprising a nucleotide sequence having at least 99% sequence identity across the entirety of the nucleotide sequence of SEQ ID NO:1 or 3, wherein said nucleotide sequence encodes a polypeptide having pesticidal activity; and,
   b) a nucleic acid molecule that encodes a polypeptide comprising an amino acid sequence having at least 99% sequence identity across the entirety of the amino acid sequence of SEQ ID NO:2 or 4, wherein said polypeptide has pesticidal activity; and, regenerating a transformed plant from said plant cell, wherein said plant has stably incorporated into its genome said expression cassette.

15. A method for expressing a nucleotide sequence in a plant cell, said method comprising introducing into a plant cell an expression cassette comprising a promoter operably linked to a heterologous nucleotide sequence of interest, wherein said nucleotide sequence of interest comprises a nucleotide sequence selected from the group consisting of:
   a) a nucleic acid molecule comprising a nucleotide sequence having at least 99% sequence identity across the entirety of the nucleotide sequence of SEQ ID NO:1 or 3, wherein said nucleotide sequence encodes a polypeptide having pesticidal activity; and, b) a nucleic acid molecule that encodes a polypeptide comprising an amino acid sequence having at least 99% sequence identity across the entirety of the amino acid sequence of SEQ ID NO:2 or 4, wherein said polypeptide has pesticidal activity.

* * * * *

SEQUENCE LISTING

```
<160> NUMBER OF SEQ ID NOS: 31

<210> SEQ ID NO 1
<211> LENGTH: 2157
<212> TYPE: DNA
<213> ORGANISM: Bacillus thuringiensis
<220> FEATURE:
<221> NAME/KEY: CDS
<222> LOCATION: (1)...(2157)

<400> SEQUENCE: 1 atg aaa tcg aag aat caa gat atg tat caa aga tta tct tac aat aca      48
Met Lys Ser Lys Asn Gln Asp Met Tyr Gln Arg Leu Ser Tyr Asn Thr
 1               5                  10

| | |
|---|---|
| gca gta tca ggt gag gaa gta cca tta ttg cca ata tat gca caa gct<br>Ala Val Ser Gly Glu Glu Val Pro Leu Leu Pro Ile Tyr Ala Gln Ala<br>           180                          185                         190 | 576 |
| gca aat tta cac tta tta tta cta aga gat gct tct gtt ttt gga aaa<br>Ala Asn Leu His Leu Leu Leu Arg Asp Ala Ser Val Phe Gly Lys<br>                195                       200                        205 | 624 |
| gag tgg gga tta tct aat tcg caa att tct aca ttt tat aat cgt caa<br>Glu Trp Gly Leu Ser Asn Ser Gln Ile Ser Thr Phe Tyr Asn Arg Gln<br>      210                        215                       220 | 672 |
| gtc gaa aga acg agt gac tat tcc gac cat tgt gtg aaa tgg tat agt<br>Val Glu Arg Thr Ser Asp Tyr Ser Asp His Cys Val Lys Trp Tyr Ser<br>225                        230                        235                   240 | 720 |
| aca ggt cta aat aac ttg aga ggt aca aat gcc gaa agc tgg gtc cgt<br>Thr Gly Leu Asn Asn Leu Arg Gly Thr Asn Ala Glu Ser Trp Val Arg<br>                       245                       250                       255 | 768 |
| tat aat caa ttt cgt aaa gat atg aca tta atg gta cta gat tta atc<br>Tyr Asn Gln Phe Arg Lys Asp Met Thr Leu Met Val Leu Asp Leu Ile<br>                260                       265                       270 | 816 |
| gca tta ttc cca agc tat gat aca ctt gta tat cca att aaa acc act<br>Ala Leu Phe Pro Ser Tyr Asp Thr Leu Val Tyr Pro Ile Lys Thr Thr<br>             275                       280                       285 | 864 |
| tct caa ctt aca aga gaa gta tat aca gac gca att ggg aca gta cat<br>Ser Gln Leu Thr Arg Glu Val Tyr Thr Asp Ala Ile Gly Thr Val His<br>      290                        295                       300 | 912 |
| cca aat gca agt ttt gca agt acg acc tgg tat aat aat aat gca cct<br>Pro Asn Ala Ser Phe Ala Ser Thr Thr Trp Tyr Asn Asn Asn Ala Pro<br>305                        310                        315                   320 | 960 |
| tcg ttc tct gcc ata gag tct gct gtt gtt cga aac ccg cat cta ctc<br>Ser Phe Ser Ala Ile Glu Ser Ala Val Val Arg Asn Pro His Leu Leu<br>                       325                       330                       335 | 1008 |
| gat ttt tta gaa caa gtt aca att tac agc tta tta agt agg tgg agt<br>Asp Phe Leu Glu Gln Val Thr Ile Tyr Ser Leu Leu Ser Arg Trp Ser<br>                340                       345                       350 | 1056 |
| aac act cag tat atg aat atg tgg gga gga cat aga ctg gaa ttc cga<br>Asn Thr Gln Tyr Met Asn Met Trp Gly Gly His Arg Leu Glu Phe Arg<br>             355                       360                       365 | 1104 |
| aca ata ggt gga gtg tta aat acc tca aca caa ggg tct act aat act<br>Thr Ile Gly Gly Val Leu Asn Thr Ser Thr Gln Gly Ser Thr Asn Thr<br>      370                        375                       380 | 1152 |
| tct att aat cct gta aca tta ccg ttc acg tct cga gac gtc tat agg<br>Ser Ile Asn Pro Val Thr Leu Pro Phe Thr Ser Arg Asp Val Tyr Arg<br>385                        390                        395                   400 | 1200 |
| act gaa tca ttg gca ggg ctg aat cta ttt tta act caa cct gtt aat<br>Thr Glu Ser Leu Ala Gly Leu Asn Leu Phe Leu Thr Gln Pro Val Asn<br>                       405                       410                       415 | 1248 |
| gga gta cct agg gtt gat ttt cat tgg aaa ttc gcc aca ctt ccg att<br>Gly Val Pro Arg Val Asp Phe His Trp Lys Phe Ala Thr Leu Pro Ile<br>                  420                       425                       430 | 1296 |
| gca tct gat aat ttc tat tat cca ggg tat gct gga att ggg acg caa<br>Ala Ser Asp Asn Phe Tyr Tyr Pro Gly Tyr Ala Gly Ile Gly Thr Gln<br>             435                       440                       445 | 1344 |
| tta caa gat tca gaa aat gaa tta cct cct gaa aca aca gga cag cca<br>Leu Gln Asp Ser Glu Asn Glu Leu Pro Pro Glu Thr Thr Gly Gln Pro<br>      450                        455                       460 | 1392 |
| aat tat gaa tca tat agt cat aga tta tct cat ata gga ctc att tca<br>Asn Tyr Glu Ser Tyr Ser His Arg Leu Ser His Ile Gly Leu Ile Ser<br>465                        470                        475                   480 | 1440 |
| gca tca cat gtg aaa gca ttg gta tat tct tgg acg cat cgt agt gca<br>Ala Ser His Val Lys Ala Leu Val Tyr Ser Trp Thr His Arg Ser Ala<br>                  485                       490                       495 | 1488 |

```
gat cgt aca aat aca att gag cca aat agc att aca caa ata cca tta     1536
Asp Arg Thr Asn Thr Ile Glu Pro Asn Ser Ile Thr Gln Ile Pro Leu
        500                 505                 510 gta aaa gca ttc aat ctg tct tca ggt gcc gct gtt gtt aga gga cct     1584
Val Lys Ala Phe Asn Leu Ser Ser Gly Ala Ala Val Val Arg Gly Pro
        515                 520                 525 gga ttt aca ggt ggg gat atc ctc cga aga acg aat act ggt aca ttt     1632
Gly Phe Thr Gly Gly Asp Ile Leu Arg Arg Thr Asn Thr Gly Thr Phe
    530                 535                 540 ggg gat ata cga gta aac ata aat cca cca ttt gca caa agg tat cgc     1680
Gly Asp Ile Arg Val Asn Ile Asn Pro Pro Phe Ala Gln Arg Tyr Arg
545                 550                 555                 560 gta agg att cgt tat gca tct act acg gat tta caa ttc cat acg tca     1728
Val Arg Ile Arg Tyr Ala Ser Thr Thr Asp Leu Gln Phe His Thr Ser
                565                 570                 575 att aac gga aga gct att aat caa ggt aat ttt tca gca act atg aat     1776
Ile Asn Gly Arg Ala Ile Asn Gln Gly Asn Phe Ser Ala Thr Met Asn
            580                 585                 590 aga gga gag gac tta gaa tat aga acc ttt aga act gta ggc ttt act     1824
Arg Gly Glu Asp Leu Glu Tyr Arg Thr Phe Arg Thr Val Gly Phe Thr
        595                 600                 605 act cca ttt agc ttt tca gat gta caa agt aca ttt aca ata gga gct     1872
Thr Pro Phe Ser Phe Ser Asp Val Gln Ser Thr Phe Thr Ile Gly Ala
        610                 615                 620 tgg aac ttc tct tca ggt aac gac gtt tat ata gat cga att gaa ttt     1920
Trp Asn Phe Ser Ser Gly Asn Asp Val Tyr Ile Asp Arg Ile Glu Phe
625                 630                 635                 640 gtt ccg gta gaa gta cca tat gag gaa gag tat gat ttt gaa aaa gtg     1968
Val Pro Val Glu Val Pro Tyr Glu Glu Glu Tyr Asp Phe Glu Lys Val
                645                 650                 655 caa gag gag gtt act gca ctg ttt aca tct acg aat cca aga gaa tta     2016
Gln Glu Glu Val Thr Ala Leu Phe Thr Ser Thr Asn Pro Arg Glu Leu
            660                 665                 670 aaa aca gat gta acg gat tat cat att gac cag gta tca aat tta gta     2064
Lys Thr Asp Val Thr Asp Tyr His Ile Asp Gln Val Ser Asn Leu Val
        675                 680                 685 gag tct cta tca gat gaa ttc tat ctc gat gaa aag aga gaa tta ttc     2112
Glu Ser Leu Ser Asp Glu Phe Tyr Leu Asp Glu Lys Arg Glu Leu Phe
        690                 695                 700 gag ata gta aaa tac gta aag caa ctc aat att gag cgt gac atg         2157
Glu Ile Val Lys Tyr Val Lys Gln Leu Asn Ile Glu Arg Asp Met
705                 710                 715

<210> SEQ ID NO 2
<211> LENGTH: 719
<212> TYPE: PRT
<213> ORGANISM: Bacillus thuringiensis

<400> SEQUENCE: 2

Met Lys Ser Lys Asn Gln Asp Met Tyr Gln Arg Leu Ser Tyr Asn Thr
  1               5                  10                  15

Thr Val Asp Lys Asn Ser Thr Asp Ser Leu Arg Asn Glu Thr Asp Ile
                 20                  25                  30

Glu Leu Lys Asn Ile Asn His Glu Asp Phe Leu Arg Met Ser Glu His
             35                  40                  45

Glu Ser Ile Asp Pro Phe Val Asn Val Ser Thr Ile Gln Thr Gly Ile
         50                  55                  60

Gly Ile Ala Gly Lys Ile Leu Gly Thr Leu Gly Val Pro Phe Ala Gly
 65                  70                  75                  80
```

```
Gln Ile Ala Ser Leu Tyr Ser Phe Ile Leu Gly Glu Leu Trp Pro Lys
                 85                  90                  95

Gly Lys Ser Gln Trp Glu Ile Phe Met Glu His Val Glu Glu Leu Ile
            100                 105                 110

Asp Gln Lys Ile Ser Thr Tyr Ala Arg Asn Ile Ala Leu Ala Asp Leu
        115                 120                 125

Lys Gly Leu Gly Asp Ala Leu Ala Val Tyr His Glu Ser Leu Glu Ser
    130                 135                 140

Trp Ile Lys Asn Arg Asn Asn Ala Arg Ala Thr Ser Val Val Lys Ser
145                 150                 155                 160

Gln Tyr Ile Ala Leu Glu Leu Leu Phe Val Gln Lys Leu Pro Ser Phe
                165                 170                 175

Ala Val Ser Gly Glu Glu Val Pro Leu Leu Pro Ile Tyr Ala Gln Ala
            180                 185                 190

Ala Asn Leu His Leu Leu Leu Arg Asp Ala Ser Val Phe Gly Lys
        195                 200                 205

Glu Trp Gly Leu Ser Asn Ser Gln Ile Ser Thr Phe Tyr Asn Arg Gln
    210                 215                 220

Val Glu Arg Thr Ser Asp Tyr Ser Asp His Cys Val Lys Trp Tyr Ser
225                 230                 235                 240

Thr Gly Leu Asn Asn Leu Arg Gly Thr Asn Ala Glu Ser Trp Val Arg
                245                 250                 255

Tyr Asn Gln Phe Arg Lys Asp Met Thr Leu Met Val Leu Asp Leu Ile
            260                 265                 270

Ala Leu Phe Pro Ser Tyr Asp Thr Leu Val Tyr Pro Ile Lys Thr Thr
        275                 280                 285

Ser Gln Leu Thr Arg Glu Val Tyr Thr Asp Ala Ile Gly Thr Val His
    290                 295                 300

Pro Asn Ala Ser Phe Ala Ser Thr Thr Trp Tyr Asn Asn Ala Pro
305                 310                 315                 320

Ser Phe Ser Ala Ile Glu Ser Ala Val Val Arg Asn Pro His Leu Leu
                325                 330                 335

Asp Phe Leu Glu Gln Val Thr Ile Tyr Ser Leu Leu Ser Arg Trp Ser
            340                 345                 350

Asn Thr Gln Tyr Met Asn Met Trp Gly Gly His Arg Leu Glu Phe Arg
        355                 360                 365

Thr Ile Gly Gly Val Leu Asn Thr Ser Thr Gln Gly Ser Thr Asn Thr
    370                 375                 380

Ser Ile Asn Pro Val Thr Leu Pro Phe Thr Ser Arg Asp Val Tyr Arg
385                 390                 395                 400

Thr Glu Ser Leu Ala Gly Leu Asn Leu Phe Leu Thr Gln Pro Val Asn
                405                 410                 415

Gly Val Pro Arg Val Asp Phe His Trp Lys Phe Ala Thr Leu Pro Ile
            420                 425                 430

Ala Ser Asp Asn Phe Tyr Tyr Pro Gly Tyr Ala Gly Ile Gly Thr Gln
        435                 440                 445

Leu Gln Asp Ser Glu Asn Glu Leu Pro Pro Glu Thr Thr Gly Gln Pro
    450                 455                 460

Asn Tyr Glu Ser Tyr Ser His Arg Leu Ser His Ile Gly Leu Ile Ser
465                 470                 475                 480

Ala Ser His Val Lys Ala Leu Val Tyr Ser Trp Thr His Arg Ser Ala
                485                 490                 495

Asp Arg Thr Asn Thr Ile Glu Pro Asn Ser Ile Thr Gln Ile Pro Leu
            500                 505                 510
```

```
Val Lys Ala Phe Asn Leu Ser Ser Gly Ala Val Val Arg Gly Pro
        515                 520                 525
Gly Phe Thr Gly Gly Asp Ile Leu Arg Arg Thr Asn Thr Gly Thr Phe
        530                 535                 540
Gly Asp Ile Arg Val Asn Ile Asn Pro Pro Phe Ala Gln Arg Tyr Arg
545                 550                 555                 560
Val Arg Ile Arg Tyr Ala Ser Thr Thr Asp Leu Gln Phe His Thr Ser
                565                 570                 575
Ile Asn Gly Arg Ala Ile Asn Gln Gly Asn Phe Ser Ala Thr Met Asn
                580                 585                 590
Arg Gly Glu Asp Leu Glu Tyr Arg Thr Phe Arg Thr Val Gly Phe Thr
                595                 600                 605
Thr Pro Phe Ser Phe Ser Asp Val Gln Ser Thr Phe Thr Ile Gly Ala
        610                 615                 620
Trp Asn Phe Ser Ser Gly Asn Asp Val Tyr Ile Asp Arg Ile Glu Phe
625                 630                 635                 640
Val Pro Val Glu Val Pro Tyr Glu Glu Glu Tyr Asp Phe Glu Lys Val
                645                 650                 655
Gln Glu Glu Val Thr Ala Leu Phe Thr Ser Thr Asn Pro Arg Glu Leu
                660                 665                 670
Lys Thr Asp Val Thr Asp Tyr His Ile Asp Gln Val Ser Asn Leu Val
                675                 680                 685
Glu Ser Leu Ser Asp Glu Phe Tyr Leu Asp Glu Lys Arg Glu Leu Phe
        690                 695                 700
Glu Ile Val Lys Tyr Val Lys Gln Leu Asn Ile Glu Arg Asp Met
705                 710                 715

<210> SEQ ID NO 3
<211> LENGTH: 2136
<212> TYPE: DNA
<213> ORGANISM: Bacillus thuringiensis
<220> FEATURE:
<221> NAME/KEY: CDS
<222> LOCATION: (1)...(2136)

<400> SEQUENCE: 3 atg tat caa aga tta tct tac aat aca aca gtt gat aaa aac tct aca    48
Met Tyr Gln Arg Leu Ser Tyr Asn Thr Thr Val Asp Lys Asn Ser Thr
 1               5                  10                  15 gat tca cta aga aat gaa aca gat ata gaa ttg aaa aat att aat cat    96
Asp Ser Leu Arg Asn Glu Thr Asp Ile Glu Leu Lys Asn Ile Asn His
             20                  25                  30 gag gat ttc cta aga atg tct gag cat gag agt att gat cca ttt gtt   144
Glu Asp Phe Leu Arg Met Ser Glu His Glu Ser Ile Asp Pro Phe Val
         35                  40                  45 aat gtt tca aca att caa acg ggg att ggt att gct ggt aaa ata ctt   192
Asn Val Ser Thr Ile Gln Thr Gly Ile Gly Ile Ala Gly Lys Ile Leu
     50                  55                  60 ggt acc cta ggt gtt cct ttt gct gga caa ata gct agc ctc tat agt   240
Gly Thr Leu Gly Val Pro Phe Ala Gly Gln Ile Ala Ser Leu Tyr Ser
 65                  70                  75                  80 ttt atc tta ggc gag ctt tgg cct aaa ggg aaa agt caa tgg gaa atc   288
Phe Ile Leu Gly Glu Leu Trp Pro Lys Gly Lys Ser Gln Trp Glu Ile
                 85                  90                  95 ttt atg gaa cat gta gaa gag ctt att gac caa aaa ata tca act tac   336
Phe Met Glu His Val Glu Glu Leu Ile Asp Gln Lys Ile Ser Thr Tyr
            100                 105                 110 gca aga aac ata gca ctt gca gat tta aaa ggc tta gga gat gct ttg   384
```

```
                Ala Arg Asn Ile Ala Leu Ala Asp Leu Lys Gly Leu Gly Asp Ala Leu
                            115                 120                 125 gct gtc tac cat gaa tcg ctt gaa agt tgg att aaa aat cgc aac aac           432
Ala Val Tyr His Glu Ser Leu Glu Ser Trp Ile Lys Asn Arg Asn Asn
130                 135                 140 gca agg gct aca agt gtt gtc aag agc caa tat att gct tta gaa cta           480
Ala Arg Ala Thr Ser Val Val Lys Ser Gln Tyr Ile Ala Leu Glu Leu
145                 150                 155                 160 ttg ttt gtt caa aag ctg cct tct ttt gca gta tca ggt gag gaa gta           528
Leu Phe Val Gln Lys Leu Pro Ser Phe Ala Val Ser Gly Glu Glu Val
                165                 170                 175 cca tta ttg cca ata tat gca caa gct gca aat tta cac tta tta tta           576
Pro Leu Leu Pro Ile Tyr Ala Gln Ala Ala Asn Leu His Leu Leu Leu
                180                 185                 190 cta aga gat gct tct gtt ttt gga aaa gag tgg gga tta tct aat tcg           624
Leu Arg Asp Ala Ser Val Phe Gly Lys Glu Trp Gly Leu Ser Asn Ser
                195                 200                 205 caa att tct aca ttt tat aat cgt caa gtc gaa aga acg agt gac tat           672
Gln Ile Ser Thr Phe Tyr Asn Arg Gln Val Glu Arg Thr Ser Asp Tyr
210                 215                 220 tcc gac cat tgt gtg aaa tgg tat agt aca ggt cta aat aac ttg aga           720
Ser Asp His Cys Val Lys Trp Tyr Ser Thr Gly Leu Asn Asn Leu Arg
225                 230                 235                 240 ggt aca aat gcc gaa agc tgg gtc cgt tat aat caa ttt cgt aaa gat           768
Gly Thr Asn Ala Glu Ser Trp Val Arg Tyr Asn Gln Phe Arg Lys Asp
                245                 250                 255 atg aca tta atg gta cta gat tta atc gca tta ttc cca agc tat gat           816
Met Thr Leu Met Val Leu Asp Leu Ile Ala Leu Phe Pro Ser Tyr Asp
                260                 265                 270 aca ctt gta tat cca att aaa acc act tct caa ctt aca aga gaa gta           864
Thr Leu Val Tyr Pro Ile Lys Thr Thr Ser Gln Leu Thr Arg Glu Val
                275                 280                 285 tat aca gac gca att ggg aca gta cat cca aat gca agt ttt gca agt           912
Tyr Thr Asp Ala Ile Gly Thr Val His Pro Asn Ala Ser Phe Ala Ser
290                 295                 300 acg acc tgg tat aat aat aat gca cct tcg ttc tct gcc ata gag tct           960
Thr Thr Trp Tyr Asn Asn Asn Ala Pro Ser Phe Ser Ala Ile Glu Ser
305                 310                 315                 320 gct gtt gtt cga aac ccg cat cta ctc gat ttt tta gaa caa gtt aca          1008
Ala Val Val Arg Asn Pro His Leu Leu Asp Phe Leu Glu Gln Val Thr
                325                 330                 335 att tac agc tta tta agt agg tgg agt aac act cag tat atg aat atg          1056
Ile Tyr Ser Leu Leu Ser Arg Trp Ser Asn Thr Gln Tyr Met Asn Met
                340                 345                 350 tgg gga gga cat aga ctg gaa ttc cga aca ata ggt gga gtg tta aat          1104
Trp Gly Gly His Arg Leu Glu Phe Arg Thr Ile Gly Gly Val Leu Asn
                355                 360                 365 acc tca aca caa ggg tct act aat act tct att aat cct gta aca tta          1152
Thr Ser Thr Gln Gly Ser Thr Asn Thr Ser Ile Asn Pro Val Thr Leu
370                 375                 380 ccg ttc acg tct cga gac gtc tat agg act gaa tca ttg gca ggg ctg          1200
Pro Phe Thr Ser Arg Asp Val Tyr Arg Thr Glu Ser Leu Ala Gly Leu
385                 390                 395                 400 aat cta ttt tta act caa cct gtt aat gga gta cct agg gtt gat ttt          1248
Asn Leu Phe Leu Thr Gln Pro Val Asn Gly Val Pro Arg Val Asp Phe
                405                 410                 415 cat tgg aaa ttc gcc aca ctt ccg att gca tct gat aat ttc tat tat          1296
His Trp Lys Phe Ala Thr Leu Pro Ile Ala Ser Asp Asn Phe Tyr Tyr
                420                 425                 430 cca ggg tat gct gga att ggg acg caa tta caa gat tca gaa aat gaa          1344
```

```
                Pro Gly Tyr Ala Gly Ile Gly Thr Gln Leu Gln Asp Ser Glu Asn Glu
                        435                 440                 445 tta cct cct gaa aca aca gga cag cca aat tat gaa tca tat agt cat        1392
Leu Pro Pro Glu Thr Thr Gly Gln Pro Asn Tyr Glu Ser Tyr Ser His
450                 455                 460 aga tta tct cat ata gga ctc att tca gca tca cat gtg aaa gca ttg        1440
Arg Leu Ser His Ile Gly Leu Ile Ser Ala Ser His Val Lys Ala Leu
465                 470                 475                 480 gta tat tct tgg acg cat cgt agt gca gat cgt aca aat aca att gag        1488
Val Tyr Ser Trp Thr His Arg Ser Ala Asp Arg Thr Asn Thr Ile Glu
                485                 490                 495 cca aat agc att aca caa ata cca tta gta aaa gca ttc aat ctg tct        1536
Pro Asn Ser Ile Thr Gln Ile Pro Leu Val Lys Ala Phe Asn Leu Ser
            500                 505                 510 tca ggt gcc gct gtt gtt aga gga cct gga ttt aca ggt ggg gat atc        1584
Ser Gly Ala Ala Val Val Arg Gly Pro Gly Phe Thr Gly Gly Asp Ile
        515                 520                 525 ctc cga aga acg aat act ggt aca ttt ggg gat ata cga gta aac ata        1632
Leu Arg Arg Thr Asn Thr Gly Thr Phe Gly Asp Ile Arg Val Asn Ile
    530                 535                 540 aat cca cca ttt gca caa agg tat cgc gta agg att cgt tat gca tct        1680
Asn Pro Pro Phe Ala Gln Arg Tyr Arg Val Arg Ile Arg Tyr Ala Ser
545                 550                 555                 560 act acg gat tta caa ttc cat acg tca att aac gga aga gct att aat        1728
Thr Thr Asp Leu Gln Phe His Thr Ser Ile Asn Gly Arg Ala Ile Asn
                565                 570                 575 caa ggt aat ttt tca gca act atg aat aga gga gag gac tta gaa tat        1776
Gln Gly Asn Phe Ser Ala Thr Met Asn Arg Gly Glu Asp Leu Glu Tyr
            580                 585                 590 aga acc ttt aga act gta ggc ttt act act cca ttt agc ttt tca gat        1824
Arg Thr Phe Arg Thr Val Gly Phe Thr Thr Pro Phe Ser Phe Ser Asp
        595                 600                 605 gta caa agt aca ttt aca ata gga gct tgg aac ttc tct tca ggt aac        1872
Val Gln Ser Thr Phe Thr Ile Gly Ala Trp Asn Phe Ser Ser Gly Asn
    610                 615                 620 gac gtt tat ata gat cga att gaa ttt gtt ccg gta gaa gta cca tat        1920
Asp Val Tyr Ile Asp Arg Ile Glu Phe Val Pro Val Glu Val Pro Tyr
625                 630                 635                 640 gag gaa gag tat gat ttt gaa aaa gtg caa gag gag gtt act gca ctg        1968
Glu Glu Glu Tyr Asp Phe Glu Lys Val Gln Glu Glu Val Thr Ala Leu
                645                 650                 655 ttt aca tct acg aat cca aga gaa tta aaa aca gat gta acg gat tat        2016
Phe Thr Ser Thr Asn Pro Arg Glu Leu Lys Thr Asp Val Thr Asp Tyr
            660                 665                 670 cat att gac cag gta tca aat tta gta gag tct cta tca gat gaa ttc        2064
His Ile Asp Gln Val Ser Asn Leu Val Glu Ser Leu Ser Asp Glu Phe
        675                 680                 685 tat ctc gat gaa aag aga gaa tta ttc gag ata gta aaa tac gta aag        2112
Tyr Leu Asp Glu Lys Arg Glu Leu Phe Glu Ile Val Lys Tyr Val Lys
    690                 695                 700 caa ctc aat att gag cgt gac atg                                        2136
Gln Leu Asn Ile Glu Arg Asp Met
705                 710

<210> SEQ ID NO 4
<211> LENGTH: 712
<212> TYPE: PRT
<213> ORGANISM: Bacillus thuringiensis

<400> SEQUENCE: 4

Met Tyr Gln Arg Leu Ser Tyr Asn Thr Thr Val Asp Lys Asn Ser Thr
```

-continued

```
              1               5                  10                 15
        Asp Ser Leu Arg Asn Glu Thr Asp Ile Glu Leu Lys Asn Ile Asn His
                        20                 25                 30

Glu Asp Phe Leu Arg Met Ser Glu His Glu Ser Ile Asp Pro Phe Val
                        35                 40                 45

Asn Val Ser Thr Ile Gln Thr Gly Ile Gly Ile Ala Gly Lys Ile Leu
                    50                 55                 60

Gly Thr Leu Gly Val Pro Phe Ala Gly Gln Ile Ala Ser Leu Tyr Ser
         65                 70                 75                 80

Phe Ile Leu Gly Glu Leu Trp Pro Lys Gly Lys Ser Gln Trp Glu Ile
                        85                 90                 95

Phe Met Glu His Val Glu Glu Leu Ile Asp Gln Lys Ile Ser Thr Tyr
                       100                105                110

Ala Arg Asn Ile Ala Leu Ala Asp Leu Lys Gly Leu Gly Asp Ala Leu
                       115                120                125

Ala Val Tyr His Glu Ser Leu Glu Ser Trp Ile Lys Asn Arg Asn Asn
                       130                135                140

Ala Arg Ala Thr Ser Val Val Lys Ser Gln Tyr Ile Ala Leu Glu Leu
        145                150                155                160

Leu Phe Val Gln Lys Leu Pro Ser Phe Ala Val Ser Gly Glu Glu Val
                       165                170                175

Pro Leu Leu Pro Ile Tyr Ala Gln Ala Ala Asn Leu His Leu Leu Leu
                       180                185                190

Leu Arg Asp Ala Ser Val Phe Gly Lys Glu Trp Gly Leu Ser Asn Ser
                       195                200                205

Gln Ile Ser Thr Phe Tyr Asn Arg Gln Val Glu Arg Thr Ser Asp Tyr
                       210                215                220

Ser Asp His Cys Val Lys Trp Tyr Ser Thr Gly Leu Asn Asn Leu Arg
        225                230                235                240

Gly Thr Asn Ala Glu Ser Trp Val Arg Tyr Asn Gln Phe Arg Lys Asp
                       245                250                255

Met Thr Leu Met Val Leu Asp Leu Ile Ala Leu Phe Pro Ser Tyr Asp
                       260                265                270

Thr Leu Val Tyr Pro Ile Lys Thr Thr Ser Gln Leu Thr Arg Glu Val
                       275                280                285

Tyr Thr Asp Ala Ile Gly Thr Val His Pro Asn Ala Ser Phe Ala Ser
                       290                295                300

Thr Thr Trp Tyr Asn Asn Asn Ala Pro Ser Phe Ser Ala Ile Glu Ser
        305                310                315                320

Ala Val Val Arg Asn Pro His Leu Leu Asp Phe Leu Glu Gln Val Thr
                       325                330                335

Ile Tyr Ser Leu Leu Ser Arg Trp Ser Asn Thr Gln Tyr Met Asn Met
                       340                345                350

Trp Gly Gly His Arg Leu Glu Phe Arg Thr Ile Gly Gly Val Leu Asn
                       355                360                365

Thr Ser Thr Gln Gly Ser Thr Asn Thr Ser Ile Asn Pro Val Thr Leu
        370                375                380

Pro Phe Thr Ser Arg Asp Val Tyr Arg Thr Glu Ser Leu Ala Gly Leu
        385                390                395                400

Asn Leu Phe Leu Thr Gln Pro Val Asn Gly Val Pro Arg Val Asp Phe
                       405                410                415

His Trp Lys Phe Ala Thr Leu Pro Ile Ala Ser Asp Asn Phe Tyr Tyr
                       420                425                430
```

```
Pro Gly Tyr Ala Gly Ile Gly Thr Gln Leu Gln Asp Ser Glu Asn Glu
            435                 440                 445

Leu Pro Pro Glu Thr Thr Gly Gln Pro Asn Tyr Glu Ser Tyr Ser His
    450                 455                 460

Arg Leu Ser His Ile Gly Leu Ile Ser Ala Ser His Val Lys Ala Leu
465                 470                 475                 480

Val Tyr Ser Trp Thr His Arg Ser Ala Asp Arg Thr Asn Thr Ile Glu
                485                 490                 495

Pro Asn Ser Ile Thr Gln Ile Pro Leu Val Lys Ala Phe Asn Leu Ser
                500                 505                 510

Ser Gly Ala Ala Val Val Arg Gly Pro Gly Phe Thr Gly Gly Asp Ile
            515                 520                 525

Leu Arg Arg Thr Asn Thr Gly Thr Phe Gly Asp Ile Arg Val Asn Ile
530                 535                 540

Asn Pro Pro Phe Ala Gln Arg Tyr Arg Val Arg Ile Arg Tyr Ala Ser
545                 550                 555                 560

Thr Thr Asp Leu Gln Phe His Thr Ser Ile Asn Gly Arg Ala Ile Asn
                565                 570                 575

Gln Gly Asn Phe Ser Ala Thr Met Asn Arg Gly Glu Asp Leu Glu Tyr
            580                 585                 590

Arg Thr Phe Arg Thr Val Gly Phe Thr Thr Pro Phe Ser Phe Ser Asp
            595                 600                 605

Val Gln Ser Thr Phe Thr Ile Gly Ala Trp Asn Phe Ser Ser Gly Asn
610                 615                 620

Asp Val Tyr Ile Asp Arg Ile Glu Phe Val Pro Val Glu Val Pro Tyr
625                 630                 635                 640

Glu Glu Glu Tyr Asp Phe Glu Lys Val Gln Glu Val Thr Ala Leu
                645                 650                 655

Phe Thr Ser Thr Asn Pro Arg Glu Leu Lys Thr Asp Val Thr Asp Tyr
                660                 665                 670

His Ile Asp Gln Val Ser Asn Leu Val Glu Ser Leu Ser Asp Glu Phe
                675                 680                 685

Tyr Leu Asp Glu Lys Arg Glu Leu Phe Glu Ile Val Lys Tyr Val Lys
            690                 695                 700

Gln Leu Asn Ile Glu Arg Asp Met
705                 710

<210> SEQ ID NO 5
<211> LENGTH: 1176
<212> TYPE: PRT
<213> ORGANISM: Bacillus thuringiensis

<400> SEQUENCE: 5

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Pro Val Gln Ile
65                  70                  75                  80

Glu Gln Leu Ile Asn Gln Arg Ile Glu Glu Phe Ala Arg Asn Gln Ala
                85                  90                  95
```

```
Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
        130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Gln Asn Ile Arg Gln Pro His Leu Met Asp Ile Leu Asn Ser Ile Thr
290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Pro Val Leu Val Ser Leu
            340                 345                 350

Thr Gly Leu Gly Ile Phe Arg Thr Leu Ser Ser Pro Leu Tyr Arg Arg
        355                 360                 365

Ile Ile Leu Gly Ser Gly Pro Asn Asn Gln Glu Leu Phe Val Leu Asp
370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
                405                 410                 415

Gln Asp Asn Ser Val Pro Pro Arg Ala Gly Phe Ser His Arg Leu Ser
            420                 425                 430

His Val Thr Met Leu Ser Gln Ala Ala Gly Ala Val Tyr Thr Leu Arg
        435                 440                 445

Ala Pro Thr Phe Ser Trp Gln His Arg Ser Ala Glu Phe Asn Asn Ile
450                 455                 460

Ile Pro Ser Ser Gln Ile Thr Gln Ile Pro Leu Thr Lys Ser Thr Asn
465                 470                 475                 480

Leu Gly Ser Gly Thr Ser Val Val Lys Gly Pro Gly Phe Thr Gly Gly
                485                 490                 495

Asp Ile Leu Arg Arg Thr Ser Pro Gly Gln Ile Ser Thr Leu Arg Val
            500                 505                 510

Asn Ile Thr Ala Pro Leu Ser Gln Arg Tyr Arg Val Arg Ile Arg Tyr
        515                 520                 525
```

```
Ala Ser Thr Thr Asn Leu Gln Phe His Thr Ser Ile Asp Gly Arg Pro
    530                 535                 540

Ile Asn Gln Gly Asn Phe Ser Ala Thr Met Ser Ser Gly Ser Asn Leu
545                 550                 555                 560

Gln Ser Gly Ser Phe Arg Thr Val Gly Phe Thr Thr Pro Phe Asn Phe
                565                 570                 575

Ser Asn Gly Ser Ser Val Phe Thr Leu Ser Ala His Val Phe Asn Ser
            580                 585                 590

Gly Asn Glu Val Tyr Ile Asp Arg Ile Glu Phe Val Pro Ala Glu Val
        595                 600                 605

Thr Phe Glu Ala Glu Tyr Asp Leu Glu Arg Ala Gln Lys Ala Val Asn
    610                 615                 620

Glu Leu Phe Thr Ser Ser Asn Gln Ile Gly Leu Lys Thr Asp Val Thr
625                 630                 635                 640

Asp Tyr His Ile Asp Gln Val Ser Asn Leu Val Glu Cys Leu Ser Asp
                645                 650                 655

Glu Phe Cys Leu Asp Glu Lys Gln Glu Leu Ser Glu Lys Val Lys His
            660                 665                 670

Ala Lys Arg Leu Ser Asp Glu Arg Asn Leu Leu Gln Asp Pro Asn Phe
        675                 680                 685

Arg Gly Ile Asn Arg Gln Leu Asp Arg Gly Trp Arg Gly Ser Thr Asp
    690                 695                 700

Ile Thr Ile Gln Gly Gly Asp Asp Val Phe Lys Glu Asn Tyr Val Thr
705                 710                 715                 720

Leu Leu Gly Thr Phe Asp Glu Cys Tyr Pro Thr Tyr Leu Tyr Gln Lys
                725                 730                 735

Ile Asp Glu Ser Lys Leu Lys Ala Tyr Thr Arg Tyr Gln Leu Arg Gly
            740                 745                 750

Tyr Ile Glu Asp Ser Gln Asp Leu Glu Ile Tyr Leu Ile Arg Tyr Asn
        755                 760                 765

Ala Lys His Glu Thr Val Asn Val Pro Gly Thr Gly Ser Leu Trp Pro
    770                 775                 780

Leu Ser Ala Gln Ser Pro Ile Gly Lys Cys Gly Glu Pro Asn Arg Cys
785                 790                 795                 800

Ala Pro His Leu Glu Trp Asn Pro Asp Leu Asp Cys Ser Cys Arg Asp
                805                 810                 815

Gly Glu Lys Cys Ala His His Ser His His Phe Ser Leu Asp Ile Asp
            820                 825                 830

Val Gly Cys Thr Asp Leu Asn Glu Asp Leu Gly Val Trp Val Ile Phe
        835                 840                 845

Lys Ile Lys Thr Gln Asp Gly His Ala Arg Leu Gly Asn Leu Glu Phe
    850                 855                 860

Leu Glu Glu Lys Pro Leu Val Gly Glu Ala Leu Ala Arg Val Lys Arg
865                 870                 875                 880

Ala Glu Lys Lys Trp Arg Asp Lys Arg Glu Lys Leu Glu Trp Glu Thr
                885                 890                 895

Asn Ile Val Tyr Lys Glu Ala Lys Glu Ser Val Asp Ala Leu Phe Val
            900                 905                 910

Asn Ser Gln Tyr Asp Gln Leu Gln Ala Asp Thr Asn Ile Ala Met Ile
        915                 920                 925

His Ala Ala Asp Lys Arg Val His Ser Ile Arg Glu Ala Tyr Leu Pro
    930                 935                 940

Glu Leu Ser Val Ile Pro Gly Val Asn Ala Ala Ile Phe Glu Glu Leu
```

```
                945                 950                 955                 960
Glu Gly Arg Ile Phe Thr Ala Phe Ser Leu Tyr Asp Ala Arg Asn Val
                    965                 970                 975
Ile Lys Asn Gly Asp Phe Asn Asn Gly Leu Ser Cys Trp Asn Val Lys
                980                 985                 990
Gly His Val Asp Val Glu Glu Gln Asn Asn Gln Arg Ser Val Leu Val
            995                1000                1005
Val Pro Glu Trp Glu Ala Glu Val Ser Gln Val Arg Val Cys Pro
        1010                1015                1020
Gly Arg Gly Tyr Ile Leu Arg Val Thr Ala Tyr Lys Glu Gly Tyr Gly
1025                1030                1035                1040
Glu Gly Cys Val Thr Ile His Glu Ile Glu Asn Asn Thr Asp Glu Leu
                1045                1050                1055
Lys Phe Ser Asn Cys Val Glu Glu Ile Tyr Pro Asn Asn Thr Val
                1060                1065                1070
Thr Cys Asn Asp Tyr Thr Val Asn Gln Glu Glu Tyr Gly Gly Ala Tyr
                1075                1080                1085
Thr Ser Arg Asn Arg Gly Tyr Asn Glu Ala Pro Ser Val Pro Ala Asp
            1090                1095                1100
Tyr Ala Ser Val Tyr Glu Glu Lys Ser Tyr Thr Asp Gly Arg Arg Glu
1105                1110                1115                1120
Asn Pro Cys Glu Phe Asn Arg Gly Tyr Arg Asp Tyr Thr Pro Leu Pro
                1125                1130                1135
Val Gly Tyr Val Thr Lys Glu Leu Glu Tyr Phe Pro Glu Thr Asp Lys
            1140                1145                1150
Val Trp Ile Glu Ile Gly Glu Thr Glu Gly Thr Phe Ile Val Asp Ser
        1155                1160                1165
Val Glu Leu Leu Leu Met Glu Glu
        1170                1175

<210> SEQ ID NO 6
<211> LENGTH: 1155
<212> TYPE: PRT
<213> ORGANISM: Bacillus thuringiensis serovar aizawai

<400> SEQUENCE: 6

Met Asp Asn Asn Pro Asn Ile Asn Glu Cys Ile Pro Tyr Asn Cys Leu
1               5                   10                  15
Ser Asn Pro Glu Val Glu Val Leu Gly Gly Glu Arg Ile Glu Thr Gly
            20                  25                  30
Tyr Thr Pro Ile Asp Ile Ser Leu Ser Leu Thr Gln Phe Leu Leu Ser
        35                  40                  45
Glu Phe Val Pro Gly Ala Gly Phe Val Leu Gly Leu Val Asp Ile Ile
    50                  55                  60
Trp Gly Ile Phe Gly Pro Ser Gln Trp Asp Ala Phe Leu Val Gln Ile
65                  70                  75                  80
Glu Gln Leu Ile Asn Gln Arg Ile Glu Glu Phe Ala Arg Asn Gln Ala
                85                  90                  95
Ile Ser Arg Leu Glu Gly Leu Ser Asn Leu Tyr Gln Ile Tyr Ala Glu
            100                 105                 110
Ser Phe Arg Glu Trp Glu Ala Asp Pro Thr Asn Pro Ala Leu Arg Glu
        115                 120                 125
Glu Met Arg Ile Gln Phe Asn Asp Met Asn Ser Ala Leu Thr Thr Ala
    130                 135                 140
Ile Pro Leu Phe Ala Val Gln Asn Tyr Gln Val Pro Leu Leu Ser Val
```

```
                145                 150                 155                 160
            Tyr Val Gln Ala Ala Asn Leu His Leu Ser Val Leu Arg Asp Val Ser
                            165                 170                 175
            Val Phe Gly Gln Arg Trp Gly Phe Asp Ala Ala Thr Ile Asn Ser Arg
                        180                 185                 190
            Tyr Asn Asp Leu Thr Arg Leu Ile Gly Asn Tyr Thr Asp His Ala Val
                        195                 200                 205
            Arg Trp Tyr Asn Thr Gly Leu Glu Arg Val Trp Gly Pro Asp Ser Arg
                    210                 215                 220
            Asp Trp Ile Arg Tyr Asn Gln Phe Arg Arg Glu Leu Thr Leu Thr Val
            225                 230                 235                 240
            Leu Asp Ile Val Ser Leu Phe Pro Asn Tyr Asp Ser Arg Thr Tyr Pro
                            245                 250                 255
            Ile Arg Thr Val Ser Gln Leu Thr Arg Glu Ile Tyr Thr Asn Pro Val
                        260                 265                 270
            Leu Glu Asn Phe Asp Gly Ser Phe Arg Gly Ser Ala Gln Gly Ile Glu
                    275                 280                 285
            Gly Ser Ile Arg Ser Pro His Leu Met Asp Ile Leu Asn Ser Ile Thr
                290                 295                 300
            Ile Tyr Thr Asp Ala His Arg Gly Glu Tyr Tyr Trp Ser Gly His Gln
            305                 310                 315                 320
            Ile Met Ala Ser Pro Val Gly Phe Ser Gly Pro Glu Phe Thr Phe Pro
                            325                 330                 335
            Leu Tyr Gly Thr Met Gly Asn Ala Ala Pro Gln Gln Arg Ile Val Ala
                        340                 345                 350
            Gln Leu Gly Gln Gly Val Tyr Arg Thr Leu Ser Ser Thr Leu Tyr Arg
                    355                 360                 365
            Arg Pro Phe Asn Ile Gly Ile Asn Asn Gln Gln Leu Ser Val Leu Asp
                370                 375                 380
            Gly Thr Glu Phe Ala Tyr Gly Thr Ser Ser Asn Leu Pro Ser Ala Val
            385                 390                 395                 400
            Tyr Arg Lys Ser Gly Thr Val Asp Ser Leu Asp Glu Ile Pro Pro Gln
                            405                 410                 415
            Asn Asn Asn Val Pro Pro Arg Gln Gly Phe Ser His Arg Leu Ser His
                        420                 425                 430
            Val Ser Met Phe Arg Ser Gly Phe Ser Asn Ser Ser Val Ser Ile Ile
                    435                 440                 445
            Arg Ala Pro Met Phe Ser Trp Ile His Arg Ser Ala Glu Phe Asn Asn
                450                 455                 460
            Ile Ile Pro Ser Ser Gln Ile Thr Gln Ile Pro Leu Thr Lys Ser Thr
            465                 470                 475                 480
            Asn Leu Gly Ser Gly Thr Ser Val Val Lys Gly Pro Gly Phe Thr Gly
                            485                 490                 495
            Gly Asp Ile Leu Arg Arg Thr Ser Pro Gly Gln Ile Ser Thr Leu Arg
                        500                 505                 510
            Val Asn Ile Thr Ala Pro Leu Ser Gln Arg Tyr Arg Val Arg Ile Arg
                    515                 520                 525
            Tyr Ala Ser Thr Thr Asn Leu Gln Phe His Thr Ser Ile Asp Gly Arg
                530                 535                 540
            Pro Ile Asn Gln Gly Asn Phe Ser Ala Thr Met Ser Ser Gly Ser Asn
            545                 550                 555                 560
            Leu Gln Ser Gly Ser Phe Arg Thr Val Gly Phe Thr Thr Pro Phe Asn
                            565                 570                 575
```

```
Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
        595                 600                 605

Val Thr Phe Glu Ala Glu Tyr Asp Leu Glu Arg Ala Gln Lys Ala Val
610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
                645                 650                 655

Asp Glu Phe Cys Leu Asp Glu Lys Lys Glu Leu Ser Glu Lys Val Lys
            660                 665                 670

His Ala Lys Arg Leu Ser Asp Glu Arg Asn Leu Leu Gln Asp Pro Asn
        675                 680                 685

Phe Arg Gly Ile Asn Arg Gln Leu Asp Arg Gly Trp Arg Gly Ser Thr
690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Pro Thr Tyr Leu Tyr Gln
                725                 730                 735

Lys Ile Asp Glu Ser Lys Leu Lys Ala Tyr Thr Arg Tyr Gln Leu Arg
            740                 745                 750

Gly Tyr Ile Glu Asp Ser Gln Asp Leu Glu Ile Tyr Leu Ile Arg Tyr
        755                 760                 765

Asn Ala Lys His Glu Thr Val Asn Val Pro Gly Thr Gly Ser Leu Trp
770                 775                 780

Pro Leu Ser Ala Pro Ser Pro Ile Gly Lys Cys Ala His His Ser His
785                 790                 795                 800

His Phe Ser Leu Asp Ile Asp Val Gly Cys Thr Asp Leu Asn Glu Asp
                805                 810                 815

Leu Gly Val Trp Val Ile Phe Lys Ile Lys Thr Gln Asp Gly His Ala
            820                 825                 830

Arg Leu Gly Asn Leu Glu Phe Leu Glu Glu Lys Pro Leu Val Gly Glu
        835                 840                 845

Ala Leu Ala Arg Val Lys Arg Ala Glu Lys Lys Trp Arg Asp Lys Arg
850                 855                 860

Glu Lys Leu Glu Trp Glu Thr Asn Ile Val Tyr Lys Glu Ala Lys Glu
865                 870                 875                 880

Ser Val Asp Ala Leu Phe Val Asn Ser Gln Tyr Asp Arg Leu Gln Ala
                885                 890                 895

Asp Thr Asn Ile Ala Met Ile His Ala Ala Asp Lys Arg Val His Ser
            900                 905                 910

Ile Arg Glu Ala Tyr Leu Pro Glu Leu Ser Val Ile Pro Gly Val Asn
        915                 920                 925

Ala Ala Ile Phe Glu Glu Leu Glu Gly Arg Ile Phe Thr Ala Phe Ser
930                 935                 940

Leu Tyr Asp Ala Arg Asn Val Ile Lys Asn Gly Asp Phe Asn Asn Gly
945                 950                 955                 960

Leu Ser Cys Trp Asn Val Lys Gly His Val Asp Val Glu Glu Gln Asn
                965                 970                 975

Asn His Arg Ser Val Leu Val Val Pro Glu Trp Glu Ala Glu Val Ser
            980                 985                 990

Gln Glu Val Arg Val Cys Pro Gly Arg Gly Tyr Ile Leu Arg Val Thr
        995                 1000                1005
```

```
Ala Tyr Lys Glu Gly Tyr Gly Glu Gly Cys Val Thr Ile His Glu Ile
        1010                1015                1020

Glu Asn Asn Thr Asp Glu Leu Lys Phe Ser Asn Cys Val Glu Glu Glu
1025                1030                1035                1040

Val Tyr Pro Asn Asn Thr Val Thr Cys Asn Asp Tyr Thr Ala Thr Gln
                1045                1050                1055

Glu Glu Tyr Glu Gly Thr Tyr Thr Ser Arg Asn Arg Gly Tyr Asp Gly
        1060                1065                1070

Ala Tyr Glu Ser Asn Ser Ser Val Pro Ala Asp Tyr Ala Ser Ala Tyr
        1075                1080                1085

Glu Glu Lys Ala Tyr Thr Asp Gly Arg Arg Asp Asn Pro Cys Glu Ser
        1090                1095                1100

Asn Arg Gly Tyr Gly Asp Tyr Thr Pro Leu Pro Ala Gly Tyr Val Thr
1105                1110                1115                1120

Lys Glu Leu Glu Tyr Phe Pro Glu Thr Asp Lys Val Trp Ile Glu Ile
                1125                1130                1135

Gly Glu Thr Glu Gly Thr Phe Ile Val Asp Ser Val Glu Leu Leu Leu
        1140                1145                1150

Met Glu Glu
        1155

<210> SEQ ID NO 7
<211> LENGTH: 1178
<212> TYPE: PRT
<213> ORGANISM: Bacillus thuringiensis

<400> SEQUENCE: 7

Met Asp Asn Asn Pro Asn Ile Asn Glu Cys Ile Pro Tyr Asn Cys Leu
 1               5                   10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220
```

```
Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
                260                 265                 270

Leu Glu Asn Phe Asp Gly Ser Phe Arg Gly Ser Ala Gln Gly Ile Glu
            275                 280                 285

Arg Ser Ile Arg Ser Pro His Leu Met Asp Ile Leu Asn Ser Ile Thr
        290                 295                 300

Ile Tyr Thr Asp Ala His Arg Gly Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
        515                 520                 525

Val Arg Val Arg Tyr Ala Ser Val Thr Pro Ile His Leu Asn Val Asn
    530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
        595                 600                 605

Thr Ala Thr Leu Glu Ala Glu Tyr Asn Leu Glu Arg Ala Gln Lys Ala
    610                 615                 620

Val Asn Ala Leu Phe Thr Ser Thr Asn Gln Leu Gly Leu Lys Thr Asn
625                 630                 635                 640

Val Thr Asp Tyr His Ile Asp Gln Val Ser Asn Leu Val Thr Tyr Leu
```

-continued

```
                645                 650                 655
Ser Asp Glu Phe Cys Leu Asp Glu Lys Arg Glu Leu Ser Glu Lys Val
            660                 665                 670

Lys His Ala Lys Arg Leu Ser Asp Glu Arg Asn Leu Leu Gln Asp Ser
            675                 680                 685

Asn Phe Lys Asp Ile Asn Arg Gln Pro Glu Arg Gly Trp Gly Gly Ser
            690                 695                 700

Thr Gly Ile Thr Ile Gln Gly Gly Asp Val Phe Lys Glu Asn Tyr
705                 710                 715                 720

Val Thr Leu Ser Gly Thr Phe Asp Glu Cys Tyr Pro Thr Tyr Leu Tyr
                725                 730                 735

Gln Lys Ile Asp Glu Ser Lys Leu Lys Ala Phe Thr Arg Tyr Gln Leu
            740                 745                 750

Arg Gly Tyr Ile Glu Asp Ser Gln Asp Leu Glu Ile Tyr Leu Ile Arg
            755                 760                 765

Tyr Asn Ala Lys His Glu Thr Val Asn Val Pro Gly Thr Gly Ser Leu
            770                 775                 780

Trp Pro Leu Ser Ala Gln Ser Pro Ile Gly Lys Cys Gly Glu Pro Asn
785                 790                 795                 800

Arg Cys Ala Pro His Leu Glu Trp Asn Pro Asp Leu Asp Cys Ser Cys
                805                 810                 815

Arg Asp Gly Glu Lys Cys Ala His His Ser His Phe Ser Leu Asp
            820                 825                 830

Ile Asp Val Gly Cys Thr Asp Leu Asn Glu Asp Leu Gly Val Trp Val
            835                 840                 845

Ile Phe Lys Ile Lys Thr Gln Asp Gly His Ala Arg Leu Gly Asn Leu
850                 855                 860

Glu Phe Leu Glu Glu Lys Pro Leu Val Gly Glu Ala Leu Ala Arg Val
865                 870                 875                 880

Lys Arg Ala Glu Lys Lys Trp Arg Asp Lys Arg Glu Lys Leu Glu Trp
            885                 890                 895

Glu Thr Asn Ile Val Tyr Lys Glu Ala Lys Glu Ser Val Asp Ala Leu
            900                 905                 910

Phe Val Asn Ser Gln Tyr Asp Gln Leu Gln Ala Asp Thr Asn Ile Ala
            915                 920                 925

Met Ile His Ala Ala Asp Lys Arg Val His Ser Ile Arg Glu Ala Tyr
            930                 935                 940

Leu Pro Glu Leu Ser Val Ile Pro Gly Val Asn Ala Ala Ile Phe Glu
945                 950                 955                 960

Glu Leu Glu Gly Arg Ile Phe Thr Ala Phe Ser Leu Tyr Asp Ala Arg
                965                 970                 975

Asn Val Ile Lys Asn Gly Asp Phe Asn Asn Gly Leu Ser Cys Trp Asn
            980                 985                 990

Val Lys Gly His Val Asp Val Glu Glu Gln Asn Asn Gln Arg Ser Val
            995                1000                1005

Leu Val Val Pro Glu Trp Glu Ala Glu Val Ser Gln Glu Val Arg Val
        1010                1015                1020

Cys Pro Gly Arg Gly Tyr Ile Leu Arg Val Thr Ala Tyr Lys Glu Gly
1025                1030                1035                1040

Tyr Gly Glu Gly Cys Val Thr Ile His Glu Ile Glu Asn Asn Thr Asp
                1045                1050                1055

Glu Leu Lys Phe Ser Asn Cys Val Glu Glu Glu Ile Tyr Pro Asn Asn
            1060                1065                1070
```

```
Thr Val Thr Cys Asn Asp Tyr Thr Val Asn Gln Glu Glu Tyr Gly Gly
        1075                1080                1085

Ala Tyr Thr Ser Arg Asn Arg Gly Tyr Asn Glu Ala Pro Ser Val Pro
    1090                1095                1100

Ala Asp Tyr Ala Ser Val Tyr Glu Glu Lys Ser Tyr Thr Asp Gly Arg
1105                1110                1115                1120

Arg Glu Asn Pro Cys Glu Phe Asn Arg Gly Tyr Arg Asp Tyr Thr Pro
            1125                1130                1135

Leu Pro Val Gly Tyr Val Thr Lys Glu Leu Gly Tyr Phe Pro Glu Thr
                1140                1145                1150

Asp Lys Val Trp Ile Glu Ile Gly Glu Thr Gly Thr Phe Ile Val
        1155                1160                1165

Asp Ser Val Glu Leu Leu Leu Met Glu Glu
        1170                1175

<210> SEQ ID NO 8
<211> LENGTH: 1228
<212> TYPE: PRT
<213> ORGANISM: Bacillus thuringiensis serovar entomocidus

<400> SEQUENCE: 8

Met Thr Ser Asn Arg Lys Asn Glu Asn Glu Ile Ile Asn Ala Val Ser
1               5                   10                  15

Asn His Ser Ala Gln Met Asp Leu Leu Pro Asp Ala Arg Ile Glu Asp
                20                  25                  30

Ser Leu Cys Ile Ala Glu Gly Asn Asn Ile Asp Pro Phe Val Ser Ala
            35                  40                  45

Ser Thr Val Gln Thr Gly Ile Asn Ile Ala Gly Arg Ile Leu Gly Val
        50                  55                  60

Leu Gly Val Pro Phe Ala Gly Gln Leu Ala Ser Phe Tyr Ser Phe Leu
65                  70                  75                  80

Val Gly Glu Leu Trp Pro Arg Gly Arg Asp Gln Trp Glu Ile Phe Leu
                85                  90                  95

Glu His Val Glu Gln Leu Ile Asn Gln Gln Ile Thr Glu Asn Ala Arg
            100                 105                 110

Asn Thr Ala Leu Ala Arg Leu Gln Gly Leu Gly Asp Ser Phe Arg Ala
        115                 120                 125

Tyr Gln Gln Ser Leu Glu Asp Trp Leu Glu Asn Arg Asp Asp Ala Arg
    130                 135                 140

Thr Arg Ser Val Leu Tyr Thr Gln Tyr Ile Ala Leu Glu Leu Asp Phe
145                 150                 155                 160

Leu Asn Ala Met Pro Leu Phe Ala Ile Arg Asn Gln Glu Val Pro Leu
                165                 170                 175

Leu Met Val Tyr Ala Gln Ala Ala Asn Leu His Leu Leu Leu Leu Arg
            180                 185                 190

Asp Ala Ser Leu Phe Gly Ser Glu Phe Gly Leu Thr Ser Gln Glu Ile
        195                 200                 205

Gln Arg Tyr Tyr Glu Arg Gln Val Glu Arg Thr Arg Asp Tyr Ser Asp
    210                 215                 220

Tyr Cys Val Glu Trp Tyr Asn Thr Gly Leu Asn Ser Leu Arg Gly Thr
225                 230                 235                 240

Asn Ala Ala Ser Trp Val Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270
```

-continued

```
Thr Tyr Pro Ile Asn Thr Ser Ala Gln Leu Thr Arg Glu Val Tyr Thr
        275                 280                 285

Asp Ala Ile Gly Ala Thr Gly Val Asn Met Ala Ser Met Asn Trp Tyr
        290                 295                 300

Asn Asn Asn Ala Pro Ser Phe Ser Ala Ile Glu Ala Ala Ile Arg
305                 310                 315                 320

Ser Pro His Leu Leu Asp Phe Leu Glu Gln Leu Thr Ile Phe Ser Ala
                325                 330                 335

Ser Ser Arg Trp Ser Asn Thr Arg His Met Thr Tyr Trp Arg Gly His
                340                 345                 350

Thr Ile Gln Ser Arg Pro Ile Gly Gly Leu Asn Thr Ser His
                355                 360                 365

Gly Ala Thr Asn Thr Ser Ile Asn Pro Val Thr Leu Arg Phe Ala Ser
        370                 375                 380

Arg Asp Val Tyr Arg Thr Glu Ser Tyr Ala Gly Val Leu Leu Trp Gly
385                 390                 395                 400

Ile Tyr Leu Glu Pro Ile His Gly Val Pro Thr Val Arg Phe Asn Phe
                405                 410                 415

Thr Asn Pro Gln Asn Ile Ser Asp Arg Gly Thr Ala Asn Tyr Ser Gln
                420                 425                 430

Pro Tyr Glu Ser Pro Gly Leu Gln Leu Lys Asp Ser Glu Thr Glu Leu
                435                 440                 445

Pro Pro Glu Thr Thr Glu Arg Pro Asn Tyr Glu Ser Tyr Ser His Arg
        450                 455                 460

Leu Ser His Ile Gly Ile Ile Leu Gln Ser Arg Val Asn Val Pro Val
465                 470                 475                 480

Tyr Ser Trp Thr His Arg Ser Ala Asp Arg Thr Asn Thr Ile Gly Pro
                485                 490                 495

Asn Arg Ile Thr Gln Ile Pro Met Val Lys Ala Ser Glu Leu Pro Gln
                500                 505                 510

Gly Thr Thr Val Val Arg Gly Pro Gly Phe Thr Gly Gly Asp Ile Leu
        515                 520                 525

Arg Arg Thr Asn Thr Gly Gly Phe Gly Pro Ile Arg Val Thr Val Asn
530                 535                 540

Gly Pro Leu Thr Gln Arg Tyr Arg Ile Gly Phe Arg Tyr Ala Ser Thr
545                 550                 555                 560

Val Asp Phe Asp Phe Phe Val Ser Arg Gly Gly Thr Val Asn Asn
                565                 570                 575

Phe Arg Phe Leu Arg Thr Met Asn Ser Gly Asp Glu Leu Lys Tyr Gly
                580                 585                 590

Asn Phe Val Arg Arg Ala Phe Thr Thr Pro Phe Thr Phe Thr Gln Ile
        595                 600                 605

Gln Asp Ile Ile Arg Thr Ser Ile Gln Gly Leu Ser Gly Asn Gly Glu
        610                 615                 620

Val Tyr Ile Asp Lys Ile Glu Ile Pro Val Thr Ala Thr Phe Glu
625                 630                 635                 640

Ala Glu Tyr Asp Leu Glu Arg Ala Gln Glu Ala Val Asn Ala Leu Phe
                645                 650                 655

Thr Asn Thr Asn Pro Arg Arg Leu Lys Thr Asp Val Thr Asp Tyr His
                660                 665                 670

Ile Asp Gln Val Ser Asn Leu Val Ala Cys Leu Ser Asp Glu Phe Cys
        675                 680                 685

Leu Asp Glu Lys Arg Glu Leu Leu Glu Lys Val Lys Tyr Ala Lys Arg
        690                 695                 700
```

```
Leu Ser Asp Glu Arg Asn Leu Leu Gln Asp Pro Asn Phe Thr Ser Ile
705                 710                 715                 720

Asn Lys Gln Pro Asp Phe Ile Ser Thr Asn Glu Gln Ser Asn Phe Thr
                725                 730                 735

Ser Ile His Glu Gln Ser Glu His Gly Trp Trp Gly Ser Glu Asn Ile
            740                 745                 750

Thr Ile Gln Glu Gly Asn Asp Val Phe Lys Glu Asn Tyr Val Thr Leu
        755                 760                 765

Pro Gly Thr Phe Asn Glu Cys Tyr Pro Thr Tyr Leu Tyr Gln Lys Ile
    770                 775                 780

Gly Glu Ser Glu Leu Lys Ala Tyr Thr Arg Tyr Gln Leu Arg Gly Tyr
785                 790                 795                 800

Ile Glu Asp Ser Gln Asp Leu Glu Ile Tyr Leu Ile Arg Tyr Asn Ala
                805                 810                 815

Lys His Glu Thr Leu Asp Val Pro Gly Thr Glu Ser Leu Trp Pro Leu
            820                 825                 830

Ser Val Glu Ser Pro Ile Gly Arg Cys Gly Glu Pro Asn Arg Cys Ala
        835                 840                 845

Pro His Phe Glu Trp Asn Pro Asp Leu Asp Cys Ser Cys Arg Asp Gly
    850                 855                 860

Glu Lys Cys Ala His His Ser His His Phe Ser Leu Asp Ile Asp Val
865                 870                 875                 880

Gly Cys Thr Asp Leu His Glu Asn Leu Gly Val Trp Val Val Phe Lys
                885                 890                 895

Ile Lys Thr Gln Glu Gly His Ala Arg Leu Gly Asn Leu Glu Phe Ile
            900                 905                 910

Glu Glu Lys Pro Leu Leu Gly Glu Ala Leu Ser Arg Val Lys Arg Ala
        915                 920                 925

Glu Lys Lys Trp Arg Asp Lys Arg Glu Lys Leu Gln Leu Glu Thr Lys
    930                 935                 940

Arg Val Tyr Thr Glu Ala Lys Glu Ala Val Asp Ala Leu Phe Val Asp
945                 950                 955                 960

Ser Gln Tyr Asp Arg Leu Gln Ala Asp Thr Asn Ile Gly Met Ile His
                965                 970                 975

Ala Ala Asp Lys Leu Val His Arg Ile Arg Glu Ala Tyr Leu Ser Glu
            980                 985                 990

Leu Pro Val Ile Pro Gly Val Asn Ala Glu Ile Phe Glu Glu Leu Glu
        995                 1000                1005

Gly His Ile Ile Thr Ala Ile Ser Leu Tyr Asp Ala Arg Asn Val Val
    1010                1015                1020

Lys Asn Gly Asp Phe Asn Asn Gly Leu Thr Cys Trp Asn Val Lys Gly
1025                1030                1035                1040

His Val Asp Val Gln Gln Ser His His Arg Ser Asp Leu Val Ile Pro
                1045                1050                1055

Glu Trp Glu Ala Glu Val Ser Gln Ala Val Arg Val Cys Pro Gly Cys
            1060                1065                1070

Gly Tyr Ile Leu Arg Val Thr Ala Tyr Lys Glu Gly Tyr Gly Glu Gly
        1075                1080                1085

Cys Val Thr Ile His Glu Ile Glu Asn Asn Thr Asp Glu Leu Lys Phe
    1090                1095                1100

Lys Asn Arg Glu Glu Glu Glu Val Tyr Pro Thr Asp Thr Gly Thr Cys
1105                1110                1115                1120

Asn Asp Tyr Thr Ala His Gln Gly Thr Ala Gly Cys Ala Asp Ala Cys
```

1125                1130                1135
Asn Ser Arg Asn Ala Gly Tyr Glu Asp Ala Tyr Glu Val Asp Thr Thr
            1140                1145                1150

Ala Ser Val Asn Tyr Lys Pro Thr Tyr Glu Glu Thr Tyr Thr Asp
        1155                1160                1165

Val Arg Arg Asp Asn His Cys Glu Tyr Asp Arg Gly Tyr Val Asn Tyr
        1170                1175                1180

Pro Pro Val Pro Ala Gly Tyr Val Thr Lys Glu Leu Glu Tyr Phe Pro
1185                1190                1195                1200

Glu Thr Asp Thr Val Trp Ile Glu Ile Gly Glu Thr Glu Gly Lys Phe
            1205                1210                1215

Ile Val Asp Ser Val Glu Leu Leu Leu Met Glu Glu
            1220                1225

<210> SEQ ID NO 9
<211> LENGTH: 1189
<212> TYPE: PRT
<213> ORGANISM: Bacillus thuringiensis

<400> SEQUENCE: 9

Met Glu Glu Asn Asn Gln Asn Gln Cys Ile Pro Tyr Asn Cys Leu Ser
 1               5                  10                  15

Asn Pro Glu Glu Val Leu Leu Asp Gly Glu Arg Ile Ser Thr Gly Asn
            20                  25                  30

Ser Ser Ile Asp Ile Ser Leu Ser Leu Val Gln Phe Leu Val Ser Asn
        35                  40                  45

Phe Val Pro Gly Gly Gly Phe Leu Val Gly Leu Ile Asp Phe Val Trp
    50                  55                  60

Gly Ile Val Gly Pro Ser Gln Trp Asp Ala Phe Leu Val Gln Ile Glu
65                  70                  75                  80

Gln Leu Ile Asn Glu Arg Ile Ala Glu Phe Ala Arg Asn Ala Ala Ile
                85                  90                  95

Ala Asn Leu Glu Gly Leu Gly Asn Asn Phe Asn Ile Tyr Val Glu Ala
            100                 105                 110

Phe Lys Glu Trp Glu Glu Asp Pro Asn Asn Pro Ala Thr Arg Thr Arg
        115                 120                 125

Val Ile Asp Arg Phe Arg Ile Leu Asp Gly Leu Leu Glu Arg Asp Ile
    130                 135                 140

Pro Ser Phe Arg Ile Ser Gly Phe Glu Val Pro Leu Leu Ser Val Tyr
145                 150                 155                 160

Ala Gln Ala Ala Asn Leu His Leu Ala Ile Leu Arg Asp Ser Val Ile
                165                 170                 175

Phe Gly Glu Arg Trp Gly Leu Thr Thr Ile Asn Val Asn Glu Asn Tyr
            180                 185                 190

Asn Arg Leu Ile Arg His Ile Asp Glu Tyr Ala Asp His Cys Ala Asn
        195                 200                 205

Thr Tyr Asn Arg Gly Leu Asn Asn Leu Pro Lys Ser Thr Tyr Gln Asp
    210                 215                 220

Trp Ile Thr Tyr Asn Arg Leu Arg Arg Asp Leu Thr Leu Thr Val Leu
225                 230                 235                 240

Asp Ile Ala Ala Phe Phe Pro Asn Tyr Asp Asn Arg Arg Tyr Pro Ile
                245                 250                 255

Gln Pro Val Gly Gln Leu Thr Arg Glu Val Tyr Thr Asp Pro Leu Ile
            260                 265                 270

Asn Phe Asn Pro Gln Leu Gln Ser Val Ala Gln Leu Pro Thr Phe Asn

```
                  275                 280                 285
Val Met Glu Ser Ser Ala Ile Arg Asn Pro His Leu Phe Asp Ile Leu
290                 295                 300

Asn Asn Leu Thr Ile Phe Thr Asp Trp Phe Ser Val Gly Arg Asn Phe
305                 310                 315                 320

Tyr Trp Gly Gly His Arg Val Ile Ser Ser Leu Ile Gly Gly Gly Asn
                325                 330                 335

Ile Thr Ser Pro Ile Tyr Gly Arg Glu Ala Asn Gln Glu Pro Pro Arg
                340                 345                 350

Ser Phe Thr Phe Asn Gly Pro Val Phe Arg Thr Leu Ser Asn Pro Thr
                355                 360                 365

Leu Arg Leu Leu Gln Gln Pro Trp Pro Ala Pro Pro Phe Asn Leu Arg
                370                 375                 380

Gly Val Glu Gly Val Glu Phe Ser Thr Pro Thr Asn Ser Phe Thr Tyr
385                 390                 395                 400

Arg Gly Arg Gly Thr Val Asp Ser Leu Thr Glu Leu Pro Pro Glu Asp
                405                 410                 415

Asn Ser Val Pro Pro Arg Glu Gly Tyr Ser His Arg Leu Cys His Ala
                420                 425                 430

Thr Phe Val Gln Arg Ser Gly Thr Pro Phe Leu Thr Thr Gly Val Val
                435                 440                 445

Phe Ser Trp Thr His Arg Ser Ala Thr Leu Thr Asn Thr Ile Asp Pro
                450                 455                 460

Glu Arg Ile Asn Gln Ile Pro Leu Val Lys Gly Phe Arg Val Trp Gly
465                 470                 475                 480

Gly Thr Ser Val Ile Thr Gly Pro Gly Phe Thr Gly Gly Asp Ile Leu
                485                 490                 495

Arg Arg Asn Thr Phe Gly Asp Phe Val Ser Leu Gln Val Asn Ile Asn
                500                 505                 510

Ser Pro Ile Thr Gln Arg Tyr Arg Leu Arg Phe Arg Tyr Ala Ser Ser
                515                 520                 525

Arg Asp Ala Arg Val Ile Val Leu Thr Gly Ala Ala Ser Thr Gly Val
530                 535                 540

Gly Gly Gln Val Ser Val Asn Met Pro Leu Gln Lys Thr Met Glu Ile
545                 550                 555                 560

Gly Glu Asn Leu Thr Ser Arg Thr Phe Arg Tyr Thr Asp Phe Ser Asn
                565                 570                 575

Pro Phe Ser Phe Arg Ala Asn Pro Asp Ile Ile Gly Ile Ser Glu Gln
                580                 585                 590

Pro Leu Phe Gly Ala Gly Ser Ile Ser Ser Gly Glu Leu Tyr Ile Asp
                595                 600                 605

Lys Ile Glu Ile Ile Leu Ala Asp Ala Thr Phe Glu Ala Glu Ser Asp
610                 615                 620

Leu Glu Arg Ala Gln Lys Ala Val Asn Ala Leu Phe Thr Ser Ser Asn
625                 630                 635                 640

Gln Ile Gly Leu Lys Thr Asp Val Thr Asp Tyr His Ile Asp Gln Val
                645                 650                 655

Ser Asn Leu Val Asp Cys Leu Ser Asp Glu Phe Cys Leu Asp Glu Lys
                660                 665                 670

Arg Glu Leu Ser Glu Lys Val Lys His Ala Lys Arg Leu Ser Asp Glu
                675                 680                 685

Arg Asn Leu Leu Gln Asp Pro Asn Phe Arg Gly Ile Asn Arg Gln Pro
690                 695                 700
```

-continued

```
Asp Arg Gly Trp Arg Gly Ser Thr Asp Ile Thr Ile Gln Gly Gly Asp
705                 710                 715                 720

Asp Val Phe Lys Glu Asn Tyr Val Thr Leu Pro Gly Thr Val Asp Glu
            725                 730                 735

Cys Tyr Pro Thr Tyr Leu Tyr Gln Lys Ile Asp Glu Ser Lys Leu Lys
            740                 745                 750

Ala Tyr Thr Arg Tyr Glu Leu Arg Gly Tyr Ile Glu Asp Ser Gln Asp
            755                 760                 765

Leu Glu Ile Tyr Leu Ile Arg Tyr Asn Ala Lys His Glu Ile Val Asn
        770                 775                 780

Val Pro Gly Thr Gly Ser Leu Trp Pro Leu Ser Ala Gln Ser Pro Ile
785                 790                 795                 800

Gly Lys Cys Gly Glu Pro Asn Arg Cys Ala Pro His Leu Glu Trp Asn
            805                 810                 815

Pro Asp Leu Asp Cys Ser Cys Arg Asp Gly Glu Lys Cys Ala His His
            820                 825                 830

Ser His His Phe Thr Leu Asp Ile Asp Val Gly Cys Thr Asp Leu Asn
        835                 840                 845

Glu Asp Leu Gly Val Trp Val Ile Phe Lys Ile Lys Thr Gln Asp Gly
850                 855                 860

His Ala Arg Leu Gly Asn Leu Glu Phe Leu Glu Glu Lys Pro Leu Leu
865                 870                 875                 880

Gly Glu Ala Leu Ala Arg Val Lys Arg Ala Glu Lys Lys Trp Arg Asp
            885                 890                 895

Lys Arg Glu Lys Leu Gln Leu Glu Thr Asn Ile Val Tyr Lys Glu Ala
            900                 905                 910

Lys Glu Ser Val Asp Ala Leu Phe Val Asn Ser Gln Tyr Asp Arg Leu
        915                 920                 925

Gln Val Asp Thr Asn Ile Ala Met Ile His Ala Ala Asp Lys Arg Val
930                 935                 940

His Arg Ile Arg Glu Ala Tyr Leu Pro Glu Leu Ser Val Ile Pro Gly
945                 950                 955                 960

Val Asn Ala Ala Ile Phe Glu Glu Leu Glu Gly Arg Ile Phe Thr Ala
            965                 970                 975

Tyr Ser Leu Tyr Asp Ala Arg Asn Val Ile Lys Asn Gly Asp Phe Asn
            980                 985                 990

Asn Gly Leu Leu Cys Trp Asn Val Lys Gly His Val Asp Val Glu Glu
        995                 1000                1005

Gln Asn Asn His Arg Ser Val Leu Val Ile Pro Glu Trp Glu Ala Glu
    1010                1015                1020

Val Ser Gln Glu Val Arg Val Cys Pro Gly Arg Gly Tyr Ile Leu Arg
1025                1030                1035                1040

Val Thr Ala Tyr Lys Glu Gly Tyr Gly Glu Gly Cys Val Thr Ile His
            1045                1050                1055

Glu Ile Glu Asp Asn Thr Asp Glu Leu Lys Phe Ser Asn Cys Val Glu
            1060                1065                1070

Glu Glu Val Tyr Pro Asn Asn Thr Val Thr Cys Asn Asn Tyr Thr Gly
        1075                1080                1085

Thr Gln Glu Glu Tyr Glu Gly Thr Tyr Thr Ser Arg Asn Gln Gly Tyr
    1090                1095                1100

Asp Glu Ala Tyr Gly Asn Asn Pro Ser Val Pro Ala Asp Tyr Ala Ser
1105                1110                1115                1120

Val Tyr Glu Glu Lys Ser Tyr Thr Asp Gly Arg Arg Glu Asn Pro Cys
            1125                1130                1135
```

Glu Ser Asn Arg Gly Tyr Gly Asp Tyr Thr Pro Leu Pro Ala Gly Tyr
            1140                1145                1150

Val Thr Lys Asp Leu Glu Tyr Phe Pro Glu Thr Asp Lys Val Trp Ile
        1155                1160                1165

Glu Ile Gly Glu Thr Gly Thr Phe Ile Val Asp Ser Val Glu Leu
    1170                1175                1180

Leu Leu Met Glu Glu
1185

<210> SEQ ID NO 10
<211> LENGTH: 1175
<212> TYPE: PRT
<213> ORGANISM: Bacillus thuringiensis serovar aizawai

<400> SEQUENCE: 10

Thr Met Glu Asn Asn Ile Gln Asn Gln Cys Val Pro Tyr Asn Cys Leu
 1               5                  10                  15

Asn Asn Pro Glu Val Glu Ile Leu Asn Glu Glu Arg Ser Thr Gly Arg
            20                  25                  30

Leu Pro Leu Asp Ile Ser Leu Ser Leu Thr Arg Phe Leu Leu Ser Glu
        35                  40                  45

Phe Val Pro Gly Val Gly Val Ala Phe Gly Leu Phe Asp Leu Ile Trp
    50                  55                  60

Gly Phe Ile Thr Pro Ser Asp Trp Ser Leu Phe Leu Leu Gln Ile Glu
65                  70                  75                  80

Gln Leu Ile Glu Gln Arg Ile Glu Thr Leu Glu Arg Asn Arg Ala Ile
                85                  90                  95

Thr Thr Leu Arg Gly Leu Ala Asp Ser Tyr Glu Ile Tyr Ile Glu Ala
            100                 105                 110

Leu Arg Glu Trp Glu Ala Asn Pro Asn Asn Ala Gln Leu Arg Glu Asp
        115                 120                 125

Val Arg Ile Arg Phe Ala Asn Thr Asp Asp Ala Leu Ile Thr Ala Ile
    130                 135                 140

Asn Asn Phe Thr Leu Thr Ser Phe Glu Ile Pro Leu Leu Ser Val Tyr
145                 150                 155                 160

Val Gln Ala Ala Asn Leu His Leu Ser Leu Leu Arg Asp Ala Val Ser
                165                 170                 175

Phe Gly Gln Gly Trp Gly Leu Asp Ile Ala Thr Val Asn Asn His Tyr
            180                 185                 190

Asn Arg Leu Ile Asn Leu Ile His Arg Tyr Thr Lys His Cys Leu Asp
        195                 200                 205

Thr Tyr Asn Gln Gly Leu Glu Asn Leu Arg Gly Thr Asn Thr Arg Gln
    210                 215                 220

Trp Ala Arg Phe Asn Gln Phe Arg Arg Asp Leu Thr Leu Thr Val Leu
225                 230                 235                 240

Asp Ile Val Ala Leu Phe Pro Asn Tyr Asp Val Arg Thr Tyr Pro Ile
                245                 250                 255

Gln Thr Ser Ser Gln Leu Thr Arg Glu Ile Tyr Thr Ser Ser Val Ile
            260                 265                 270

Glu Asp Ser Pro Val Ser Ala Asn Ile Pro Asn Gly Phe Asn Arg Ala
        275                 280                 285

Glu Phe Gly Val Arg Pro Pro His Leu Met Asp Phe Met Asn Ser Leu
    290                 295                 300

Phe Val Thr Ala Glu Thr Val Arg Ser Gln Thr Val Trp Gly Gly His
305                 310                 315                 320

-continued

Leu Val Ser Ser Arg Asn Thr Ala Gly Asn Arg Ile Asn Phe Pro Ser
            325                 330                 335

Tyr Gly Val Phe Asn Pro Gly Ala Ile Trp Ile Ala Asp Glu Asp
            340                 345                 350

Pro Arg Pro Phe Tyr Arg Thr Leu Ser Asp Pro Val Phe Val Arg Gly
            355                 360                 365

Gly Phe Gly Asn Pro His Tyr Val Leu Gly Leu Arg Gly Val Ala Phe
    370                 375                 380

Gln Gln Thr Gly Thr Asn His Thr Arg Thr Phe Arg Asn Ser Gly Thr
385                 390                 395                 400

Ile Asp Ser Leu Asp Glu Ile Pro Pro Gln Asp Asn Ser Gly Ala Pro
                405                 410                 415

Trp Asn Asp Tyr Ser His Val Leu Asn His Val Thr Phe Val Arg Trp
            420                 425                 430

Pro Gly Glu Ile Ser Gly Ser Asp Ser Trp Arg Ala Pro Met Phe Ser
            435                 440                 445

Trp Thr His Arg Ser Ala Thr Pro Thr Asn Thr Ile Asp Pro Glu Arg
        450                 455                 460

Ile Thr Gln Ile Pro Leu Val Lys Ala His Thr Leu Gln Ser Gly Thr
465                 470                 475                 480

Thr Val Val Arg Gly Pro Gly Phe Thr Gly Gly Asp Ile Leu Arg Arg
                485                 490                 495

Thr Ser Gly Gly Pro Phe Ala Tyr Thr Ile Val Asn Ile Asn Gly Gln
            500                 505                 510

Leu Pro Gln Arg Tyr Arg Ala Arg Ile Arg Tyr Ala Ser Thr Thr Asn
        515                 520                 525

Leu Arg Ile Tyr Val Thr Val Ala Gly Glu Arg Ile Phe Ala Gly Gln
    530                 535                 540

Phe Asn Lys Thr Met Asp Thr Gly Asp Pro Leu Thr Phe Gln Ser Phe
545                 550                 555                 560

Ser Tyr Ala Thr Ile Asn Thr Ala Phe Thr Phe Pro Met Ser Gln Ser
                565                 570                 575

Ser Phe Thr Val Gly Ala Asp Thr Phe Ser Ser Gly Asn Glu Val Tyr
            580                 585                 590

Ile Asp Arg Phe Glu Leu Ile Pro Val Thr Ala Thr Phe Glu Ala Glu
        595                 600                 605

Tyr Asp Leu Glu Arg Ala Gln Lys Ala Val Asn Ala Leu Phe Thr Ser
    610                 615                 620

Ile Asn Gln Ile Gly Ile Lys Thr Asp Val Thr Asp Tyr His Ile Asp
625                 630                 635                 640

Gln Val Ser Asn Leu Val Asp Cys Leu Ser Asp Glu Phe Cys Leu Asp
                645                 650                 655

Glu Lys Arg Glu Leu Ser Glu Lys Val Lys His Ala Lys Arg Leu Ser
            660                 665                 670

Asp Glu Arg Asn Leu Leu Gln Asp Pro Asn Phe Lys Gly Ile Asn Arg
        675                 680                 685

Gln Leu Asp Arg Gly Trp Arg Gly Ser Thr Asp Ile Thr Ile Gln Arg
    690                 695                 700

Gly Asp Asp Val Phe Lys Glu Asn Tyr Val Thr Leu Pro Gly Thr Phe
705                 710                 715                 720

Asp Glu Cys Tyr Pro Thr Tyr Leu Tyr Gln Lys Ile Asp Glu Ser Lys
                725                 730                 735

Leu Lys Pro Tyr Thr Arg Tyr Gln Leu Arg Gly Tyr Ile Glu Asp Ser

```
                740             745             750
Gln Asp Leu Glu Ile Tyr Leu Ile Arg Tyr Asn Ala Lys His Glu Thr
            755                 760             765
Val Asn Val Leu Gly Thr Gly Ser Leu Trp Pro Leu Ser Val Gln Ser
770             775                 780
Pro Ile Arg Lys Cys Gly Glu Pro Asn Arg Cys Ala Pro His Leu Glu
785             790                 795                 800
Trp Asn Pro Asp Leu Asp Cys Ser Cys Arg Asp Gly Glu Lys Cys Ala
                805                 810                 815
His His Ser His His Phe Ser Leu Asp Ile Asp Val Gly Cys Thr Asp
                820                 825                 830
Leu Asn Glu Asp Leu Asp Val Trp Val Ile Phe Lys Ile Lys Thr Gln
                835                 840                 845
Asp Gly His Ala Arg Leu Gly Asn Leu Glu Phe Leu Glu Glu Lys Pro
                850                 855                 860
Leu Val Gly Glu Ala Leu Ala Arg Val Lys Arg Ala Glu Lys Lys Trp
865                 870                 875                 880
Arg Asp Lys Arg Glu Lys Leu Glu Leu Glu Thr Asn Ile Val Tyr Lys
                    885                 890                 895
Glu Ala Lys Glu Ser Val Asp Ala Leu Phe Val Asn Ser Gln Tyr Asp
                    900                 905                 910
Gln Leu Gln Ala Asp Thr Asn Ile Ala Met Ile His Ala Ala Asp Lys
                    915                 920                 925
Arg Val His Arg Ile Arg Glu Ala Tyr Leu Pro Glu Leu Ser Val Ile
                    930                 935                 940
Pro Gly Val Asn Val Asp Ile Phe Glu Glu Leu Lys Gly Arg Ile Phe
945                 950                 955                 960
Thr Ala Phe Phe Leu Tyr Asp Ala Arg Asn Val Ile Lys Asn Gly Asp
                    965                 970                 975
Phe Asn Asn Gly Leu Ser Cys Trp Asn Val Lys Gly His Val Asp Val
                    980                 985                 990
Glu Glu Gln Asn Asn His Arg Ser Val Leu Val Val Pro Glu Trp Glu
                    995                 1000                1005
Ala Glu Val Ser Gln Glu Val Arg Val Cys Pro Gly Arg Gly Tyr Ile
                1010                1015                1020
Leu Arg Val Thr Ala Tyr Lys Glu Gly Tyr Gly Glu Gly Cys Val Thr
1025                1030                1035                1040
Ile His Glu Ile Glu Asn Asn Thr Asp Glu Leu Lys Phe Ser Asn Cys
                    1045                1050                1055
Val Glu Glu Glu Val Tyr Pro Asn Asn Thr Val Thr Cys Asn Asp Tyr
                    1060                1065                1070
Thr Ala Asn Gln Glu Glu Tyr Gly Gly Ala Tyr Thr Ser Arg Asn Arg
                    1075                1080                1085
Gly Tyr Asp Glu Thr Tyr Gly Ser Asn Ser Ser Val Pro Ala Asp Tyr
                    1090                1095                1100
Ala Ser Val Tyr Glu Glu Lys Ser Tyr Thr Asp Gly Arg Arg Asp Asn
1105                1110                1115                1120
Pro Cys Glu Ser Asn Arg Gly Tyr Gly Asp Tyr Thr Pro Leu Pro Ala
                    1125                1130                1135
Gly Tyr Val Thr Lys Glu Leu Glu Tyr Phe Pro Glu Thr Asp Lys Val
                    1140                1145                1150
Trp Ile Glu Ile Gly Glu Thr Glu Gly Thr Phe Ile Val Asp Ser Val
                    1155                1160                1165
```

```
Glu Leu Leu Leu Met Glu Glu
    1170            1175

<210> SEQ ID NO 11
<211> LENGTH: 719
<212> TYPE: PRT
<213> ORGANISM: Bacillus thuringiensis

<400> SEQUENCE: 11

Met Lys Leu Lys Asn Gln Asp Lys His Gln Ser Phe Ser Ser Asn Ala
  1               5                  10                  15

Lys Val Asp Lys Ile Ser Thr Asp Ser Leu Lys Asn Glu Thr Asp Ile
             20                  25                  30

Glu Leu Gln Asn Ile Asn His Glu Asp Cys Leu Lys Met Ser Glu Tyr
         35                  40                  45

Glu Asn Val Glu Pro Phe Val Ser Ala Ser Thr Ile Gln Thr Gly Ile
     50                  55                  60

Gly Ile Ala Gly Lys Ile Leu Gly Thr Leu Gly Val Pro Phe Ala Gly
 65                  70                  75                  80

Gln Val Ala Ser Leu Tyr Ser Phe Ile Leu Gly Glu Leu Trp Pro Lys
                 85                  90                  95

Gly Lys Asn Gln Trp Glu Ile Phe Met Glu His Val Glu Glu Ile Ile
            100                 105                 110

Asn Gln Lys Ile Ser Thr Tyr Ala Arg Asn Lys Ala Leu Thr Asp Leu
        115                 120                 125

Lys Gly Leu Gly Asp Ala Leu Ala Val Tyr His Asp Ser Leu Glu Ser
130                 135                 140

Trp Val Gly Asn Arg Asn Asn Thr Arg Ala Arg Ser Val Val Lys Ser
145                 150                 155                 160

Gln Tyr Ile Ala Leu Glu Leu Met Phe Val Gln Lys Leu Pro Ser Phe
                165                 170                 175

Ala Val Ser Gly Glu Glu Val Pro Leu Leu Pro Ile Tyr Ala Gln Ala
            180                 185                 190

Ala Asn Leu His Leu Leu Leu Leu Arg Asp Ala Ser Ile Phe Gly Lys
        195                 200                 205

Glu Trp Gly Leu Ser Ser Ser Glu Ile Ser Thr Phe Tyr Asn Arg Gln
    210                 215                 220

Val Glu Arg Ala Gly Asp Tyr Ser Asp His Cys Val Lys Trp Tyr Ser
225                 230                 235                 240

Thr Gly Leu Asn Asn Leu Arg Gly Thr Asn Ala Glu Ser Trp Val Arg
                245                 250                 255

Tyr Asn Gln Phe Arg Arg Asp Met Thr Leu Met Val Leu Asp Leu Val
            260                 265                 270

Ala Leu Phe Pro Ser Tyr Asp Thr Gln Met Tyr Pro Ile Lys Thr Thr
        275                 280                 285

Ala Gln Leu Thr Arg Glu Val Tyr Thr Asp Ala Ile Gly Thr Val His
    290                 295                 300

Pro His Pro Ser Phe Thr Ser Thr Thr Trp Tyr Asn Asn Asn Ala Pro
305                 310                 315                 320

Ser Phe Ser Ala Ile Glu Ala Ala Val Val Arg Asn Pro His Leu Leu
                325                 330                 335

Asp Phe Leu Glu Gln Val Thr Ile Tyr Ser Leu Leu Ser Arg Trp Ser
            340                 345                 350

Asn Thr Gln Tyr Met Asn Met Trp Gly Gly His Lys Leu Glu Phe Arg
        355                 360                 365
```

Thr Ile Gly Gly Thr Leu Asn Ile Ser Thr Gln Gly Ser Thr Asn Thr
            370                 375                 380

Ser Ile Asn Pro Val Thr Leu Pro Phe Thr Ser Arg Asp Val Tyr Arg
385                 390                 395                 400

Thr Glu Ser Leu Ala Gly Leu Asn Leu Phe Leu Thr Gln Pro Val Asn
                405                 410                 415

Gly Val Pro Arg Val Asp Phe His Trp Lys Phe Val Thr His Pro Ile
            420                 425                 430

Ala Ser Asp Asn Phe Tyr Tyr Pro Gly Tyr Ala Gly Ile Gly Thr Gln
        435                 440                 445

Leu Gln Asp Ser Glu Asn Glu Leu Pro Pro Glu Ala Thr Gly Gln Pro
    450                 455                 460

Asn Tyr Glu Ser Tyr Ser His Arg Leu Ser His Ile Gly Leu Ile Ser
465                 470                 475                 480

Ala Ser His Val Lys Ala Leu Val Tyr Ser Trp Thr His Arg Ser Ala
                485                 490                 495

Asp Arg Thr Asn Thr Ile Glu Pro Asn Ser Ile Thr Gln Ile Pro Leu
            500                 505                 510

Val Lys Ala Phe Asn Leu Ser Ser Gly Ala Ala Val Arg Gly Pro
        515                 520                 525

Gly Phe Thr Gly Gly Asp Ile Leu Arg Arg Thr Asn Thr Gly Thr Phe
    530                 535                 540

Gly Asp Ile Arg Val Asn Ile Asn Pro Pro Phe Ala Gln Arg Tyr Arg
545                 550                 555                 560

Val Arg Ile Arg Tyr Ala Ser Thr Thr Asp Leu Gln Phe His Thr Ser
                565                 570                 575

Ile Asn Gly Lys Ala Ile Asn Gln Gly Asn Phe Ser Ala Thr Met Asn
            580                 585                 590

Arg Gly Glu Asp Leu Asp Tyr Lys Thr Phe Arg Thr Val Gly Phe Thr
        595                 600                 605

Thr Pro Phe Ser Phe Leu Asp Val Gln Ser Thr Phe Thr Ile Gly Ala
    610                 615                 620

Trp Asn Phe Ser Ser Gly Asn Glu Val Tyr Ile Asp Arg Ile Glu Phe
625                 630                 635                 640

Val Pro Val Glu Val Thr Tyr Glu Ala Glu Tyr Asp Phe Glu Lys Ala
                645                 650                 655

Gln Glu Lys Val Thr Ala Leu Phe Thr Ser Thr Asn Pro Arg Gly Leu
            660                 665                 670

Lys Thr Asp Val Lys Asp Tyr His Ile Asp Gln Val Ser Asn Leu Val
        675                 680                 685

Glu Ser Leu Ser Asp Gly Phe Tyr Leu Asp Glu Lys Arg Glu Leu Phe
    690                 695                 700

Glu Ile Val Lys Tyr Ala Lys Gln Leu His Ile Glu Arg Asn Met
705                 710                 715

<210> SEQ ID NO 12
<211> LENGTH: 633
<212> TYPE: PRT
<213> ORGANISM: Bacillus thuringiensis serovar kurstaki

<400> SEQUENCE: 12

Met Asn Ser Val Leu Asn Ser Gly Arg Thr Thr Ile Cys Asp Ala Tyr
1               5                   10                  15

Asn Val Ala Ala His Asp Pro Phe Ser Phe Gln His Lys Ser Leu Asp
            20                  25                  30

-continued

```
Thr Val Gln Lys Glu Trp Thr Glu Trp Lys Lys Asn His Ser Leu
         35                  40                  45
Tyr Leu Asp Pro Ile Val Gly Thr Val Ala Ser Phe Leu Leu Lys Lys
     50                  55                  60
Val Gly Ser Leu Val Gly Lys Arg Ile Leu Ser Glu Leu Arg Asn Leu
 65                  70                  75                  80
Ile Phe Pro Ser Gly Ser Thr Asn Leu Met Gln Asp Ile Leu Arg Glu
                 85                  90                  95
Thr Glu Lys Phe Leu Asn Gln Arg Leu Asn Thr Asp Thr Leu Ala Arg
            100                 105                 110
Val Asn Ala Glu Leu Thr Gly Leu Gln Ala Asn Val Glu Glu Phe Asn
        115                 120                 125
Arg Gln Val Asp Asn Phe Leu Asn Pro Asn Arg Asn Ala Val Pro Leu
    130                 135                 140
Ser Ile Thr Ser Ser Val Asn Thr Met Gln Gln Leu Phe Leu Asn Arg
145                 150                 155                 160
Leu Pro Gln Phe Gln Met Gln Gly Tyr Gln Leu Leu Leu Leu Pro Leu
                165                 170                 175
Phe Ala Gln Ala Ala Asn Leu His Leu Ser Phe Ile Arg Asp Val Ile
            180                 185                 190
Leu Asn Ala Asp Glu Trp Gly Ile Ser Ala Ala Thr Leu Arg Thr Tyr
        195                 200                 205
Arg Asp Tyr Leu Lys Asn Tyr Thr Arg Asp Tyr Ser Asn Tyr Cys Ile
    210                 215                 220
Asn Thr Tyr Gln Ser Ala Phe Lys Gly Leu Asn Thr Arg Leu His Asp
225                 230                 235                 240
Met Leu Glu Phe Arg Thr Tyr Met Phe Leu Asn Val Phe Glu Tyr Val
                245                 250                 255
Ser Ile Trp Ser Leu Phe Lys Tyr Gln Ser Leu Leu Val Ser Ser Gly
            260                 265                 270
Ala Asn Leu Tyr Ala Ser Gly Ser Gly Pro Gln Gln Thr Gln Ser Phe
        275                 280                 285
Thr Ser Gln Asp Trp Pro Phe Leu Tyr Ser Leu Phe Gln Val Asn Ser
    290                 295                 300
Asn Tyr Val Leu Asn Gly Phe Ser Gly Ala Arg Leu Ser Asn Thr Phe
305                 310                 315                 320
Pro Asn Ile Val Gly Leu Pro Gly Ser Thr Thr His Ala Leu Leu
                325                 330                 335
Ala Ala Arg Val Asn Tyr Ser Gly Gly Ile Ser Ser Gly Asp Ile Gly
            340                 345                 350
Ala Ser Pro Phe Asn Gln Asn Phe Asn Cys Ser Thr Phe Leu Pro Pro
        355                 360                 365
Leu Leu Thr Pro Phe Val Arg Ser Trp Leu Asp Ser Gly Ser Asp Arg
    370                 375                 380
Glu Gly Val Ala Thr Val Thr Asn Trp Gln Thr Glu Ser Phe Glu Thr
385                 390                 395                 400
Thr Leu Gly Leu Arg Ser Gly Ala Phe Thr Ala Arg Gly Asn Ser Asn
                405                 410                 415
Tyr Phe Pro Asp Tyr Phe Ile Arg Asn Ile Ser Gly Val Pro Leu Val
            420                 425                 430
Val Arg Asn Glu Asp Leu Arg Arg Pro Leu His Tyr Asn Glu Ile Arg
        435                 440                 445
Asn Ile Ala Ser Pro Ser Gly Thr Pro Gly Gly Ala Arg Ala Tyr Met
    450                 455                 460
```

```
Val Ser Val His Asn Arg Lys Asn Asn Ile His Ala Val His Glu Asn
465                 470                 475                 480

Gly Ser Met Ile His Leu Ala Pro Asn Asp Tyr Thr Gly Phe Thr Ile
                485                 490                 495

Ser Pro Ile His Ala Thr Gln Val Asn Asn Gln Thr Arg Thr Phe Ile
            500                 505                 510

Ser Glu Lys Phe Gly Asn Gln Gly Asp Ser Leu Arg Phe Glu Gln Asn
        515                 520                 525

Asn Thr Thr Ala Arg Tyr Thr Leu Arg Gly Asn Gly Asn Ser Tyr Asn
    530                 535                 540

Leu Tyr Leu Arg Val Ser Ser Ile Gly Asn Ser Thr Ile Arg Val Thr
545                 550                 555                 560

Ile Asn Gly Arg Val Tyr Thr Ala Thr Asn Val Asn Thr Thr Thr Asn
                565                 570                 575

Asn Asp Gly Val Asn Asp Asn Gly Ala Arg Phe Ser Asp Ile Asn Ile
            580                 585                 590

Gly Asn Val Val Ala Ser Ser Asn Ser Asp Val Pro Leu Asp Ile Asn
        595                 600                 605

Val Thr Leu Asn Ser Gly Thr Gln Phe Asp Leu Met Asn Ile Met Leu
    610                 615                 620

Val Pro Thr Asn Ile Ser Pro Leu Tyr
625                 630

<210> SEQ ID NO 13
<211> LENGTH: 652
<212> TYPE: PRT
<213> ORGANISM: Bacillus thuringiensis

<400> SEQUENCE: 13

Met Ile Arg Lys Gly Gly Arg Lys Met Asn Pro Asn Asn Arg Ser Glu
1               5                   10                  15

His Asp Thr Ile Lys Thr Thr Glu Asn Asn Glu Val Pro Thr Asn His
                20                  25                  30

Val Gln Tyr Pro Leu Ala Glu Thr Pro Asn Pro Thr Leu Glu Asp Leu
            35                  40                  45

Asn Tyr Lys Glu Phe Leu Arg Met Thr Ala Asp Asn Asn Thr Glu Ala
    50                  55                  60

Leu Asp Ser Ser Thr Thr Lys Asp Val Ile Gln Lys Gly Ile Ser Val
65                  70                  75                  80

Val Gly Asp Leu Leu Gly Val Val Gly Phe Pro Phe Gly Gly Ala Leu
                85                  90                  95

Val Ser Phe Tyr Thr Asn Phe Leu Asn Thr Ile Trp Pro Ser Glu Asp
            100                 105                 110

Pro Trp Lys Ala Phe Met Glu Gln Val Glu Ala Leu Met Asp Gln Lys
    115                 120                 125

Ile Ala Asp Tyr Ala Lys Asn Lys Ala Leu Ala Glu Leu Gln Gly Leu
130                 135                 140

Gln Asn Asn Val Glu Asp Tyr Val Ser Ala Leu Ser Ser Trp Gln Lys
145                 150                 155                 160

Asn Pro Val Ser Ser Arg Asn Pro His Ser Gln Gly Arg Ile Arg Glu
                165                 170                 175

Leu Phe Ser Gln Ala Glu Ser His Phe Arg Asn Ser Met Pro Ser Phe
            180                 185                 190

Ala Ile Ser Gly Tyr Glu Val Leu Phe Leu Thr Thr Tyr Ala Gln Ala
    195                 200                 205
```

```
Ala Asn Thr His Leu Phe Leu Leu Lys Asp Ala Gln Ile Tyr Gly Glu
    210                 215                 220

Glu Trp Gly Tyr Glu Lys Glu Asp Ile Ala Glu Phe Tyr Lys Arg Gln
225                 230                 235                 240

Leu Lys Leu Thr Gln Glu Tyr Thr Asp His Cys Val Lys Trp Tyr Asn
                245                 250                 255

Val Gly Leu Asp Lys Leu Arg Gly Ser Ser Tyr Glu Ser Trp Val Asn
            260                 265                 270

Phe Asn Arg Tyr Arg Arg Glu Met Thr Leu Thr Val Leu Asp Leu Ile
        275                 280                 285

Ala Leu Phe Pro Leu Tyr Asp Val Arg Leu Tyr Pro Lys Glu Val Lys
    290                 295                 300

Thr Glu Leu Thr Arg Asp Val Leu Thr Asp Pro Ile Val Gly Val Asn
305                 310                 315                 320

Asn Leu Arg Gly Tyr Gly Thr Thr Phe Ser Asn Ile Glu Asn Tyr Ile
                325                 330                 335

Arg Lys Pro His Leu Phe Asp Tyr Leu His Arg Ile Gln Phe His Thr
            340                 345                 350

Arg Phe Gln Pro Gly Tyr Tyr Gly Asn Asp Ser Phe Asn Tyr Trp Ser
        355                 360                 365

Gly Asn Tyr Val Ser Thr Arg Pro Ser Ile Gly Ser Asn Asp Ile Ile
    370                 375                 380

Thr Ser Pro Phe Tyr Gly Asn Lys Ser Ser Glu Pro Val Gln Asn Leu
385                 390                 395                 400

Glu Phe Asn Gly Glu Lys Val Tyr Arg Ala Val Ala Asn Thr Asn Leu
                405                 410                 415

Ala Val Trp Pro Ser Ala Val Tyr Ser Gly Val Thr Lys Val Glu Phe
            420                 425                 430

Ser Gln Tyr Asn Asp Gln Thr Asp Glu Ala Ser Thr Gln Thr Tyr Asp
        435                 440                 445

Ser Lys Arg Asn Val Gly Ala Val Ser Trp Asp Ser Ile Asp Gln Leu
    450                 455                 460

Pro Pro Glu Thr Thr Asp Glu Pro Leu Glu Lys Gly Tyr Ser His Gln
465                 470                 475                 480

Leu Asn Tyr Val Met Cys Phe Leu Met Gln Gly Ser Arg Gly Thr Ile
                485                 490                 495

Pro Val Leu Thr Trp Thr His Lys Ser Val Asp Phe Phe Asn Met Ile
            500                 505                 510

Asp Ser Lys Lys Ile Thr Gln Leu Pro Leu Val Lys Ala Tyr Lys Leu
        515                 520                 525

Gln Ser Gly Ala Ser Val Val Ala Gly Pro Arg Phe Thr Gly Gly Asp
    530                 535                 540

Ile Ile Gln Cys Thr Glu Asn Gly Ser Ala Ala Thr Ile Tyr Val Thr
545                 550                 555                 560

Pro Asp Val Ser Tyr Ser Gln Lys Tyr Arg Ala Arg Ile His Tyr Ala
                565                 570                 575

Ser Thr Ser Gln Ile Thr Phe Thr Leu Ser Leu Asp Gly Ala Pro Phe
            580                 585                 590

Asn Gln Tyr Tyr Phe Asp Lys Thr Ile Asn Lys Gly Asp Thr Leu Thr
        595                 600                 605

Tyr Asn Ser Phe Asn Leu Ala Ser Phe Ser Thr Pro Phe Glu Leu Ser
    610                 615                 620

Gly Asn Asn Leu Gln Ile Gly Val Thr Gly Leu Ser Ala Gly Asp Lys
```

```
                   625                 630                 635                 640
Val Tyr Ile Asp Lys Ile Glu Phe Ile Pro Val Asn
                        645                 650

<210> SEQ ID NO 14
<211> LENGTH: 1138
<212> TYPE: PRT
<213> ORGANISM: Bacillus thuringiensis

<400> SEQUENCE: 14

Met Asn Leu Asn Leu Asp Gly Tyr Glu Asp Ser Asn Arg Thr Leu
  1               5                  10                  15

Asn Asn Ser Leu Asn Tyr Pro Thr Gln Lys Ala Leu Ser Pro Ser Leu
                 20                  25                  30

Lys Asn Met Asn Tyr Gln Asp Phe Leu Ser Ile Thr Glu Arg Glu Gln
             35                  40                  45

Pro Glu Ala Leu Ala Ser Gly Asn Thr Ala Ile Asn Thr Val Val Ser
 50                  55                  60

Val Thr Gly Ala Thr Leu Ser Ala Leu Gly Val Pro Gly Ala Ser Phe
 65                  70                  75                  80

Ile Thr Asn Phe Tyr Leu Lys Ile Ala Gly Leu Leu Trp Pro Glu Asn
                 85                  90                  95

Gly Lys Ile Trp Asp Glu Phe Met Thr Glu Val Glu Ala Leu Ile Asp
            100                 105                 110

Gln Lys Ile Glu Glu Tyr Val Arg Asn Lys Ala Ile Ala Glu Leu Asp
            115                 120                 125

Gly Leu Gly Ser Ala Leu Asp Lys Tyr Gln Lys Ala Leu Ala Asp Trp
130                 135                 140

Leu Gly Lys Gln Asp Asp Pro Glu Ala Ile Leu Ser Val Ala Thr Glu
145                 150                 155                 160

Phe Arg Ile Ile Asp Ser Leu Phe Glu Phe Ser Met Pro Ser Phe Lys
                165                 170                 175

Val Thr Gly Tyr Glu Ile Pro Leu Leu Thr Val Tyr Ala Gln Ala Ala
            180                 185                 190

Asn Leu His Leu Ala Leu Leu Arg Asp Ser Thr Leu Tyr Gly Asp Lys
            195                 200                 205

Trp Gly Phe Thr Gln Asn Asn Ile Glu Glu Asn Tyr Asn Arg Gln Lys
210                 215                 220

Lys Arg Ile Ser Glu Tyr Ser Asp His Cys Thr Lys Trp Tyr Asn Ser
225                 230                 235                 240

Gly Leu Ser Arg Leu Asn Gly Ser Thr Tyr Glu Gln Trp Ile Asn Tyr
                245                 250                 255

Asn Arg Phe Arg Arg Glu Met Ile Leu Met Ala Leu Asp Leu Val Ala
            260                 265                 270

Val Phe Pro Phe His Asp Pro Arg Arg Tyr Ser Met Glu Thr Ser Thr
            275                 280                 285

Gln Leu Thr Arg Glu Val Tyr Thr Asp Pro Val Ser Leu Ser Ile Ser
290                 295                 300

Asn Pro Asp Ile Gly Pro Ser Phe Ser Gln Met Glu Asn Thr Ala Ile
305                 310                 315                 320

Arg Thr Pro His Leu Val Asp Tyr Leu Asp Glu Leu Tyr Ile Tyr Thr
                325                 330                 335

Ser Lys Tyr Lys Ala Phe Ser His Glu Ile Gln Pro Asp Leu Phe Tyr
            340                 345                 350

Trp Ser Ala His Lys Val Ser Phe Lys Lys Ser Glu Gln Ser Asn Leu
```

```
                355                 360                 365
Tyr Thr Thr Gly Ile Tyr Gly Lys Thr Ser Gly Tyr Ile Ser Ser Gly
    370                 375                 380
Ala Tyr Ser Phe His Gly Asn Asp Ile Tyr Arg Thr Leu Ala Ala Pro
385                 390                 395                 400
Ser Val Val Tyr Pro Tyr Thr Gln Asn Tyr Gly Val Glu Gln Val
            405                 410                 415
Glu Phe Tyr Gly Val Lys Gly His Val His Tyr Arg Gly Asp Asn Lys
                420                 425                 430
Tyr Asp Leu Thr Tyr Asp Ser Ile Asp Gln Leu Pro Pro Asp Gly Glu
        435                 440                 445
Pro Ile His Glu Lys Tyr Thr His Arg Leu Cys His Ala Thr Ala Ile
    450                 455                 460
Phe Lys Ser Thr Pro Asp Tyr Asp Asn Ala Thr Ile Pro Ile Phe Ser
465                 470                 475                 480
Trp Thr His Arg Ser Ala Glu Tyr Tyr Asn Arg Ile Tyr Pro Asn Lys
            485                 490                 495
Ile Thr Lys Ile Pro Ala Val Lys Met Tyr Lys Leu Asp Asp Pro Ser
                500                 505                 510
Thr Val Val Lys Gly Pro Gly Phe Thr Gly Gly Asp Leu Val Lys Arg
        515                 520                 525
Gly Ser Thr Gly Tyr Ile Gly Asp Ile Lys Ala Thr Val Asn Ser Pro
    530                 535                 540
Leu Ser Gln Lys Tyr Arg Val Arg Val Arg Tyr Ala Thr Asn Val Ser
545                 550                 555                 560
Gly Gln Phe Asn Val Tyr Ile Asn Asp Lys Ile Thr Leu Gln Thr Lys
            565                 570                 575
Phe Gln Asn Thr Val Glu Thr Ile Gly Glu Gly Lys Asp Leu Thr Tyr
                580                 585                 590
Gly Ser Phe Gly Tyr Ile Glu Tyr Ser Thr Thr Ile Gln Phe Pro Asp
        595                 600                 605
Glu His Pro Lys Ile Thr Leu His Leu Ser Asp Leu Ser Asn Asn Ser
    610                 615                 620
Ser Phe Tyr Val Asp Ser Ile Glu Phe Ile Pro Val Asp Val Asn Tyr
625                 630                 635                 640
Ala Glu Lys Glu Lys Leu Glu Lys Ala Gln Lys Ala Val Asn Thr Leu
            645                 650                 655
Phe Thr Glu Gly Arg Asn Ala Leu Gln Lys Asp Val Thr Asp Tyr Lys
                660                 665                 670
Val Asp Gln Val Ser Ile Leu Val Asp Cys Ile Ser Gly Asp Leu Tyr
        675                 680                 685
Pro Asn Glu Lys Arg Glu Leu Gln Asn Leu Val Lys Tyr Ala Lys Arg
    690                 695                 700
Leu Ser Tyr Ser Arg Asn Leu Leu Leu Asp Pro Thr Phe Asp Ser Ile
705                 710                 715                 720
Asn Ser Ser Glu Glu Asn Gly Trp Tyr Gly Ser Asn Gly Ile Val Ile
            725                 730                 735
Gly Asn Gly Asp Phe Val Phe Lys Gly Asn Tyr Leu Ile Phe Ser Gly
                740                 745                 750
Thr Asn Asp Thr Gln Tyr Pro Thr Tyr Leu Tyr Gln Lys Ile Asp Glu
        755                 760                 765
Ser Lys Leu Lys Glu Tyr Thr Arg Tyr Lys Leu Lys Gly Phe Ile Glu
    770                 775                 780
```

```
Ser Ser Gln Asp Leu Glu Ala Tyr Val Ile Arg Tyr Asp Ala Lys His
785                 790                 795                 800

Arg Thr Leu Asp Val Ser Asp Asn Leu Leu Pro Asp Ile Leu Pro Glu
            805                 810                 815

Asn Thr Cys Gly Glu Pro Asn Arg Cys Ala Ala Gln Gln Tyr Leu Asp
            820                 825                 830

Glu Asn Pro Ser Pro Glu Cys Ser Ser Met Gln Asp Gly Ile Leu Ser
            835                 840                 845

Asp Ser His Ser Phe Ser Leu Asn Ile Asp Thr Gly Ser Ile Asn His
            850                 855                 860

Asn Glu Asn Leu Gly Ile Trp Val Leu Phe Lys Ile Ser Thr Leu Glu
865                 870                 875                 880

Gly Tyr Ala Lys Phe Gly Asn Leu Glu Val Ile Glu Asp Gly Pro Val
                885                 890                 895

Ile Gly Glu Ala Leu Ala Arg Val Lys Arg Gln Glu Thr Lys Trp Arg
            900                 905                 910

Asn Lys Leu Ala Gln Leu Thr Thr Glu Thr Gln Ala Ile Tyr Thr Arg
            915                 920                 925

Ala Lys Gln Ala Leu Asp Asn Leu Phe Ala Asn Ala Gln Asp Ser His
            930                 935                 940

Leu Lys Arg Asp Val Thr Phe Ala Glu Ile Ala Ala Ala Arg Lys Ile
945                 950                 955                 960

Val Gln Ser Ile Arg Glu Ala Tyr Met Ser Trp Leu Ser Val Val Pro
                965                 970                 975

Gly Val Asn His Pro Ile Phe Thr Glu Leu Ser Gly Arg Val Gln Arg
            980                 985                 990

Ala Phe Gln Leu Tyr Asp Val Arg Asn Val Val Arg Asn Gly Arg Phe
            995                 1000                1005

Leu Asn Gly Leu Ser Asp Trp Ile Val Thr Ser Asp Val Lys Val Gln
    1010                1015                1020

Glu Glu Asn Gly Asn Asn Val Leu Val Leu Asn Asn Trp Asp Ala Gln
1025                1030                1035                1040

Val Leu Gln Asn Val Lys Leu Tyr Gln Asp Arg Gly Tyr Ile Leu His
            1045                1050                1055

Val Thr Ala Arg Lys Ile Gly Ile Gly Glu Gly Tyr Ile Thr Ile Thr
            1060                1065                1070

Asp Glu Glu Gly His Thr Asp Gln Leu Arg Phe Thr Ala Cys Glu Glu
                1075                1080                1085

Ile Asp Ala Ser Asn Ala Phe Ile Ser Gly Tyr Ile Thr Lys Glu Leu
            1090                1095                1100

Glu Phe Phe Pro Asp Thr Glu Lys Val His Ile Glu Ile Gly Glu Thr
1105                1110                1115                1120

Glu Gly Ile Phe Leu Val Glu Ser Ile Glu Leu Phe Leu Met Glu Glu
                1125                1130                1135

Leu Cys

<210> SEQ ID NO 15
<211> LENGTH: 1157
<212> TYPE: PRT
<213> ORGANISM: Bacillus thuringiensis

<400> SEQUENCE: 15

Met Ser Pro Asn Asn Gln Asn Glu Tyr Glu Ile Ile Asp Ala Thr Pro
1               5                   10                  15

Ser Thr Ser Val Ser Ser Asp Ser Asn Arg Tyr Pro Phe Ala Asn Glu
```

```
                    20                  25                  30
Pro Thr Asp Ala Leu Gln Asn Met Asn Tyr Lys Asp Tyr Leu Lys Met
                35                  40                  45
Ser Gly Gly Glu Asn Pro Glu Leu Phe Gly Asn Pro Glu Thr Phe Ile
        50                  55                  60
Ser Ser Ser Thr Ile Gln Thr Gly Ile Gly Ile Val Gly Arg Ile Leu
65                  70                  75                  80
Gly Ala Leu Gly Val Pro Phe Ala Ser Gln Ile Ala Ser Phe Tyr Ser
                85                  90                  95
Phe Ile Val Gly Gln Leu Trp Pro Ser Lys Ser Val Asp Ile Trp Gly
                100                 105                 110
Glu Ile Met Glu Arg Val Glu Glu Leu Val Asp Gln Lys Ile Glu Lys
                115                 120                 125
Tyr Val Lys Asp Lys Ala Leu Ala Glu Leu Lys Gly Leu Gly Asn Ala
                130                 135                 140
Leu Asp Val Tyr Gln Gln Ser Leu Glu Asp Trp Leu Glu Asn Arg Asn
145                 150                 155                 160
Asp Ala Arg Thr Arg Ser Val Val Ser Asn Gln Phe Ile Ala Leu Asp
                165                 170                 175
Leu Asn Phe Val Ser Ser Ile Pro Ser Phe Ala Val Ser Gly His Glu
                180                 185                 190
Val Leu Leu Leu Ala Val Tyr Ala Gln Ala Val Asn Leu His Leu Leu
                195                 200                 205
Leu Leu Arg Asp Ala Ser Ile Phe Gly Glu Glu Trp Gly Phe Thr Pro
                210                 215                 220
Gly Glu Ile Ser Arg Phe Tyr Asn Arg Gln Val Gln Leu Thr Ala Glu
225                 230                 235                 240
Tyr Ser Asp Tyr Cys Val Lys Trp Tyr Lys Ile Gly Leu Asp Lys Leu
                245                 250                 255
Lys Gly Thr Thr Ser Lys Ser Trp Leu Asn Tyr His Gln Phe Arg Arg
                260                 265                 270
Glu Met Thr Leu Leu Val Leu Asp Leu Val Ala Leu Phe Pro Asn Tyr
                275                 280                 285
Asp Thr His Met Tyr Pro Ile Glu Thr Thr Ala Gln Leu Thr Arg Asp
                290                 295                 300
Val Tyr Thr Asp Pro Ile Ala Phe Asn Ile Val Thr Ser Thr Gly Phe
305                 310                 315                 320
Cys Asn Pro Trp Ser Thr His Ser Gly Ile Leu Phe Tyr Glu Val Glu
                325                 330                 335
Asn Asn Val Ile Arg Pro Pro His Leu Phe Asp Ile Leu Ser Ser Val
                340                 345                 350
Glu Ile Asn Thr Ser Arg Gly Gly Ile Thr Leu Asn Asn Asp Ala Tyr
                355                 360                 365
Ile Asn Tyr Trp Ser Gly His Thr Leu Lys Tyr Arg Arg Thr Ala Asp
                370                 375                 380
Ser Thr Val Thr Tyr Thr Ala Asn Tyr Gly Arg Ile Thr Ser Glu Lys
385                 390                 395                 400
Asn Ser Phe Ala Leu Glu Asp Arg Asp Ile Phe Glu Ile Asn Ser Thr
                405                 410                 415
Val Ala Asn Leu Ala Asn Tyr Tyr Gln Lys Ala Tyr Val Pro Gly
                420                 425                 430
Ser Trp Phe His Met Val Lys Arg Gly Thr Ser Ser Thr Ala Tyr
                435                 440                 445
```

```
Leu Tyr Ser Lys Thr His Thr Ala Leu Gln Gly Cys Thr Gln Val Tyr
    450                 455                 460

Glu Ser Ser Asp Glu Ile Pro Leu Asp Arg Thr Val Pro Val Ala Glu
465                 470                 475                 480

Ser Tyr Ser His Arg Leu Ser His Ile Thr Ser His Ser Phe Ser Lys
                485                 490                 495

Asn Gly Ser Ala Tyr Tyr Gly Ser Phe Pro Val Phe Val Trp Thr His
                500                 505                 510

Thr Ser Ala Asp Leu Asn Asn Thr Ile Tyr Ser Asp Lys Ile Thr Gln
            515                 520                 525

Ile Pro Ala Val Lys Gly Asp Met Leu Tyr Leu Gly Gly Ser Val Val
        530                 535                 540

Gln Gly Pro Gly Phe Thr Gly Gly Asp Ile Leu Lys Arg Thr Asn Pro
545                 550                 555                 560

Ser Ile Leu Gly Thr Phe Ala Val Thr Val Asn Gly Ser Leu Ser Gln
                565                 570                 575

Arg Tyr Arg Val Arg Ile Arg Tyr Ala Ser Thr Thr Asp Phe Glu Phe
                580                 585                 590

Thr Leu Tyr Leu Gly Asp Thr Ile Glu Lys Asn Arg Phe Asn Lys Thr
            595                 600                 605

Met Asp Asn Gly Ala Ser Leu Thr Tyr Glu Thr Phe Lys Phe Ala Ser
        610                 615                 620

Phe Ile Thr Asp Phe Gln Phe Arg Glu Thr Gln Asp Lys Ile Leu Leu
625                 630                 635                 640

Ser Met Gly Asp Phe Ser Ser Gly Gln Glu Val Tyr Ile Asp Arg Ile
                645                 650                 655

Glu Phe Ile Pro Val Asp Glu Thr Tyr Glu Ala Glu Gln Asp Leu Glu
                660                 665                 670

Ala Ala Lys Lys Ala Val Asn Ala Leu Phe Thr Asn Thr Lys Asp Gly
        675                 680                 685

Leu Arg Pro Gly Val Thr Asp Tyr Glu Val Asn Gln Ala Ala Asn Leu
        690                 695                 700

Val Glu Cys Leu Ser Asp Asp Leu Tyr Pro Asn Glu Lys Arg Leu Leu
705                 710                 715                 720

Phe Asp Ala Val Arg Glu Ala Lys Arg Leu Ser Gly Ala Arg Asn Leu
                725                 730                 735

Leu Gln Asp Pro Asp Phe Gln Glu Ile Asn Gly Glu Asn Gly Trp Ala
            740                 745                 750

Ala Ser Thr Gly Ile Glu Ile Val Glu Gly Asp Ala Val Phe Lys Gly
        755                 760                 765

Arg Tyr Leu Arg Leu Pro Gly Ala Arg Glu Ile Asp Thr Glu Thr Tyr
        770                 775                 780

Pro Thr Tyr Leu Tyr Gln Lys Val Glu Glu Gly Val Leu Lys Pro Tyr
785                 790                 795                 800

Thr Arg Tyr Arg Leu Arg Gly Phe Val Gly Ser Ser Gln Gly Leu Glu
                805                 810                 815

Ile Tyr Thr Ile Arg His Gln Thr Asn Arg Ile Val Lys Asn Val Pro
            820                 825                 830

Asp Asp Leu Leu Pro Asp Val Ser Pro Val Asn Ser Asp Gly Ser Ile
        835                 840                 845

Asn Arg Cys Ser Glu Gln Lys Tyr Val Asn Ser Arg Leu Glu Gly Glu
        850                 855                 860

Asn Arg Ser Gly Asp Ala His Glu Phe Ser Leu Pro Ile Asp Ile Gly
865                 870                 875                 880
```

Glu Leu Asp Tyr Asn Glu Asn Ala Gly Ile Trp Val Gly Phe Lys Ile
            885                 890                 895

Thr Asp Pro Glu Gly Tyr Ala Thr Leu Gly Asn Leu Glu Leu Val Glu
            900                 905                 910

Glu Gly Pro Leu Ser Gly Asp Ala Leu Glu Arg Leu Gln Arg Glu Glu
            915                 920                 925

Gln Gln Trp Lys Ile Gln Met Thr Arg Arg Glu Glu Thr Asp Arg
    930                 935                 940

Arg Tyr Met Ala Ser Lys Gln Ala Val Asp Arg Leu Tyr Ala Asp Tyr
945                 950                 955                 960

Gln Asp Gln Gln Leu Asn Pro Asp Val Glu Ile Thr Asp Leu Thr Ala
                965                 970                 975

Ala Gln Asp Leu Ile Gln Ser Ile Pro Tyr Val Tyr Asn Glu Met Phe
            980                 985                 990

Pro Glu Ile Pro Gly Met Asn Tyr Thr Lys Phe Thr Glu Leu Thr Asp
            995                 1000                1005

Arg Leu Gln Gln Ala Trp Asn Leu Tyr Asp Gln Arg Asn Ala Ile Pro
    1010                1015                1020

Asn Gly Asp Phe Arg Asn Gly Leu Ser Asn Trp Asn Ala Thr Pro Gly
1025                1030                1035                1040

Val Glu Val Gln Gln Ile Asn His Thr Ser Val Leu Val Ile Pro Asn
            1045                1050                1055

Trp Asp Glu Gln Val Ser Gln Gln Phe Thr Val Gln Pro Asn Gln Arg
            1060                1065                1070

Tyr Val Leu Arg Val Thr Ala Arg Lys Glu Gly Val Gly Asn Gly Tyr
            1075                1080                1085

Val Ser Ile Arg Asp Gly Gly Asn Gln Ser Glu Thr Leu Thr Phe Ser
            1090                1095                1100

Ala Ser Asp Tyr Asp Thr Asn Gly Val Tyr Asn Asp Gln Thr Gly Tyr
1105                1110                1115                1120

Ile Thr Lys Thr Val Thr Phe Ile Pro Tyr Thr Asp Gln Met Trp Ile
                1125                1130                1135

Glu Ile Ser Glu Thr Glu Gly Thr Phe Tyr Ile Glu Ser Val Glu Leu
            1140                1145                1150

Ile Val Asp Val Glu
        1155

<210> SEQ ID NO 16
<211> LENGTH: 675
<212> TYPE: PRT
<213> ORGANISM: Bacillus thuringiensis

<400> SEQUENCE: 16

Met Asn Pro Tyr Gln Asn Lys Asn Glu Tyr Glu Ile Phe Asn Ala Pro
1               5                   10                  15

Ser Asn Gly Phe Ser Lys Ser Asn Asn Tyr Ser Arg Tyr Pro Leu Ala
20 25 30

Asn Lys Pro Asn Gln Pro Leu Lys Asn Thr Asn Tyr Lys Asp Trp Leu
35 40 45

Asn Val Cys Gln Asp Asn Gln Gln Tyr Gly Asn Asn Ala Gly Asn Phe
50 55 60

Ala Ser Ser Glu Thr Ile Val Gly Val Ser Ala Gly Ile Ile Val Val
65 70 75 80

Gly Thr Met Leu Gly Ala Phe Ala Ala Pro Val Leu Ala Ala Gly Ile
85 90 95

```
Ile Ser Phe Gly Thr Leu Leu Pro Ile Phe Trp Gln Gly Ser Asp Pro
            100                 105                 110

Ala Asn Val Trp Gln Asp Leu Leu Asn Ile Gly Gly Arg Pro Ile Gln
            115                 120                 125

Glu Ile Asp Lys Asn Ile Ile Asn Val Leu Thr Ser Ile Val Thr Pro
    130                 135                 140

Ile Lys Asn Gln Leu Asp Lys Tyr Gln Glu Phe Phe Asp Lys Trp Glu
145                 150                 155                 160

Pro Ala Arg Thr His Ala Asn Ala Lys Ala Val His Asp Leu Phe Thr
                165                 170                 175

Thr Leu Glu Pro Ile Ile Asp Lys Asp Leu Asp Met Leu Lys Asn Asn
            180                 185                 190

Ala Ser Tyr Arg Ile Pro Thr Leu Pro Ala Tyr Ala Gln Ile Ala Thr
            195                 200                 205

Trp His Leu Asn Leu Leu Lys His Ala Ala Thr Tyr Tyr Asn Ile Trp
    210                 215                 220

Leu Gln Asn Gln Gly Ile Asn Pro Ser Thr Phe Asn Ser Ser Asn Tyr
225                 230                 235                 240

Tyr Gln Gly Tyr Leu Lys Arg Lys Ile Gln Glu Tyr Thr Asp Tyr Cys
                245                 250                 255

Ile Gln Thr Tyr Asn Ala Gly Leu Thr Met Ile Arg Thr Asn Thr Asn
            260                 265                 270

Ala Thr Trp Asn Met Tyr Asn Thr Tyr Arg Leu Glu Met Thr Leu Thr
            275                 280                 285

Val Leu Asp Leu Ile Ala Ile Phe Pro Asn Tyr Asp Pro Glu Lys Tyr
    290                 295                 300

Pro Ile Gly Val Lys Ser Glu Leu Ile Arg Glu Val Tyr Thr Asn Val
305                 310                 315                 320

Asn Ser Asp Thr Phe Arg Thr Ile Thr Glu Leu Glu Asn Gly Leu Thr
                325                 330                 335

Arg Asn Pro Thr Leu Phe Thr Trp Ile Asn Gln Gly Arg Phe Tyr Thr
            340                 345                 350

Arg Asn Ser Arg Asp Ile Leu Asp Pro Tyr Asp Ile Phe Ser Phe Thr
            355                 360                 365

Gly Asn Gln Met Ala Phe Thr His Thr Asn Asp Arg Asn Ile Ile
    370                 375                 380

Trp Gly Ala Val His Gly Asn Ile Ile Ser Gln Asp Thr Ser Lys Val
385                 390                 395                 400

Phe Pro Phe Tyr Arg Asn Lys Pro Ile Asp Lys Val Glu Ile Val Arg
                405                 410                 415

His Arg Glu Tyr Ser Asp Ile Ile Tyr Glu Met Ile Phe Phe Ser Asn
            420                 425                 430

Ser Ser Glu Val Phe Arg Tyr Ser Ser Asn Ser Thr Ile Glu Asn Asn
            435                 440                 445

Tyr Lys Arg Thr Asp Ser Tyr Met Ile Pro Lys Gln Thr Trp Lys Asn
            450                 455                 460

Glu Glu Tyr Gly His Thr Leu Ser Tyr Ile Lys Thr Asp Asn Tyr Ile
465                 470                 475                 480

Phe Ser Val Val Arg Glu Arg Arg Val Ala Phe Ser Trp Thr His
                485                 490                 495

Thr Ser Val Asp Phe Gln Asn Thr Ile Asp Leu Asp Asn Ile Thr Gln
            500                 505                 510

Ile His Ala Leu Lys Ala Leu Lys Val Ser Ser Asp Ser Lys Ile Val
```

```
                515                 520                 525
Lys Gly Pro Gly His Thr Gly Gly Asp Leu Val Ile Leu Lys Asp Ser
        530                 535                 540

Met Asp Phe Arg Val Arg Phe Leu Lys Asn Val Ser Arg Gln Tyr Gln
545                 550                 555                 560

Val Arg Ile Arg Tyr Ala Thr Asn Ala Pro Lys Thr Val Phe Leu
                565                 570                 575

Thr Gly Ile Asp Thr Ile Ser Val Glu Leu Pro Ser Thr Thr Ser Arg
                580                 585                 590

Gln Asn Pro Asn Ala Thr Asp Leu Thr Tyr Ala Asp Phe Gly Tyr Val
                595                 600                 605

Thr Phe Pro Arg Thr Val Pro Asn Lys Thr Phe Glu Gly Glu Asp Thr
        610                 615                 620

Leu Leu Met Thr Leu Tyr Gly Thr Pro Asn His Ser Tyr Asn Ile Tyr
625                 630                 635                 640

Ile Asp Lys Ile Glu Phe Ile Pro Ile Thr Gln Ser Val Leu Asp Tyr
                645                 650                 655

Thr Glu Lys Gln Asn Ile Glu Lys Thr Gln Lys Ile Val Asn Asp Leu
        660                 665                 670

Phe Val Asn
        675

<210> SEQ ID NO 17
<211> LENGTH: 719
<212> TYPE: PRT
<213> ORGANISM: Bacillus thuringiensis

<400> SEQUENCE: 17

Met Lys Leu Lys Asn Pro Asp Lys His Gln Ser Leu Ser Ser Asn Ala
1               5                   10                  15

Lys Val Asp Lys Ile Ala Thr Asp Ser Leu Lys Asn Glu Thr Asp Ile
                20                  25                  30

Glu Leu Lys Asn Ile Asn His Glu Asp Phe Leu Arg Met Ser Glu His
            35                  40                  45

Glu Ser Ile Asp Pro Phe Val Ser Ala Ser Thr Ile Gln Thr Gly Ile
        50                  55                  60

Gly Ile Ala Gly Lys Ile Leu Gly Thr Leu Gly Val Pro Phe Ala Gly
65                  70                  75                  80

Gln Ile Ala Ser Leu Tyr Ser Phe Ile Leu Gly Glu Leu Trp Pro Lys
                85                  90                  95

Gly Lys Ser Gln Trp Glu Ile Phe Met Glu His Val Glu Glu Leu Ile
                100                 105                 110

Asp Gln Lys Ile Ser Thr Tyr Ala Arg Asn Ile Ala Leu Ala Asp Leu
            115                 120                 125

Lys Gly Leu Gly Asp Ala Leu Ala Val Tyr His Glu Ser Leu Glu Ser
        130                 135                 140

Trp Ile Lys Asn Arg Asn Asn Ala Arg Ala Thr Ser Val Val Lys Ser
145                 150                 155                 160

Gln Tyr Ile Ala Leu Glu Leu Phe Val Gln Lys Leu Pro Ser Phe
                165                 170                 175                 Phe

Ala Val Ser Gly Glu Glu Val Pro Leu Leu Pro Ile Tyr Ala Gln Ala
            180                 185                 190

Ala Asn Leu His Leu Leu Leu Leu Arg Asp Ala Ser Val Phe Gly Lys
        195                 200                 205

Glu Trp Gly Leu Ser Asn Ser Gln Ile Ser Thr Phe Tyr Asn Arg Gln
```

-continued

```
            210                 215                 220
Val Glu Arg Thr Ser Asp Tyr Ser Asp His Cys Val Lys Trp Tyr Ser
225                 230                 235                 240

Thr Gly Leu Asn Asn Leu Arg Gly Thr Asn Ala Glu Ser Trp Val Arg
                245                 250                 255

Tyr Asn Gln Phe Arg Lys Asp Met Thr Leu Met Val Leu Asp Leu Ile
                260                 265                 270

Ala Leu Phe Pro Ser Tyr Asp Thr Leu Val Tyr Pro Ile Lys Thr Thr
            275                 280                 285

Ser Gln Leu Thr Arg Glu Val Tyr Thr Asp Ala Ile Gly Thr Val His
            290                 295                 300

Pro Asn Ala Ser Phe Ala Ser Thr Thr Trp Tyr Asn Asn Ala Pro
305                 310                 315                 320

Ser Phe Ser Ala Ile Glu Ser Ala Val Val Arg Asn Pro His Leu Leu
                325                 330                 335

Asp Phe Leu Glu Gln Val Thr Ile Tyr Ser Leu Leu Ser Arg Trp Ser
            340                 345                 350

Asn Thr Gln Tyr Met Asn Met Trp Gly Gly His Arg Leu Glu Phe Arg
            355                 360                 365

Thr Ile Gly Gly Val Leu Asn Thr Ser Thr Gln Gly Ser Thr Asn Thr
370                 375                 380

Ser Ile Asn Pro Val Thr Leu Pro Phe Thr Ser Arg Asp Val Tyr Arg
385                 390                 395                 400

Thr Glu Ser Leu Ala Gly Leu Asn Leu Phe Leu Thr Gln Pro Val Asn
                405                 410                 415

Gly Val Pro Arg Val Asp Phe His Trp Lys Phe Ala Thr Leu Pro Ile
                420                 425                 430

Ala Ser Asp Asn Phe Tyr Tyr Leu Gly Tyr Ala Gly Val Gly Thr Gln
            435                 440                 445

Leu Gln Asp Ser Glu Asn Glu Leu Pro Pro Gly Thr Thr Gly Gln Pro
            450                 455                 460

Asn Tyr Glu Ser Tyr Ser His Arg Leu Ser His Ile Gly Leu Ile Ser
465                 470                 475                 480

Ala Ser His Val Lys Ala Leu Val Tyr Ser Trp Thr His Arg Ser Ala
                485                 490                 495

Asp Arg Thr Asn Thr Ile Glu Pro Asn Ser Ile Thr Gln Ile Pro Leu
                500                 505                 510

Val Lys Ala Phe Asn Leu Ser Ser Gly Ala Ala Val Arg Gly Pro
            515                 520                 525

Gly Phe Thr Gly Gly Asp Ile Leu Arg Arg Thr Asn Thr Gly Thr Phe
            530                 535                 540

Gly Asp Ile Arg Val Asn Ile Asn Pro Pro Phe Ala Gln Arg Tyr Arg
545                 550                 555                 560

Val Arg Ile Arg Tyr Ala Ser Thr Thr Asp Leu Gln Phe His Thr Ser
                565                 570                 575

Ile Asn Gly Lys Ala Ile Asn Gln Gly Asn Phe Ser Ala Thr Met Asn
            580                 585                 590

Arg Gly Glu Asp Leu Asp Tyr Lys Thr Phe Arg Thr Val Gly Phe Thr
            595                 600                 605

Thr Pro Phe Ser Phe Ser Asp Val Gln Ser Thr Phe Thr Ile Gly Ala
            610                 615                 620

Trp Asn Phe Ser Ser Gly Asn Glu Val Tyr Ile Asp Arg Ile Glu Phe
625                 630                 635                 640
```

```
Val Pro Val Glu Val Thr Tyr Glu Ala Glu Tyr Asp Phe Glu Lys Ala
                645                 650                 655

Gln Glu Lys Val Thr Ala Leu Phe Thr Ser Thr Asn Pro Arg Gly Leu
            660                 665                 670

Lys Thr Asp Val Lys Asp Tyr His Ile Asp Gln Val Ser Asn Leu Val
        675                 680                 685

Glu Ser Leu Ser Asp Glu Phe Tyr Leu Asp Glu Lys Arg Glu Leu Phe
    690                 695                 700

Glu Ile Val Lys Tyr Ala Lys Gln Ile His Ile Glu Arg Asn Met
705                 710                 715

<210> SEQ ID NO 18
<211> LENGTH: 719
<212> TYPE: PRT
<213> ORGANISM: Bacillus thuringiensis

<400> SEQUENCE: 18

Met Lys Leu Lys Asn Gln Asp Lys His Gln Ser Phe Ser Ser Asn Ala
  1               5                  10                  15

Lys Val Asp Lys Ile Ser Thr Asp Ser Leu Lys Asn Glu Thr Asp Ile
             20                  25                  30

Glu Leu Gln Asn Ile Asn His Glu Asp Cys Leu Lys Met Ser Glu Tyr
         35                  40                  45

Glu Asn Val Glu Pro Phe Val Ser Ala Ser Thr Ile Gln Thr Gly Ile
 50                  55                  60

Gly Ile Ala Gly Lys Ile Leu Gly Thr Leu Gly Val Pro Phe Ala Gly
 65                  70                  75                  80

Gln Val Ala Ser Leu Tyr Ser Phe Ile Leu Gly Glu Leu Trp Pro Lys
                 85                  90                  95

Gly Lys Asn Gln Trp Glu Ile Phe Met Glu His Val Glu Glu Ile Ile
            100                 105                 110

Asn Gln Lys Ile Ser Thr Tyr Ala Arg Asn Lys Ala Leu Thr Asp Leu
        115                 120                 125

Lys Gly Leu Gly Asp Ala Leu Ala Val Tyr His Asp Ser Leu Glu Ser
130                 135                 140

Trp Val Gly Asn Arg Asn Asn Thr Arg Ala Arg Ser Val Val Lys Ser
145                 150                 155                 160

Gln Tyr Ile Ala Leu Glu Leu Met Phe Val Gln Lys Leu Pro Ser Phe
                165                 170                 175

Ala Val Ser Gly Glu Glu Val Pro Leu Leu Pro Ile Tyr Ala Gln Ala
            180                 185                 190

Ala Asn Leu His Leu Leu Leu Leu Arg Asp Ala Ser Ile Phe Gly Lys
        195                 200                 205

Glu Trp Gly Leu Ser Ser Ser Glu Ile Ser Thr Phe Tyr Asn Arg Gln
210                 215                 220

Val Glu Arg Ala Gly Asp Tyr Ser Tyr His Cys Val Lys Trp Tyr Ser
225                 230                 235                 240

Thr Gly Leu Asn Asn Leu Arg Gly Thr Asn Ala Glu Ser Trp Val Arg
                245                 250                 255

Tyr Asn Gln Phe Arg Arg Asp Met Thr Leu Met Val Leu Asp Leu Val
            260                 265                 270

Ala Leu Phe Pro Ser Tyr Asp Thr Gln Met Tyr Pro Ile Lys Thr Thr
        275                 280                 285

Ala Gln Leu Thr Arg Glu Val Tyr Thr Asp Ala Ile Gly Thr Val His
290                 295                 300
```

```
Pro His Pro Ser Phe Thr Ser Thr Thr Trp Tyr Asn Asn Asn Ala Pro
305                 310                 315                 320

Ser Phe Ser Ala Ile Glu Ala Ala Val Val Arg Asn Pro His Leu Leu
            325                 330                 335

Asp Phe Leu Glu Gln Val Thr Ile Tyr Ser Leu Leu Ser Arg Trp Ser
        340                 345                 350

Asn Thr Gln Tyr Met Asn Met Trp Gly Gly His Lys Leu Glu Phe Arg
    355                 360                 365

Thr Ile Gly Gly Thr Leu Asn Ile Ser Thr Gln Gly Ser Thr Asn Thr
370                 375                 380

Ser Ile Asn Pro Val Thr Leu Pro Phe Thr Ser Arg Asp Val Tyr Arg
385                 390                 395                 400

Thr Glu Ser Leu Ala Gly Leu Asn Leu Phe Leu Thr Gln Pro Val Asn
            405                 410                 415

Gly Val Pro Arg Val Asp Phe His Trp Lys Phe Val Thr His Pro Ile
        420                 425                 430

Ala Ser Asp Asn Phe Tyr Tyr Pro Gly Tyr Ala Gly Ile Gly Thr Gln
    435                 440                 445

Leu Gln Asp Ser Glu Asn Glu Leu Pro Pro Glu Ala Thr Gly Gln Pro
450                 455                 460

Asn Tyr Glu Ser Tyr Ser His Arg Leu Ser His Ile Gly Leu Ile Ser
465                 470                 475                 480

Ala Ser His Val Lys Ala Leu Val Tyr Ser Trp Thr His Arg Ser Ala
            485                 490                 495

Asp Arg Thr Asn Thr Ile Glu Pro Asn Ser Ile Thr Gln Ile Pro Leu
        500                 505                 510

Val Lys Ala Phe Asn Leu Ser Ser Gly Ala Ala Val Val Arg Gly Pro
    515                 520                 525

Gly Phe Thr Gly Gly Asp Ile Leu Arg Arg Thr Asn Thr Gly Thr Phe
530                 535                 540

Gly Asp Ile Arg Val Asn Ile Asn Pro Pro Phe Ala Gln Arg Tyr Arg
545                 550                 555                 560

Val Arg Ile Arg Tyr Ala Ser Thr Thr Asp Leu Gln Phe His Thr Ser
            565                 570                 575

Ile Asn Gly Lys Ala Ile Asn Gln Gly Asn Phe Ser Ala Thr Met Asn
        580                 585                 590

Arg Gly Glu Asp Leu Asp Tyr Lys Thr Phe Arg Thr Val Gly Phe Thr
    595                 600                 605

Thr Pro Phe Ser Phe Leu Asp Val Gln Ser Thr Phe Thr Ile Gly Ala
610                 615                 620

Trp Asn Phe Ser Ser Gly Asn Glu Val Tyr Ile Asp Arg Ile Glu Phe
625                 630                 635                 640

Val Pro Val Glu Val Thr Tyr Glu Ala Glu Tyr Asp Phe Glu Lys Ala
            645                 650                 655

Gln Glu Lys Val Thr Ala Leu Phe Thr Ser Thr Asn Pro Arg Gly Leu
        660                 665                 670

Lys Thr Asp Val Lys Asp Tyr His Ile Asp Gln Val Ser Asn Leu Val
    675                 680                 685

Glu Ser Leu Ser Asp Glu Phe Tyr Leu Asp Glu Lys Arg Glu Leu Phe
690                 695                 700

Glu Ile Val Lys Tyr Ala Lys Gln Leu His Ile Glu Arg Asn Met
705                 710                 715
```

<210> SEQ ID NO 19

```
<211> LENGTH: 719
<212> TYPE: PRT
<213> ORGANISM: Bacillus thuringiensis

<400> SEQUENCE: 19

Met Lys Leu Lys Asn Gln Asp Lys His Gln Ser Phe Ser Ser Asn Ala
1               5                   10                  15

Lys Val Asp Lys Ile Ser Thr Asp Ser Leu Lys Asn Glu Thr Asp Ile
            20                  25                  30

Glu Leu Gln Asn Ile Asn His Glu Asp Cys Leu Lys Met Ser Glu Tyr
        35                  40                  45

Glu Asn Val Glu Pro Phe Val Ser Ala Ser Thr Ile Gln Thr Gly Ile
    50                  55                  60

Gly Ile Ala Gly Lys Ile Leu Gly Thr Leu Gly Val Pro Phe Ala Gly
65                  70                  75                  80

Gln Val Ala Ser Leu Tyr Ser Phe Ile Leu Gly Glu Leu Trp Pro Lys
                85                  90                  95

Gly Lys Asn Gln Trp Glu Ile Phe Met Glu His Val Glu Glu Ile Ile
            100                 105                 110

Asn Gln Lys Ile Ser Thr Tyr Ala Arg Asn Lys Ala Leu Thr Asp Leu
        115                 120                 125

Lys Gly Leu Gly Asp Ala Leu Ala Val Tyr His Asp Ser Leu Glu Ser
130                 135                 140

Trp Val Gly Asn Arg Asn Asn Thr Arg Ala Arg Ser Val Val Lys Ser
145                 150                 155                 160

Gln Tyr Ile Ala Leu Glu Leu Met Phe Val Gln Lys Leu Pro Ser Phe
                165                 170                 175

Ala Val Ser Gly Glu Glu Val Pro Leu Leu Pro Ile Tyr Ala Gln Ala
            180                 185                 190

Ala Asn Leu His Leu Leu Leu Arg Asp Ala Ser Ile Phe Gly Lys
        195                 200                 205

Glu Trp Gly Leu Ser Ser Ser Glu Ile Ser Thr Phe Tyr Asn Arg Gln
    210                 215                 220

Val Glu Arg Ala Gly Asp Tyr Ser Asp His Cys Val Lys Trp Tyr Ser
225                 230                 235                 240

Thr Gly Leu Asn Asn Leu Arg Gly Thr Asn Ala Glu Ser Trp Val Arg
                245                 250                 255

Tyr Asn Gln Phe Arg Arg Asp Met Thr Leu Met Val Leu Asp Leu Val
            260                 265                 270

Ala Leu Phe Pro Ser Tyr Asp Thr Gln Met Tyr Pro Ile Lys Thr Thr
        275                 280                 285

Ala Gln Leu Thr Arg Glu Val Tyr Thr Asp Ala Ile Gly Thr Val His
    290                 295                 300

Pro His Pro Ser Phe Thr Ser Thr Thr Trp Tyr Asn Asn Asn Ala Pro
305                 310                 315                 320

Ser Phe Ser Ala Ile Glu Ala Ala Val Val Arg Asn Pro His Leu Leu
                325                 330                 335

Asp Phe Leu Glu Gln Val Thr Ile Tyr Ser Leu Leu Ser Arg Trp Ser
            340                 345                 350

Asn Thr Gln Tyr Met Asn Met Trp Gly Gly His Lys Leu Glu Phe Arg
        355                 360                 365

Thr Ile Gly Gly Thr Leu Asn Ile Ser Thr Gln Gly Ser Thr Asn Thr
    370                 375                 380

Ser Ile Asn Pro Val Thr Leu Pro Phe Thr Ser Arg Asp Val Tyr Arg
385                 390                 395                 400
```

Thr Glu Ser Leu Ala Gly Leu Asn Leu Phe Leu Thr Gln Pro Val Asn
            405                 410                 415

Gly Val Pro Arg Val Asp Phe His Trp Lys Phe Val Thr His Pro Ile
        420                 425                 430

Ala Ser Asp Asn Phe Tyr Tyr Pro Gly Tyr Ala Gly Ile Gly Thr Gln
            435                 440                 445

Leu Gln Asp Ser Glu Asn Glu Leu Pro Pro Glu Ala Thr Gly Gln Pro
        450                 455                 460

Asn Tyr Glu Ser Tyr Ser His Arg Leu Ser His Ile Gly Leu Ile Ser
465                 470                 475                 480

Ala Ser His Val Lys Ala Leu Val Tyr Ser Trp Thr His Arg Ser Ala
                485                 490                 495

Asp Arg Thr Asn Thr Ile Glu Pro Asn Ser Ile Thr Gln Ile Pro Leu
            500                 505                 510

Val Lys Ala Phe Asn Leu Ser Ser Gly Ala Ala Val Val Arg Gly Pro
        515                 520                 525

Gly Phe Thr Gly Gly Asp Ile Leu Arg Arg Thr Asn Thr Gly Thr Phe
    530                 535                 540

Gly Asp Ile Arg Val Asn Ile Asn Pro Pro Phe Ala Gln Arg Tyr Arg
545                 550                 555                 560

Val Arg Ile Arg Tyr Ala Ser Thr Thr Asp Leu Gln Phe His Thr Ser
                565                 570                 575

Ile Asn Gly Lys Ala Ile Asn Gln Gly Asn Phe Ser Ala Thr Met Asn
            580                 585                 590

Arg Gly Glu Asp Leu Asp Tyr Lys Thr Phe Arg Thr Val Gly Phe Thr
        595                 600                 605

Thr Pro Phe Ser Phe Leu Asp Val Gln Ser Thr Phe Thr Ile Gly Ala
    610                 615                 620

Trp Asn Phe Ser Ser Gly Asn Glu Val Tyr Ile Asp Arg Ile Glu Phe
625                 630                 635                 640

Val Pro Val Glu Val Thr Tyr Glu Ala Glu Tyr Asp Phe Glu Lys Ala
                645                 650                 655

Gln Glu Lys Val Thr Ala Leu Phe Thr Ser Thr Asn Pro Arg Gly Leu
            660                 665                 670

Lys Thr Asp Val Lys Asp Tyr His Ile Asp Gln Val Ser Asn Leu Val
        675                 680                 685

Glu Ser Leu Ser Asp Glu Phe Tyr Leu Asp Glu Lys Arg Glu Leu Phe
    690                 695                 700

Glu Ile Val Lys Tyr Ala Lys Gln Leu His Ile Glu Arg Asn Met
705                 710                 715

<210> SEQ ID NO 20
<211> LENGTH: 719
<212> TYPE: PRT
<213> ORGANISM: Bacillus thuringiensis

<400> SEQUENCE: 20

Met Lys Leu Lys Asn Gln Asp Lys His Gln Ser Phe Ser Ser Asn Ala
 1               5                  10                  15

Lys Val Asp Lys Ile Ser Thr Asp Ser Leu Lys Asn Glu Thr Asp Ile
            20                  25                  30

Glu Leu Gln Asn Ile Asn His Glu Asp Cys Leu Lys Met Ser Glu Tyr
        35                  40                  45

Glu Asn Val Glu Pro Phe Val Ser Ala Ser Thr Ile Gln Thr Gly Ile
    50                  55                  60

```
Gly Ile Ala Gly Lys Ile Leu Gly Thr Leu Gly Val Pro Phe Ala Gly
 65                  70                  75                  80

Gln Val Ala Ser Leu Tyr Ser Phe Ile Leu Gly Glu Leu Trp Pro Lys
                 85                  90                  95

Gly Lys Asn Gln Trp Glu Ile Phe Met Glu His Val Glu Glu Ile Ile
            100                 105                 110

Asn Gln Lys Ile Ser Thr Tyr Ala Arg Asn Lys Ala Leu Thr Asp Leu
        115                 120                 125

Lys Gly Leu Gly Asp Ala Leu Ala Val Tyr His Asp Ser Leu Glu Ser
130                 135                 140

Trp Val Gly Asn Arg Asn Asn Thr Arg Ala Arg Ser Val Val Lys Ser
145                 150                 155                 160

Gln Tyr Ile Ala Leu Glu Leu Met Phe Val Gln Lys Leu Pro Ser Phe
                165                 170                 175

Ala Val Ser Gly Glu Glu Val Pro Leu Leu Pro Ile Tyr Ala Gln Ala
            180                 185                 190

Ala Asn Leu His Leu Leu Leu Arg Asp Ala Ser Ile Phe Gly Lys
        195                 200                 205

Glu Trp Gly Leu Ser Ser Ser Glu Ile Ser Thr Phe Tyr Asn Arg Gln
210                 215                 220

Val Glu Arg Ala Gly Asp Tyr Ser Tyr His Cys Val Lys Trp Tyr Ser
225                 230                 235                 240

Thr Gly Leu Asn Asn Leu Arg Gly Thr Asn Ala Glu Ser Trp Val Arg
                245                 250                 255

Tyr Asn Gln Phe Arg Arg Asp Met Thr Leu Met Val Leu Asp Leu Val
            260                 265                 270

Ala Leu Phe Pro Ser Tyr Asp Thr Gln Met Tyr Pro Ile Lys Thr Thr
        275                 280                 285

Ala Gln Leu Thr Arg Glu Val Tyr Thr Asp Ala Ile Gly Thr Val His
290                 295                 300

Pro His Pro Ser Phe Thr Ser Thr Trp Tyr Asn Asn Asn Ala Pro
305                 310                 315                 320

Ser Phe Ser Ala Ile Glu Ala Ala Val Val Arg Asn Pro His Leu Leu
                325                 330                 335

Asp Phe Leu Glu Gln Val Thr Ile Tyr Ser Leu Leu Ser Arg Trp Ser
            340                 345                 350

Asn Thr Gln Tyr Met Asn Met Trp Gly Gly His Lys Leu Glu Phe Arg
        355                 360                 365

Thr Ile Gly Gly Thr Leu Asn Ile Ser Thr Gln Gly Ser Thr Asn Thr
370                 375                 380

Ser Ile Asn Pro Val Thr Leu Pro Phe Thr Ser Arg Asp Val Tyr Arg
385                 390                 395                 400

Thr Glu Ser Leu Ala Gly Leu Asn Leu Phe Leu Thr Gln Pro Val Asn
                405                 410                 415

Gly Val Pro Arg Val Asp Phe His Trp Lys Phe Val Thr His Pro Ile
            420                 425                 430

Ala Ser Asp Asn Phe Tyr Tyr Pro Gly Tyr Ala Gly Ile Gly Thr Gln
        435                 440                 445

Leu Gln Asp Ser Glu Asn Glu Leu Pro Pro Glu Ala Thr Gly Gln Pro
450                 455                 460

Asn Tyr Glu Ser Tyr Ser His Arg Leu Ser His Ile Gly Leu Ile Ser
465                 470                 475                 480

Ala Ser His Val Lys Ala Leu Val Tyr Ser Trp Thr His Arg Ser Ala
```

```
                   485                 490                 495
Asp Arg Thr Asn Thr Ile Glu Pro Asn Ser Ile Thr Gln Ile Pro Leu
                500                 505                 510

Val Lys Ala Phe Asn Leu Ser Ser Gly Ala Ala Val Val Arg Gly Pro
                515                 520                 525

Gly Phe Thr Gly Gly Asp Ile Leu Arg Arg Thr Asn Thr Gly Thr Phe
                530                 535                 540

Gly Asp Ile Arg Val Asn Ile Asn Pro Pro Phe Ala Gln Arg Tyr Arg
545                 550                 555                 560

Val Arg Ile Arg Tyr Ala Ser Thr Thr Asp Leu Gln Phe His Thr Ser
                565                 570                 575

Ile Asn Gly Lys Ala Ile Asn Gln Gly Asn Phe Ser Ala Thr Met Asn
                580                 585                 590

Arg Gly Glu Asp Leu Asp Tyr Lys Thr Phe Arg Thr Val Gly Phe Thr
                595                 600                 605

Thr Pro Phe Ser Phe Leu Asp Val Gln Ser Thr Phe Thr Ile Gly Ala
                610                 615                 620

Trp Asn Phe Ser Ser Gly Asn Glu Val Tyr Ile Asp Arg Ile Glu Phe
625                 630                 635                 640

Val Pro Val Glu Val Thr Tyr Glu Ala Glu Tyr Asp Phe Glu Lys Ala
                645                 650                 655

Gln Glu Lys Val Thr Ala Leu Phe Thr Ser Thr Asn Pro Arg Gly Leu
                660                 665                 670

Lys Thr Asp Val Lys Asp Tyr His Ile Asp Gln Val Ser Asn Leu Val
                675                 680                 685

Glu Ser Leu Ser Asp Glu Phe Tyr Leu Asp Glu Lys Arg Glu Leu Phe
                690                 695                 700

Glu Ile Val Lys Tyr Ala Asn Glu Leu His Ile Glu Arg Asn Met
705                 710                 715

<210> SEQ ID NO 21
<211> LENGTH: 719
<212> TYPE: PRT
<213> ORGANISM: Bacillus thuringiensis

<400> SEQUENCE: 21

Met Lys Leu Lys Asn Gln Asp Lys His Gln Ser Phe Ser Ser Asn Ala
1               5                   10                  15

Lys Val Asp Lys Ile Ser Thr Asp Ser Leu Lys Asn Glu Thr Asp Ile
                20                  25                  30

Glu Leu Gln Asn Ile Asn His Glu Asp Cys Leu Lys Met Ser Glu Tyr
                35                  40                  45

Glu Asn Val Glu Pro Phe Val Ser Ala Ser Thr Ile Gln Thr Gly Ile
                50                  55                  60

Gly Ile Ala Gly Lys Ile Leu Gly Thr Leu Gly Val Pro Phe Ala Gly
65                  70                  75                  80

Gln Val Ala Ser Leu Tyr Ser Phe Ile Leu Gly Glu Leu Trp Pro Lys
                85                  90                  95

Gly Lys Asn Gln Trp Glu Ile Phe Met Glu His Val Glu Glu Ile Ile
                100                 105                 110

Asn Gln Lys Ile Ser Thr Tyr Ala Arg Asn Lys Ala Leu Thr Asp Leu
                115                 120                 125

Lys Gly Leu Gly Asp Ala Leu Ala Val Tyr His Asp Ser Leu Glu Ser
                130                 135                 140

Trp Val Gly Asn Arg Asn Asn Thr Arg Ala Arg Ser Val Val Lys Ser
```

```
                145                 150                 155                 160
Gln Tyr Ile Ala Leu Glu Leu Met Phe Val Gln Lys Leu Pro Ser Phe
                165                 170                 175
Ala Val Ser Gly Glu Glu Val Pro Leu Leu Pro Ile Tyr Ala Gln Ala
                180                 185                 190
Ala Asn Leu His Leu Leu Leu Arg Asp Ala Ser Ile Phe Gly Lys
            195                 200                 205
Glu Trp Gly Leu Ser Ser Ser Glu Ile Ser Thr Phe Tyr Asn Arg Gln
            210                 215                 220
Val Glu Arg Ala Gly Asp Tyr Ser Asp His Cys Val Lys Trp Tyr Ser
225                 230                 235                 240
Thr Gly Leu Asn Asn Leu Arg Gly Thr Asn Ala Glu Ser Trp Val Arg
                245                 250                 255
Tyr Asn Gln Phe Arg Arg Asp Met Thr Leu Met Val Leu Asp Leu Val
                260                 265                 270
Ala Leu Phe Pro Ser Tyr Asp Thr Gln Met Tyr Pro Ile Lys Thr Thr
            275                 280                 285
Ala Gln Leu Thr Arg Glu Val Tyr Thr Asp Ala Ile Gly Thr Val His
            290                 295                 300
Pro His Pro Ser Phe Thr Ser Thr Trp Tyr Asn Asn Asn Ala Pro
305                 310                 315                 320
Ser Phe Ser Ala Ile Glu Ala Ala Val Val Arg Asn Pro His Leu Leu
                325                 330                 335
Asp Phe Leu Glu Gln Val Thr Ile Tyr Ser Leu Leu Ser Arg Trp Ser
                340                 345                 350
Asn Thr Gln Tyr Met Asn Met Trp Gly Gly His Lys Leu Glu Phe Arg
            355                 360                 365
Thr Ile Gly Gly Thr Leu Asn Ile Ser Thr Gln Gly Ser Thr Asn Thr
            370                 375                 380
Ser Ile Asn Pro Val Thr Leu Pro Phe Thr Ser Arg Asp Val Tyr Arg
385                 390                 395                 400
Thr Glu Ser Leu Ala Gly Leu Asn Leu Phe Leu Thr Gln Pro Val Asn
                405                 410                 415
Gly Val Pro Arg Val Asp Phe His Trp Lys Phe Val Thr His Pro Ile
                420                 425                 430
Ala Ser Asp Asn Phe Tyr Tyr Pro Gly Tyr Val Gly Ile Gly Thr Gln
            435                 440                 445
Leu Gln Asp Ser Glu Asn Glu Leu Pro Pro Glu Ala Thr Gly Gln Pro
            450                 455                 460
Asn Tyr Glu Ser Tyr Ser His Arg Leu Ser His Ile Gly Leu Ile Ser
465                 470                 475                 480
Ala Ser His Val Lys Ala Leu Val Tyr Ser Trp Thr His Arg Ser Ala
                485                 490                 495
Asp Arg Thr Asn Thr Ile Glu Pro Asn Ser Ile Thr Gln Ile Pro Leu
                500                 505                 510
Val Lys Ala Phe Asn Leu Ser Ser Gly Ala Ala Val Val Arg Gly Pro
            515                 520                 525
Gly Phe Thr Gly Gly Asp Ile Leu Arg Arg Thr Asn Thr Gly Thr Phe
            530                 535                 540
Gly Asp Ile Arg Val Asn Ile Asn Pro Pro Phe Ala Gln Arg Tyr Arg
545                 550                 555                 560
Val Arg Ile Arg Tyr Ala Ser Thr Thr Asp Leu Gln Phe His Thr Ser
                565                 570                 575
```

```
Ile Asn Gly Lys Ala Ile Asn Gln Gly Asn Phe Ser Ala Thr Met Asn
                580                 585                 590

Arg Gly Glu Asp Leu Asp Tyr Lys Thr Phe Arg Thr Val Gly Phe Thr
            595                 600                 605

Thr Pro Phe Ser Phe Leu Asp Val Gln Ser Thr Phe Thr Ile Gly Ala
        610                 615                 620

Trp Asn Phe Ser Ser Gly Asn Glu Val Tyr Ile Asp Arg Ile Glu Phe
625                 630                 635                 640

Val Pro Val Glu Val Thr Tyr Glu Ala Glu Tyr Asp Phe Glu Lys Ala
                645                 650                 655

Gln Glu Lys Val Thr Ala Leu Phe Thr Ser Thr Asn Pro Arg Gly Leu
            660                 665                 670

Lys Thr Asp Val Lys Asp Tyr His Ile Asp Gln Val Ser Asn Leu Val
        675                 680                 685

Glu Ser Leu Ser Asp Glu Phe Tyr Leu Asp Glu Lys Arg Glu Leu Phe
690                 695                 700

Glu Ile Val Lys Tyr Ala Lys Gln Leu His Ile Glu Arg Asn Met
705                 710                 715

<210> SEQ ID NO 22
<211> LENGTH: 719
<212> TYPE: PRT
<213> ORGANISM: Bacillus thuringiensis

<400> SEQUENCE: 22

Met Lys Leu Lys Asn G

-continued

```
Thr Gly Leu Asn Asn Leu Arg Gly Thr Asn Ala Glu Ser Trp Val Arg
                245                 250                 255

Tyr Asn Gln Phe Arg Arg Asp Met Thr Leu Met Val Leu Asp Leu Val
            260                 265                 270

Ala Leu Phe Pro Ser Tyr Asp Thr Gln Met Tyr Pro Ile Lys Thr Thr
        275                 280                 285

Ala Gln Leu Thr Arg Glu Val Tyr Thr Asp Ala Ile Gly Thr Val His
    290                 295                 300

Pro His Pro Ser Phe Thr Ser Thr Thr Trp Tyr Asn Asn Asn Ala Pro
305                 310                 315                 320

Ser Phe Ser Ala Ile Glu Ala Ala Val Val Arg Asn Pro His Leu Leu
                325                 330                 335

Asp Phe Leu Glu Gln Val Thr Ile Tyr Ser Leu Leu Ser Arg Trp Ser
            340                 345                 350

Asn Thr Gln Tyr Met Asn Met Trp Gly Gly His Lys Leu Glu Phe Arg
        355                 360                 365

Thr Ile Gly Gly Thr Leu Asn Ile Ser Thr Gln Gly Ser Thr Asn Thr
    370                 375                 380

Ser Ile Asn Pro Val Thr Leu Pro Phe Thr Ser Arg Asp Val Tyr Arg
385                 390                 395                 400

Thr Glu Ser Leu Ala Gly Leu Asn Leu Phe Leu Thr Gln Pro Val Asn
                405                 410                 415

Gly Val Pro Arg Val Asp Phe His Trp Lys Phe Val Thr His Pro Ile
            420                 425                 430

Ala Ser Asp Asn Phe Tyr Tyr Pro Gly Tyr Ala Gly Ile Gly Thr Gln
        435                 440                 445

Leu Gln Asp Ser Glu Asn Glu Leu Pro Pro Glu Ala Thr Gly Gln Pro
    450                 455                 460

Asn Tyr Glu Ser Tyr Ser His Arg Leu Ser His Ile Gly Leu Ile Ser
465                 470                 475                 480

Ala Ser His Val Lys Ala Leu Val Tyr Ser Trp Thr His Arg Ser Ala
                485                 490                 495

Asp Arg Thr Asn Thr Ile Glu Pro Asn Ser Ile Thr Gln Ile Pro Leu
            500                 505                 510

Val Lys Ala Phe Asn Leu Ser Ser Gly Ala Ala Val Val Arg Gly Pro
        515                 520                 525

Gly Phe Thr Gly Gly Asp Ile Leu Arg Arg Thr Asn Thr Gly Thr Phe
    530                 535                 540

Gly Asp Ile Arg Val Asn Ile Asn Pro Pro Phe Ala Gln Arg Tyr Arg
545                 550                 555                 560

Val Arg Ile Arg Tyr Ala Ser Thr Thr Asp Leu Gln Phe His Thr Ser
                565                 570                 575

Ile Asn Gly Lys Ala Ile Asn Gln Gly Asn Phe Ser Ala Thr Met Asn
            580                 585                 590

Arg Gly Glu Asp Leu Asp Tyr Lys Thr Phe Arg Thr Val Gly Phe Thr
        595                 600                 605

Thr Pro Phe Ser Phe Leu Asp Val Gln Ser Thr Phe Thr Ile Gly Ala
    610                 615                 620

Trp Asn Phe Ser Ser Gly Asn Glu Val Tyr Ile Asp Arg Ile Glu Phe
625                 630                 635                 640

Val Pro Val Glu Val Thr Tyr Glu Ala Glu Tyr Asp Phe Glu Lys Ala
                645                 650                 655

Gln Glu Lys Val Thr Ala Leu Phe Thr Ser Thr Asn Pro Arg Gly Leu
            660                 665                 670
```

```
Lys Thr Asp Val Lys Asp Tyr His Ile Asp Gln Val Ser Asn Leu Val
            675                 680                 685

Glu Ser Leu Ser Asp Glu Phe Tyr Leu Asp Lys Arg Glu Leu Phe
    690                 695                 700

Glu Ile Val Lys Tyr Ala Asn Glu Leu His Ile Glu Arg Asn Met
705                 710                 715

<210> SEQ ID NO 23
<211> LENGTH: 719
<212> TYPE: PRT
<213> ORGANISM: Bacillus thuringiensis

<400> SEQUENCE: 23

Met Lys Leu Lys Asn Pro Asp Lys His Gln Ser Phe Ser Ser Asn Ala
 1               5                  10                  15

Lys Val Asp L

Asp Phe Leu Glu Gln Val Thr Ile Tyr Ser Leu Leu Ser Arg Trp Ser
                340                 345                 350

Asn Thr Gln Tyr Met Asn Met Trp Gly Gly His Arg Leu Glu Phe Arg
            355                 360                 365

Thr Ile Gly Gly Met Leu Asn Thr Ser Thr Gln Gly Ser Thr Asn Thr
370                 375                 380

Ser Ile Asn Pro Val Thr Leu Pro Phe Thr Ser Arg Asp Val Tyr Arg
385                 390                 395                 400

Thr Glu Ser Leu Ala Gly Leu Asn Leu Phe Leu Thr Gln Pro Val Asn
                405                 410                 415

Gly Val Pro Arg Val Asp Phe His Trp Lys Phe Val Thr His Pro Ile
            420                 425                 430

Ala Ser Asp Asn Phe Tyr Tyr Pro Gly Tyr Ala Gly Ile Gly Thr Gln
        435                 440                 445

Leu Gln Asp Ser Glu Asn Glu Leu Pro Pro Glu Thr Thr Gly Gln Pro
    450                 455                 460

Asn Tyr Glu Ser Tyr Ser His Arg Leu Ser His Ile Gly Leu Ile Ser
465                 470                 475                 480

Ala Ser His Val Lys Ala Leu Val Tyr Ser Trp Thr His Arg Ser Ala
                485                 490                 495

Asp Arg Thr Asn Thr Ile Glu Pro Asn Ser Ile Thr Gln Ile Pro Leu
            500                 505                 510

Val Lys Ala Phe Asn Leu Ser Ser Gly Ala Ala Val Val Arg Gly Pro
        515                 520                 525

Gly Phe Thr Gly Gly Asp Ile Leu Arg Arg Thr Asn Thr Gly Thr Phe
    530                 535                 540

Gly Asp Ile Arg Val Asn Ile Asn Pro Pro Phe Ala Gln Arg Tyr Arg
545                 550                 555                 560

Val Arg Ile Arg Tyr Ala Ser Thr Thr Asp Ile Gln Phe His Thr Ser
                565                 570                 575

Ile Asn Gly Lys Ala Ile Asn Gln Gly Asn Phe Ser Ala Thr Met Asn
            580                 585                 590

Arg Gly Glu Asp Leu Asp Tyr Lys Thr Phe Arg Thr Val Gly Phe Thr
        595                 600                 605

Thr Pro Phe Ser Phe Ser Asp Val Gln Ser Thr Phe Thr Ile Gly Ala
    610                 615                 620

Trp Asn Phe Ser Ser Gly Asn Glu Val Tyr Ile Asp Arg Ile Glu Phe
625                 630                 635                 640

Val Pro Val Glu Val Thr Tyr Glu Ala Glu Tyr Asp Phe Glu Lys Ala
                645                 650                 655

Gln Glu Lys Val Thr Ala Leu Phe Thr Ser Thr Asn Pro Gly Gly Leu
            660                 665                 670

Lys Thr Asn Val Thr Glu Tyr His Ile Asp Gln Val Ser Asn Leu Val
        675                 680                 685

Glu Ser Leu Ser Asn Glu Phe Tyr Leu Asp Glu Lys Arg Glu Leu Phe
    690                 695                 700

Glu Ile Val Lys Tyr Ala Lys Gln Leu His Thr Gly Arg Asn Met
705                 710                 715

<210> SEQ ID NO 24
<211> LENGTH: 719
<212> TYPE: PRT
<213> ORGANISM: Bacillus thuringiensis

<400> SEQUENCE: 24

Met Lys Leu Lys Asn Gln Asp Lys His Gln Ser Phe Ser Ser Asn Ala
1               5                   10                  15

Lys Val Asp Lys Ile Ser Thr Asp Ser Leu Lys Asn Glu Thr Asp Ile
                20                  25                  30

Glu Leu Gln Asn Ile Asn His Glu Asp Cys Leu Lys Met Ser Glu Tyr
            35                  40                  45

Glu Asn Val Glu Pro Phe Val Ser Ala Ser Thr Ile Gln Thr Gly Ile
50                      55                  60

Gly Ile Ala Gly Lys Ile Leu Gly Thr Leu Gly Val Pro Phe Ala Gly
65                  70                  75                  80

Gln Val Ala Ser Leu Tyr Ser Phe Ile Leu Gly Glu Leu Trp Pro Lys
                85                  90                  95

Gly Lys Asn Gln Trp Glu Ile Phe Met Glu His Val Glu Ile Ile
            100                 105                 110

Asn Gln Lys Ile Ser Thr Tyr Ala Arg Asn Lys Ala Leu Thr Asp Leu
            115                 120                 125

Lys Gly Leu Gly Asp Ala Leu Ala Val Tyr His Asp Ser Leu Glu Ser
130                 135                 140

Trp Val Gly Asn Arg Asn Asn Thr Arg Ala Arg Ser Val Val Lys Ser
145                 150                 155                 160

Gln Tyr Ile Ala Leu Glu Leu Met Phe Val Gln Lys Leu Pro Ser Phe
                165                 170                 175

Ala Val Ser Gly Glu Glu Val Pro Leu Leu Pro Ile Tyr Ala Gln Ala
            180                 185                 190

Ala Asn Leu His Leu Leu Leu Arg Asp Ala Ser Ile Phe Gly Lys
            195                 200                 205

Glu Trp Gly Leu Ser Ser Glu Ile Ser Thr Phe Tyr Asn Arg Gln
    210                 215                 220

Val Glu Arg Ala Gly Asp Tyr Ser Asp His Cys Val Lys Trp Tyr Ser
225                 230                 235                 240

Thr Gly Leu Asn Asn Leu Arg Gly Thr Asn Ala Glu Ser Trp Val Arg
            245                 250                 255

Tyr Asn Gln Phe Arg Arg Asp Met Thr Leu Met Val Leu Asp Leu Val
            260                 265                 270

Ala Leu Phe Pro Ser Tyr Asp Thr Gln Met Tyr Pro Ile Lys Thr Thr
            275                 280                 285

Ala Gln Leu Thr Arg Glu Val Tyr Thr Asp Ala Ile Gly Thr Val His
            290                 295                 300

Pro His Pro Ser Phe Thr Ser Thr Thr Trp Tyr Asn Asn Asn Ala Pro
305                 310                 315                 320

Ser Phe Ser Ala Ile Glu Ala Ala Val Val Arg Asn Pro His Leu Leu
                325                 330                 335

Asp Phe Leu Glu Gln Val Thr Ile Tyr Ser Leu Leu Ser Arg Trp Ser
            340                 345                 350

Asn Thr Gln Tyr Met Asn Met Trp Gly Gly His Lys Leu Glu Phe Arg
            355                 360                 365

Thr Ile Gly Gly Thr Leu Asn Ile Ser Thr Gln Gly Ser Thr Asn Thr
370                 375                 380

Ser Ile Asn Pro Val Thr Leu Pro Phe Thr Ser Arg Asp Val Tyr Arg
385                 390                 395                 400

Thr Glu Ser Leu Ala Gly Leu Asn Leu Phe Leu Thr His Pro Val Asn
                405                 410                 415

Gly Val Pro Arg Val Asp Phe His Trp Lys Phe Val Thr His Pro Ile

```
                420             425             430
Ala Ser Asp Asn Phe Tyr Tyr Pro Gly Tyr Ala Gly Ile Gly Thr Gln
            435                 440             445
Leu Gln Asp Ser Glu Asn Glu Leu Pro Pro Glu Ala Thr Gly Gln Pro
        450                 455                 460
Asn Tyr Glu Ser Tyr Ser His Arg Leu Ser His Ile Gly Leu Ile Ser
465                 470                 475                 480
Ala Ser His Val Lys Ala Leu Val Tyr Ser Trp Thr His Arg Ser Ala
                485                 490                 495
Asp Arg Thr Asn Thr Ile Glu Pro Asn Ser Ile Thr Gln Ile Pro Leu
            500                 505                 510
Val Lys Ala Phe Asn Leu Ser Ser Gly Ala Ala Val Val Arg Gly Pro
        515                 520                 525
Gly Phe Thr Gly Gly Asp Ile Leu Arg Arg Thr Asn Thr Gly Thr Phe
        530                 535                 540
Gly Asp Ile Arg Val Asn Ile Asn Pro Pro Phe Ala Gln Arg Tyr Arg
545                 550                 555                 560
Val Arg Ile Arg Tyr Ala Ser Thr Thr Asp Leu Gln Phe His Thr Ser
                565                 570                 575
Ile Asn Gly Lys Ala Ile Asn Gln Gly Asn Phe Ser Ala Thr Met Asn
            580                 585                 590
Arg Gly Glu Asp Leu Asp Tyr Lys Thr Phe Arg Thr Val Gly Phe Thr
        595                 600                 605
Thr Pro Phe Ser Phe Leu Asp Val Gln Ser Thr Phe Thr Ile Gly Ala
        610                 615                 620
Trp Asn Phe Ser Ser Gly Asn Glu Val Tyr Ile Asp Arg Ile Glu Phe
625                 630                 635                 640
Val Pro Val Glu Val Thr Tyr Glu Ala Glu Tyr Asp Phe Glu Lys Ala
                645                 650                 655
Gln Glu Lys Val Thr Ala Leu Phe Thr Ser Thr Asn Pro Arg Gly Leu
            660                 665                 670
Lys Thr Asp Val Lys Asp Tyr His Ile Asp Gln Val Ser Asn Leu Val
        675                 680                 685
Glu Ser Leu Ser Asp Glu Phe Tyr Leu Asp Glu Lys Arg Glu Leu Phe
        690                 695                 700
Glu Ile Val Lys Tyr Ala Lys Gln Leu His Ile Glu Arg Asn Met
705                 710                 715

<210> SEQ ID NO 25
<211> LENGTH: 719
<212> TYPE: PRT
<213> ORGANISM: Bacillus thuringiensis serovar entomocidus

<400> SEQUENCE: 25

Met Lys Leu Lys Asn Pro Asp Lys His Gln Ser Leu Ser Ser Asn Ala
1               5                   10                  15
Lys Val Asp Lys Ile Ala Thr Asp Ser Leu Lys Asn Glu Thr Asp Ile
            20                  25                  30
Glu Leu Lys Asn Met Asn Asn Glu Asp Tyr Leu Arg Met Ser Glu His
        35                  40                  45
Glu Ser Ile Asp Pro Phe Val Ser Ala Ser Thr Ile Gln Thr Gly Ile
    50                  55                  60
Gly Ile Ala Gly Lys Ile Leu Gly Thr Leu Gly Val Pro Phe Ala Gly
65                  70                  75                  80
Gln Ile Ala Ser Leu Tyr Ser Phe Ile Leu Gly Glu Leu Trp Pro Lys
```

```
                        85                  90                  95
Gly Lys Ser Gln Trp Glu Ile Phe Met Glu His Val Glu Glu Ile Ile
                100                 105                 110

Asn Gln Lys Ile Leu Thr Tyr Ala Arg Asn Lys Ala Leu Ser Asp Leu
            115                 120                 125

Arg Gly Leu Gly Asp Ala Leu Ala Val Tyr His Glu Ser Leu Glu Ser
        130                 135                 140

Trp Val Glu Asn Arg Asn Asn Thr Arg Ala Arg Ser Val Val Lys Asn
145                 150                 155                 160

Gln Tyr Ile Ala Leu Glu Leu Met Phe Val Gln Lys Leu Pro Ser Phe
                165                 170                 175

Ala Val Ser Gly Glu Glu Val Pro Leu Leu Pro Ile Tyr Ala Gln Ala
            180                 185                 190

Ala Asn Leu His Leu Leu Leu Arg Asp Ala Ser Ile Phe Gly Lys
        195                 200                 205

Glu Trp Gly Leu Ser Ala Ser Glu Ile Ser Thr Phe Tyr Asn Arg Gln
            210                 215                 220

Val Glu Arg Thr Arg Asp Tyr Ser Asp His Cys Ile Lys Trp Tyr Asn
225                 230                 235                 240

Thr Gly Leu Asn Asn Leu Arg Gly Thr Asn Ala Lys Ser Trp Val Arg
                245                 250                 255

Tyr Asn Gln Phe Arg Lys Asp Met Thr Leu Met Val Leu Asp Leu Val
            260                 265                 270

Ala Leu Phe Pro Ser Tyr Asp Thr Leu Val Tyr Pro Ile Lys Thr Thr
        275                 280                 285

Ser Gln Leu Thr Arg Glu Val Tyr Thr Asp Ala Ile Gly Thr Val His
    290                 295                 300

Pro Asn Gln Ala Phe Ala Ser Thr Thr Trp Tyr Asn Asn Asn Ala Pro
305                 310                 315                 320

Ser Phe Ser Ala Ile Glu Ala Ala Val Ile Arg Ser Pro His Leu Leu
                325                 330                 335

Asp Phe Leu Glu Lys Val Thr Ile Tyr Ser Leu Leu Ser Arg Trp Ser
            340                 345                 350

Asn Thr Gln Tyr Met Asn Met Trp Gly Gly His Arg Leu Glu Ser Arg
        355                 360                 365

Pro Ile Gly Gly Ala Leu Asn Thr Ser Thr Gln Gly Ser Thr Asn Thr
    370                 375                 380

Ser Ile Asn Pro Val Thr Leu Gln Phe Thr Ser Arg Asp Val Tyr Arg
385                 390                 395                 400

Thr Glu Ser Leu Ala Gly Leu Asn Leu Phe Leu Thr Gln Pro Val Asn
                405                 410                 415

Gly Val Pro Arg Val Asp Phe His Trp Lys Phe Pro Thr Leu Pro Ile
            420                 425                 430

Ala Ser Asp Asn Phe Tyr Tyr Leu Gly Tyr Ala Gly Val Gly Thr Gln
        435                 440                 445

Leu Gln Asp Ser Glu Asn Glu Leu Pro Pro Glu Thr Thr Gly Gln Pro
    450                 455                 460

Asn Tyr Glu Ser Tyr Ser His Arg Leu Ser His Ile Gly Leu Ile Ser
465                 470                 475                 480

Ala Ser His Val Lys Ala Leu Val Tyr Ser Trp Thr His Arg Ser Ala
                485                 490                 495

Asp Arg Thr Asn Thr Ile Glu Pro Asn Ser Ile Thr Gln Ile Pro Leu
            500                 505                 510
```

```
Val Lys Ala Phe Asn Leu Ser Ser Gly Ala Ala Val Val Arg Gly Pro
        515                 520                 525

Gly Phe Thr Gly Gly Asp Ile Leu Arg Arg Thr Asn Thr Gly Thr Phe
    530                 535                 540

Gly Asp Ile Arg Val Asn Ile Asn Pro Pro Phe Ala Gln Arg Tyr Arg
545                 550                 555                 560

Val Arg Ile Arg Tyr Ala Ser Thr Thr Asp Leu Gln Phe His Thr Ser
            565                 570                 575

Ile Asn Gly Lys Ala Ile Asn Gln Gly Asn Phe Ser Ala Thr Met Asn
        580                 585                 590

Arg Gly Glu Asp Leu Asp Tyr Lys Thr Phe Arg Thr Ile Gly Phe Thr
    595                 600                 605

Thr Pro Phe Ser Phe Ser Asp Val Gln Ser Thr Phe Thr Ile Gly Ala
    610                 615                 620

Trp Asn Phe Ser Ser Gly Asn Glu Val Tyr Ile Asp Arg Ile Glu Phe
625                 630                 635                 640

Val Pro Val Glu Val Thr Tyr Glu Ala Glu Tyr Asp Phe Glu Lys Ala
            645                 650                 655

Gln Glu Lys Val Thr Ala Leu Phe Thr Ser Thr Asn Pro Arg Gly Leu
        660                 665                 670

Lys Thr Asp Val Lys Asp Tyr His Ile Asp Gln Val Ser Asn Leu Val
    675                 680                 685

Glu Ser Leu Ser Asp Glu Phe Tyr Leu Asp Glu Lys Arg Glu Leu Phe
    690                 695                 700

Glu Ile Val Lys Tyr Ala Lys Gln Ile His Ile Glu Arg Asn Met
705                 710                 715

<210> SEQ ID NO 26
<211> LENGTH: 719
<212> TYPE: PRT
<213> ORGANISM: Bacillus thuringiensis

<400> SEQUENCE: 26

Met Lys Leu Lys Asn Pro Asp Lys His Gln Ser Leu Ser Ser Asn Ala
1               5                   10                  15

Lys Val Asp Lys Ile Ala Thr Asp Ser Leu Lys Asn Glu Thr Asp Ile
            20                  25                  30

Glu Leu Lys Asn Met Asn Asn Glu Asp Tyr Leu Arg Met Ser Glu His
        35                  40                  45

Glu Ser Ile Asp Pro Phe Val Ser Ala Ser Thr Ile Gln Thr Gly Ile
    50                  55                  60

Gly Ile Ala Gly Lys Ile Leu Gly Thr Leu Gly Val Pro Phe Ala Gly
65                  70                  75                  80

Gln Ile Ala Ser Leu Tyr Ser Phe Ile Leu Gly Glu Leu Trp Pro Lys
                85                  90                  95

Gly Lys Ser Gln Trp Glu Ile Phe Met Glu His Val Glu Glu Ile Ile
            100                 105                 110

Asn Gln Lys Ile Leu Thr Tyr Ala Arg Asn Lys Ala Leu Ser Asp Leu
        115                 120                 125

Arg Gly Leu Gly Asp Ala Leu Ala Val Tyr His Glu Ser Leu Glu Ser
    130                 135                 140

Trp Val Glu Asn Arg Asn Asn Thr Arg Ala Arg Ser Val Val Lys Asn
145                 150                 155                 160

Gln Tyr Ile Ala Leu Glu Leu Met Phe Val Gln Lys Leu Pro Ser Phe
                165                 170                 175
```

```
Ala Val Ser Gly Glu Glu Val Pro Leu Leu Pro Ile Tyr Ala Gln Ala
            180                 185                 190

Ala Asn Leu His Leu Leu Leu Arg Asp Ala Ser Ile Phe Gly Lys
        195                 200                 205

Glu Trp Gly Leu Ser Ala Ser Glu Ile Ser Thr Phe Tyr Asn Arg Gln
    210                 215                 220

Val Glu Arg Thr Arg Asp Tyr Ser Asp His Cys Ile Lys Trp Tyr Asn
225                 230                 235                 240

Thr Gly Leu Asn Asn Leu Arg Gly Thr Asn Ala Lys Ser Trp Val Arg
                245                 250                 255

Tyr Asn Gln Phe Arg Lys Asp Met Thr Leu Met Val Leu Asp Leu Val
            260                 265                 270

Ala Leu Phe Pro Ser Tyr Asp Thr Leu Val Tyr Pro Ile Lys Thr Thr
        275                 280                 285

Ser Gln Leu Thr Arg Glu Val Tyr Thr Asp Ala Ile Gly Thr Val His
    290                 295                 300

Pro Asn Gln Ala Phe Ala Ser Thr Thr Trp Tyr Asn Asn Asn Ala Pro
305                 310                 315                 320

Ser Phe Ser Ala Ile Glu Ala Ala Val Ile Arg Ser Pro His Leu Leu
                325                 330                 335

Asp Phe Leu Glu Lys Val Thr Ile Tyr Ser Leu Leu Ser Arg Trp Ser
            340                 345                 350

Asn Thr Gln Tyr Met Asn Met Trp Gly Gly His Arg Leu Glu Ser Arg
        355                 360                 365

Pro Ile Gly Gly Ala Leu Asn Thr Ser Thr Gln Gly Ser Thr Asn Thr
    370                 375                 380

Ser Ile Asn Pro Val Thr Leu Gln Phe Thr Ser Arg Asp Val Tyr Arg
385                 390                 395                 400

Thr Glu Ser Leu Ala Gly Leu Asn Leu Phe Leu Thr Gln Pro Val Asn
                405                 410                 415

Gly Val Pro Arg Val Asp Phe His Trp Lys Phe Pro Thr Leu Pro Ile
            420                 425                 430

Ala Ser Asp Asn Phe Tyr Tyr Leu Gly Tyr Ala Gly Val Gly Thr Gln
        435                 440                 445

Leu Gln Asp Ser Glu Asn Glu Leu Pro Pro Glu Thr Thr Gly Gln Pro
    450                 455                 460

Asn Tyr Glu Ser Tyr Ser His Arg Leu Ser His Ile Gly Leu Ile Ser
465                 470                 475                 480

Ala Ser His Val Lys Ala Leu Val Tyr Ser Trp Thr His Arg Ser Ala
                485                 490                 495

Asp Arg Thr Asn Thr Ile Glu Pro Asn Ser Ile Thr Gln Ile Pro Leu
            500                 505                 510

Val Lys Ala Phe Asn Leu Ser Ser Gly Ala Ala Val Val Arg Gly Pro
        515                 520                 525

Gly Phe Thr Gly Gly Asp Ile Leu Arg Arg Thr Asn Thr Gly Thr Phe
    530                 535                 540

Gly Asp Ile Arg Val Asn Ile Asn Pro Pro Phe Ala Gln Arg Tyr Arg
545                 550                 555                 560

Val Arg Ile Arg Tyr Ala Ser Thr Thr Asp Leu Gln Phe His Thr Ser
                565                 570                 575

Ile Asn Gly Lys Ala Ile Asn Gln Gly Asn Phe Ser Ala Thr Met Asn
            580                 585                 590

Arg Gly Glu Asp Leu Asp Tyr Lys Thr Phe Arg Thr Ile Gly Phe Thr
        595                 600                 605
```

```
Thr Pro Phe Ser Phe Ser Asp Val Gln Ser Thr Phe Thr Ile Gly Ala
    610                 615                 620

Trp Asn Phe Ser Ser Gly Asn Glu Val Tyr Ile Asp Arg Ile Glu Phe
625                 630                 635                 640

Val Pro Val Glu Val Thr Tyr Glu Ala Glu Tyr Asp Phe Glu Lys Ala
                645                 650                 655

Gln Glu Lys Val Thr Ala Leu Phe Thr Ser Thr Asn Pro Arg Gly Leu
            660                 665                 670

Lys Thr Asp Val Lys Asp Tyr His Ile Asp Gln Val Ser Asn Leu Val
        675                 680                 685

Glu Ser Leu Ser Asp Glu Phe Tyr Leu Asp Glu Lys Arg Glu Leu Phe
    690                 695                 700

Glu Ile Val Lys Tyr Ala Lys Gln Ile His Ile Glu Arg Asn Met
705                 710                 715

<210> SEQ ID NO 27
<211> LENGTH: 719
<212> TYPE: PRT
<213> ORGANISM: Bacillus thuringiensis

<400> SEQUENCE: 27

Met Lys Leu Lys Asn Pro Asp Lys His Gln Thr Leu Ser Ser Asn Ala
1               5                   10                  15

Lys Val Asp Lys Ile Ala Thr Asp Ser Leu Lys Asn Glu Thr Asp Ile
            20                  25                  30

Glu Leu Lys Asn Met Asn Asn Glu Asp Tyr Leu Arg Met Ser Glu His
        35                  40                  45

Glu Ser Ile Asp Pro Phe Val Ser Ala Ser Thr Ile Gln Thr Gly Ile
    50                  55                  60

Gly Ile Ala Gly Lys Ile Leu Gly Thr Leu Gly Val Pro Phe Pro Gly
65                  70                  75                  80

Gln Ile Ala Ser Leu Tyr Ser Phe Ile Leu Gly Glu Leu Trp Pro Lys
                85                  90                  95

Gly Lys Ser Gln Trp Glu Ile Phe Met Glu His Val Glu Ala Ile Ile
            100                 105                 110

Asn Arg Lys Ile Ser Thr Tyr Ala Arg Asn Lys Ala Leu Thr Asp Leu
        115                 120                 125

Lys Gly Leu Gly Asp Ala Leu Ala Val Tyr His Glu Ser Leu Glu Ser
    130                 135                 140

Trp Val Gly Asn Arg Asn Asn Thr Arg Ala Arg Ser Val Val Lys Asn
145                 150                 155                 160

Gln Tyr Ile Ala Leu Glu Leu Met Phe Val Gln Lys Leu Pro Ser Phe
                165                 170                 175

Ala Val Ser Gly Glu Glu Val Pro Leu Leu Pro Ile Tyr Ala Gln Ala
            180                 185                 190

Ala Asn Leu His Leu Leu Leu Leu Arg Asp Ala Ser Ile Phe Glu Lys
        195                 200                 205

Asn Gly Gly Leu Ser Ala Ser Glu Ile Ser Thr Phe Tyr Asn Arg Gln
    210                 215                 220

Val Glu Arg Thr Arg Asp Tyr Ser Tyr His Cys Val Lys Trp Asn Asn
225                 230                 235                 240

Thr Gly Leu Asn Asn Leu Arg Ala Thr Asn Gly Gln Ser Trp Val Arg
                245                 250                 255

Tyr Asn Gln Phe Arg Lys Asp Ile Glu Leu Met Val Leu Asp Leu Val
            260                 265                 270
```

```
Arg Val Phe Pro Ser Tyr Asp Thr Leu Val Tyr Pro Ile Lys Thr Thr
            275                 280                 285

Ser Gln Leu Thr Arg Glu Val Tyr Thr Asp Ala Ile Gly Thr Val Asp
        290                 295                 300

Pro Asn Gln Ala Leu Arg Ser Thr Thr Trp Tyr Asn Asn Asn Ala Pro
305                 310                 315                 320

Ser Phe Ser Ala Ile Glu Ala Ala Val Ile Arg Ser Pro His Leu Leu
                325                 330                 335

Asp Phe Leu Glu Lys Val Thr Ile Tyr Ser Leu Leu Ser Arg Trp Ser
            340                 345                 350

Asn Thr Gln Tyr Met Asn Met Trp Gly Gly His Arg Leu Glu Ser Arg
        355                 360                 365

Pro Ile Gly Gly Ala Leu Asn Thr Ser Thr Gln Gly Ser Thr Asn Thr
    370                 375                 380

Ser Ile Asn Pro Val Thr Leu Gln Phe Thr Ser Arg Asp Phe Tyr Arg
385                 390                 395                 400

Thr Glu Ser Trp Ala Gly Leu Asn Leu Phe Leu Thr Gln Pro Val Asn
                405                 410                 415

Gly Val Pro Arg Val Asp Phe His Trp Lys Phe Pro Thr Leu Pro Ile
            420                 425                 430

Ala Ser Asp Asn Phe Tyr Tyr Leu Gly Tyr Ala Gly Val Gly Thr Gln
        435                 440                 445

Leu Gln Asp Ser Glu Asn Glu Leu Pro Pro Glu Thr Thr Gly Gln Pro
    450                 455                 460

Asn Tyr Glu Ser Tyr Ser His Arg Leu Ser His Ile Gly Leu Ile Ser
465                 470                 475                 480

Gly Ser His Val Lys Ala Leu Val Tyr Ser Trp Thr His Arg Ser Ala
                485                 490                 495

Asp Arg Thr Asn Thr Ile Glu Pro Asn Ser Ile Thr Gln Ile Pro Leu
            500                 505                 510

Val Lys Ala Phe Asn Leu Ser Ser Gly Ala Ala Val Val Arg Gly Pro
        515                 520                 525

Gly Phe Thr Gly Gly His Ile Leu Arg Arg Thr Lys Ser Gly Thr Phe
    530                 535                 540

Gly His Ile Arg Val Asn Ile Asn Pro Pro Phe Ala Gln Arg Tyr Arg
545                 550                 555                 560

Val Arg Met Ser Tyr Ala Ser Thr Thr Asp Leu Gln Phe His Thr Ser
                565                 570                 575

Ile Asn Gly Lys Ala Ile Asn Gln Gly Asn Phe Ser Ala Thr Met Asn
            580                 585                 590

Arg Gly Glu Asp Leu Asp Tyr Lys Thr Phe Arg Thr Val Gly Phe Thr
        595                 600                 605

Thr Pro Phe Ser Phe Ser Asp Val Gln Ser Thr Phe Thr Ile Gly Ala
    610                 615                 620

Trp Asn Phe Ser Ser Gly Asn Glu Val Tyr Ile Gly Arg Ile Glu Phe
625                 630                 635                 640

Val Pro Val Glu Val Thr Tyr Glu Ala Glu Tyr Asp Phe Glu Lys Ala
                645                 650                 655

Gln Glu Lys Val Thr Ala Leu Phe Thr Ser Thr Asn Pro Arg Gly Leu
            660                 665                 670

Lys Thr Asp Val Lys Asp Tyr His Ile Asp Gln Val Ser Asn Leu Val
        675                 680                 685

Glu Ser Leu Ser Asp Glu Leu Tyr Leu Asp Glu Lys Arg Glu Leu Phe
```

```
              690                 695                 700
Glu Ile Val Lys Tyr Ala Lys Gln Ile His Ile Glu Arg Asn Met
705                 710                 715

<210> SEQ ID NO 28
<211> LENGTH: 719
<212> TYPE: PRT
<213> ORGANISM: Bacillus thuringiensis

<400> SEQUENCE: 28

Met Lys Le

```
            355                 360                 365
Pro Ile Gly Gly Ala Leu Asn Thr Ser Thr Gln Gly Ser Thr Asn Thr
370                 375                 380

Ser Ile Asn Pro Val Thr Leu Gln Phe Thr Ser Arg Asp Phe Tyr Arg
385                 390                 395                 400

Thr Glu Ser Trp Ala Gly Leu Asn Leu Phe Leu Thr Gln Pro Val Asn
                405                 410                 415

Gly Val Pro Arg Val Asp Phe His Trp Lys Phe Pro Thr Leu Pro Ile
            420                 425                 430

Ala Ser Asp Asn Phe Tyr Tyr Leu Gly Tyr Ala Gly Val Gly Thr Gln
        435                 440                 445

Leu Gln Asp Ser Glu Asn Glu Leu Pro Pro Glu Thr Thr Gly Gln Pro
    450                 455                 460

Asn Tyr Glu Ser Tyr Ser His Arg Leu Ser His Ile Gly Leu Ile Ser
465                 470                 475                 480

Gly Ser His Val Lys Ala Leu Val Tyr Ser Trp Thr His Arg Ser Ala
                485                 490                 495

Asp Arg Thr Asn Thr Ile Glu Pro Asn Ser Ile Thr Gln Ile Pro Leu
            500                 505                 510

Val Lys Ala Phe Asn Leu Ser Ser Gly Ala Ala Val Val Arg Gly Pro
        515                 520                 525

Gly Phe Thr Gly Gly His Ile Leu Arg Arg Thr Lys Ser Gly Thr Phe
    530                 535                 540

Gly His Ile Arg Val Asn Ile Asn Pro Pro Phe Ala Gln Arg Tyr Arg
545                 550                 555                 560

Val Arg Met Ser Tyr Ala Ser Thr Thr Asp Leu Gln Phe His Thr Ser
                565                 570                 575

Ile Asn Gly Lys Ala Ile Asn Gln Gly Asn Phe Ser Ala Thr Met Asn
            580                 585                 590

Arg Gly Glu Asp Leu Asp Tyr Lys Thr Phe Arg Thr Val Gly Phe Thr
        595                 600                 605

Thr Pro Phe Ser Phe Ser Asp Val Gln Ser Thr Phe Thr Ile Gly Ala
    610                 615                 620

Trp Asn Phe Ser Ser Gly Asn Glu Val Tyr Ile Gly Arg Ile Glu Phe
625                 630                 635                 640

Val Pro Val Glu Val Thr Tyr Glu Ala Glu Tyr Asp Phe Glu Lys Ala
                645                 650                 655

Gln Glu Lys Val Thr Ala Leu Phe Thr Ser Thr Asn Pro Arg Gly Leu
            660                 665                 670

Lys Thr Asp Val Lys Asp Tyr His Ile Asp Gln Val Ser Asn Leu Val
        675                 680                 685

Glu Ser Leu Ser Asp Glu Leu Tyr Leu Asp Glu Lys Arg Glu Leu Phe
    690                 695                 700

Glu Ile Val Lys Tyr Ala Lys Gln Ile His Ile Glu Arg Asn Met
705                 710                 715

<210> SEQ ID NO 29
<211> LENGTH: 719
<212> TYPE: PRT
<213> ORGANISM: Unknown
<220> FEATURE:
<223> OTHER INFORMATION: Sequence 2 from patent US 6232439

<400> SEQUENCE: 29

Met Lys Leu Lys Asn Pro Asp Lys His Gln Thr Leu Ser Ser Asn Ala
1               5                   10                  15
```

```
Lys Val Asp Lys Ile Ala Thr Asp Ser Leu Lys Asn Glu Thr Asp Ile
                20                  25                  30

Glu Leu Lys Asn Met Asn Asn Glu Asp Tyr Leu Arg Met Ser Glu His
            35                  40                  45

Glu Ser Ile Asp Pro Phe Val Ser Ala Ser Thr Ile Gln Thr Gly Ile
 50                  55                  60

Gly Ile Ala Gly Lys Ile Leu Gly Thr Leu Gly Val Pro Phe Pro Gly
 65                  70                  75                  80

Gln Ile Ala Ser Leu Tyr Ser Phe Ile Leu Gly Glu Leu Trp Pro Lys
                85                  90                  95

Gly Lys Ser Gln Trp Glu Ile Phe Met Glu His Val Glu Ala Ile Ile
                100                 105                 110

Asn Arg Lys Ile Ser Thr Tyr Ala Arg Asn Lys Ala Leu Thr Asp Leu
                115                 120                 125

Lys Gly Leu Gly Asp Ala Leu Ala Val Tyr His Glu Ser Leu Glu Ser
130                 135                 140

Trp Val Gly Asn Arg Asn Asn Thr Arg Ala Arg Ser Val Val Lys Asn
145                 150                 155                 160

Gln Tyr Ile Ala Leu Glu Leu Met Phe Val Gln Lys Leu Pro Ser Phe
                165                 170                 175

Ala Val Ser Gly Glu Glu Val Pro Leu Leu Pro Ile Tyr Ala Gln Ala
                180                 185                 190

Ala Asn Leu His Leu Leu Leu Leu Arg Asp Ala Ser Ile Phe Glu Lys
                195                 200                 205

Asn Gly Gly Leu Ser Ala Ser Glu Ile Ser Thr Phe Tyr Asn Arg Gln
                210                 215                 220

Val Glu Arg Thr Arg Asp Tyr Ser Tyr His Cys Val Lys Trp Asn Asn
225                 230                 235                 240

Thr Gly Leu Asn Asn Leu Arg Ala Thr Asn Gly Gln Ser Trp Val Arg
                245                 250                 255

Tyr Asn Gln Phe Arg Lys Asp Ile Glu Leu Met Val Leu Asp Leu Val
                260                 265                 270

Arg Val Phe Pro Ser Tyr Asp Thr Leu Val Tyr Pro Ile Lys Thr Thr
                275                 280                 285

Ser Gln Leu Thr Arg Glu Val Tyr Thr Asp Ala Ile Gly Thr Val Asp
                290                 295                 300

Pro Asn Gln Ala Leu Arg Ser Thr Thr Trp Tyr Asn Asn Asn Ala Pro
305                 310                 315                 320

Ser Phe Ser Ala Ile Glu Ala Ala Val Ile Arg Ser Pro His Leu Leu
                325                 330                 335

Asp Phe Leu Glu Lys Val Thr Ile Tyr Ser Leu Leu Ser Arg Trp Ser
                340                 345                 350

Asn Thr Gln Tyr Met Asn Met Trp Gly Gly His Arg Leu Glu Ser Arg
                355                 360                 365

Pro Ile Gly Gly Ala Leu Asn Thr Ser Thr Gln Gly Ser Thr Asn Thr
                370                 375                 380

Ser Ile Asn Pro Val Thr Leu Gln Phe Thr Ser Arg Asp Phe Tyr Arg
385                 390                 395                 400

Thr Glu Ser Trp Ala Gly Leu Asn Leu Phe Leu Thr Gln Pro Val Ile
                405                 410                 415

Gly Val Pro Arg Val Asp Phe His Trp Lys Phe Pro Thr Leu Pro Ile
                420                 425                 430

Ala Ser Asp Asn Phe Tyr Tyr Leu Gly Tyr Ala Gly Val Gly Thr Gln
```

```
                435                440                445
Leu Gln Asp Ser Glu Asn Glu Leu Pro Pro Glu Thr Thr Gly Gln Pro
    450                455                460

Asn Tyr Glu Ser Tyr Ser His Arg Leu Ser His Ile Gly Leu Ile Ser
465                470                475                480

Ala Ser His Val Lys Ala Leu Val Tyr Ser Trp Thr His Arg Ser Ala
                485                490                495

Asp Arg Thr Asn Thr Ile Glu Pro Asn Ser Ile Thr Gln Ile Pro Leu
                500                505                510

Val Lys Ala Phe Asn Leu Ser Ser Gly Ala Ala Val Val Arg Gly Pro
    515                520                525

Gly Phe Thr Gly Gly His Ile Leu Arg Arg Thr Lys Ser Gly Thr Phe
    530                535                540

Gly His Ile Arg Val Asn Ile Asn Pro Pro Phe Ala Gln Arg Tyr Arg
545                550                555                560

Val Arg Met Ser Tyr Ala Ser Thr Thr Asp Leu Gln Phe His Thr Ser
                565                570                575

Ile Asn Gly Lys Ala Ile Asn Gln Gly Asn Phe Ser Ala Thr Met Asn
                580                585                590

Arg Gly Glu Asp Leu Asp Tyr Lys Thr Phe Arg Thr Val Gly Phe Thr
    595                600                605

Thr Pro Phe Ser Phe Ser Asp Val Gln Ser Thr Phe Thr Ile Gly Ala
    610                615                620

Trp Asn Phe Ser Ser Gly Asn Glu Val Tyr Ile Gly Arg Ile Glu Phe
625                630                635                640

Val Pro Val Glu Val Thr Tyr Glu Ala Glu Tyr Asp Phe Glu Lys Ala
                645                650                655

Gln Glu Lys Val Thr Ala Leu Phe Thr Ser Thr Asn Pro Arg Gly Leu
                660                665                670

Lys Thr Asp Val Lys Asp Tyr His Ile Asp Gln Val Ser Asn Leu Val
    675                680                685

Glu Ser Leu Ser Asp Glu Leu Tyr Leu Asp Lys Arg Glu Leu Phe
    690                695                700

Glu Ile Val Lys Tyr Ala Lys Gln Ile His Ile Glu Arg Asn Met
705                710                715

<210> SEQ ID NO 30
<211> LENGTH: 719
<212> TYPE: PRT
<213> ORGANISM: Bacillus thuringiensis

<400> SEQUENCE: 30

Met Lys Ser Lys Asn Gln Asn Met Tyr Arg Ser Phe Ser Ser Asn Ala
1               5

```
                100             105             110
Asn Gln Lys Ile Ser Thr Tyr Ala Arg Asn Lys Ala Leu Ala Asp Leu
            115                 120                 125

Lys Gly Leu Gly Asp Ala Leu Ala Val Tyr His Glu Ser Leu Glu Ser
130                 135                 140

Trp Ile Glu Asn Arg Asn Asn Thr Arg Val Arg Ser Val Val Lys Asn
145                 150                 155                 160

Gln Tyr Ile Ala Leu Glu Leu Met Phe Val Gln Lys Leu Pro Ser Phe
                165                 170                 175

Ala Val Ser Gly Glu Glu Val Pro Leu Leu Pro Ile Tyr Ala Gln Ala
            180                 185                 190

Ala Asn Leu His Leu Leu Leu Arg Asp Ala Ser Ile Phe Gly Lys
            195                 200                 205

Glu Trp Gly Leu Ser Glu Ser Glu Ile Ser Thr Phe Tyr Asn Arg Gln
        210                 215                 220

Ser Ser Gln Thr Gln Glu Tyr Ser Asp Tyr Cys Ser Glu Trp Tyr Asn
225                 230                 235                 240

Thr Gly Leu Asn Arg Leu Arg Gly Thr Asn Ala Glu Ser Trp Val Arg
                245                 250                 255

Tyr Asn Gln Phe Arg Arg Asp Met Thr Leu Met Val Leu Asp Leu Val
                260                 265                 270

Ala Leu Phe Pro Ser Tyr Asp Thr Arg Met Tyr Pro Ile Pro Thr Ser
            275                 280                 285

Ala Gln Leu Thr Arg Glu Val Tyr Thr Asp Ala Ile Gly Thr Val His
            290                 295                 300

Pro Asn Ala Ser Phe Ala Ser Thr Thr Trp Tyr Asn Asn Asn Ala Pro
305                 310                 315                 320

Ser Phe Ser Thr Ile Glu Ala Ala Val Val Arg Asn Pro His Leu Leu
                325                 330                 335

Asp Phe Leu Glu Gln Val Thr Ile Tyr Ser Leu Leu Ser Arg Trp Ser
                340                 345                 350

Asn Thr Gln Tyr Met Asn Met Trp Gly Gly His Lys Leu Glu Phe Arg
            355                 360                 365

Thr Ile Gly Gly Thr Leu Asn Thr Ser Thr Gln Gly Ser Thr Asn Thr
        370                 375                 380

Ser Ile Asn Pro Val Thr Leu Pro Phe Thr Ser Arg Asp Val Tyr Arg
385                 390                 395                 400

Thr Glu Ser Leu Ala Gly Leu Asn Leu Phe Leu Thr Gln Pro Val Asn
                405                 410                 415

Gly Val Pro Arg Val Asp Phe His Trp Lys Phe Val Thr His Pro Ile
            420                 425                 430

Ala Ser Asp Asn Phe Tyr Tyr Pro Gly Tyr Ala Gly Ile Gly Thr Gln
            435                 440                 445

Leu Gln Asp Ser Glu Asn Glu Leu Pro Pro Glu Thr Thr Gly Gln Pro
            450                 455                 460

Asn Tyr Glu Ser Tyr Ser His Arg Leu Ser His Ile Gly Leu Ile Ser
465                 470                 475                 480

Ala Ser His Val Lys Ala Leu Val Tyr Ser Trp Thr His Arg Ser Ala
                485                 490                 495

Asp Arg Thr Asn Thr Ile Asn Ser Asp Ser Ile Thr Gln Ile Pro Leu
            500                 505                 510

Val Lys Ala Phe Asn Leu Pro Ser Gly Ala Ser Val Val Arg Gly Pro
            515                 520                 525
```

```
Gly Phe Thr Gly Gly Asp Ile Leu Gln Arg Thr Asn Thr Gly Thr Phe
            530                 535                 540

Gly Asp Ile Arg Val Asn Ile Asn Pro Pro Phe Ala Gln Arg Tyr Arg
545                 550                 555                 560

Leu Arg Ile Arg Tyr Ala Ser Thr Thr Asn Leu Glu Phe His Thr Ser
                565                 570                 575

Ile Asn Gly Lys Ala Ile Asn Gln Gly Asn Phe Ser Ala Thr Met Asn
            580                 585                 590

Arg Gly Glu Asp Leu Asp Tyr Lys Ala Phe Arg Thr Val Gly Phe Thr
        595                 600                 605

Thr Pro Phe Ser Phe Ser Asn Ala Gln Ser Thr Phe Thr Ile Gly Ala
    610                 615                 620

Trp Asn Phe Ser Leu Gly Asn Glu Val Tyr Ile Asp Arg Ile Glu Phe
625                 630                 635                 640

Val Pro Val Glu Val Thr Tyr Glu Ala Glu Tyr Asp Leu Lys Lys Ala
                645                 650                 655

Gln Asp Glu Ile Thr Ala Met Phe Thr Ser Thr Asn Leu Arg Arg Leu
            660                 665                 670

Lys Thr Asn Val Thr Asp Cys His Ile Asp Gln Val Ser Asn Leu Val
            675                 680                 685

Glu Ser Leu Ser Asp Glu Phe Tyr Leu Asp Glu Lys Arg Glu Leu Phe
        690                 695                 700

Glu Ile Val Lys Tyr Ala Lys Gln Leu Asn Ile Glu Arg Asn Met
705                 710                 715

<210> SEQ ID NO 31
<211> LENGTH: 719
<212> TYPE: PRT
<213> ORGANISM: Bacillus thuringiensis

<400> SEQUENCE: 31

Met Lys Ser Lys Asn Gln Asn Met Tyr Arg Ser Phe Ser Asn Ala
  1               5                  10                  15

Thr Val Asp Lys Ser Phe Thr Asp Pro Leu Glu His Asn Thr Asn Met
            20                  25                  30

Glu Leu Gln Asn Ser Asn His Glu Asp Cys Leu Lys Met Ser Glu Tyr
        35                  40                  45

Glu Ser Val Glu Pro Phe Val Ser Val Ser Thr Ile Gln Thr Gly Ile
    50                  55                  60

Gly Ile Ala Gly Lys Ile Leu Gly Asn Leu Gly Val Pro Phe Ala Gly
65                  70                  75                  80

Gln Val Ala Ser Leu Tyr Ser Phe Ile Leu Gly Glu Leu Trp Pro Lys
                85                  90                  95

Gly Lys Ser Gln Trp Glu Ile Phe Met Glu His Val Glu Glu Leu Ile
            100                 105                 110

Asn Gln Lys Ile Ser Thr Tyr Ala Arg Asn Lys Ala Leu Ala Asp Leu
        115                 120                 125

Lys Gly Leu Gly Asp Ala Leu Ala Val Tyr His Glu Ser Leu Glu Ser
    130                 135                 140

Trp Ile Glu Asn Arg Asn Asn Thr Arg Val Arg Ser Val Val Lys Asn
145                 150                 155                 160

Gln Tyr Ile Ala Leu Glu Leu Met Phe Val Gln Lys Leu Pro Ser Phe
                165                 170                 175

Ala Val Ser Gly Glu Glu Val Pro Leu Leu Pro Ile Tyr Ala Gln Ala
            180                 185                 190
```

```
Ala Asn Leu His Leu Leu Leu Arg Asp Ala Ser Ile Phe Gly Lys
        195                 200                 205

Glu Trp Gly Leu Ser Glu Ser Glu Ile Ser Thr Phe Tyr Asn Arg Gln
210                 215                 220

Ser Ser Gln Thr Gln Glu Tyr Ser Asp Tyr Cys Ser Glu Trp Tyr Asn
225                 230                 235                 240

Thr Gly Leu Asn Arg Leu Arg Gly Thr Asn Ala Glu Ser Trp Val Arg
                245                 250                 255

Tyr Asn Gln Phe Arg Arg Asp Met Thr Leu Met Val Leu Asp Leu Val
            260                 265                 270

Ala Leu Phe Pro Ser Tyr Asp Thr Arg Met Tyr Pro Ile Pro Thr Ser
        275                 280                 285

Ala Gln Leu Thr Arg Glu Val Tyr Thr Asp Ala Ile Gly Thr Val His
    290                 295                 300

Pro Asn Ala Ser Phe Ala Ser Thr Thr Trp Tyr Asn Asn Ala Pro
305                 310                 315                 320

Ser Phe Ser Thr Ile Glu Ala Ala Val Val Arg Asn Pro His Leu Leu
                325                 330                 335

Asp Phe Leu Glu Gln Val Thr Ile Tyr Ser Leu Leu Ser Arg Trp Ser
            340                 345                 350

Asn Thr Gln Tyr Met Asn Met Trp Gly Gly His Lys Leu Glu Phe Arg
        355                 360                 365

Thr Ile Gly Gly Thr Leu Asn Thr Ser Thr Gln Gly Ser Thr Asn Thr
    370                 375                 380

Ser Ile Asn Pro Val Thr Leu Pro Phe Thr Ser Arg Asp Val Tyr Arg
385                 390                 395                 400

Thr Glu Ser Leu Ala Gly Leu Asn Leu Phe Leu Thr Gln Pro Val Asn
                405                 410                 415

Gly Val Pro Arg Val Asp Phe His Trp Lys Phe Val Thr His Pro Ile
            420                 425                 430

Ala Ser Asp Asn Phe Tyr Tyr Pro Gly Tyr Ala Gly Ile Gly Thr Gln
        435                 440                 445

Leu Gln Asp Ser Glu Asn Glu Leu Pro Pro Glu Thr Thr Gly Gln Pro
    450                 455                 460

Asn Tyr Glu Ser Tyr Ser His Arg Leu Ser His Ile Gly Leu Ile Ser
465                 470                 475                 480

Ala Ser His Val Lys Ala Leu Val Tyr Ser Trp Thr His Arg Ser Ala
                485                 490                 495

Asp Arg Thr Asn Thr Ile Asn Ser Asp Ser Ile Thr Gln Ile Pro Leu
            500                 505                 510

Val Lys Ala Phe Asn Leu Pro Ser Gly Ala Ser Val Val Arg Gly Pro
        515                 520                 525

Gly Phe Thr Gly Gly Asp Ile Leu Gln Arg Thr Asn Thr Gly Thr Phe
    530                 535                 540

Gly Asp Ile Arg Val Asn Ile Asn Pro Pro Phe Ala Gln Arg Tyr Arg
545                 550                 555                 560

Leu Arg Ile Arg Tyr Ala Ser Thr Thr Asn Leu Glu Phe His Thr Ser
                565                 570                 575

Ile Asn Gly Lys Ala Ile Asn Gln Gly Asn Phe Ser Ala Thr Met Asn
            580                 585                 590

Arg Gly Glu Asp Leu Asp Tyr Lys Ala Phe Arg Thr Val Gly Phe Thr
        595                 600                 605

Thr Pro Phe Ser Phe Ser Asn Ala Gln Ser Thr Phe Thr Ile Gly Ala
    610                 615                 620
```

-continued

```
Trp Asn Phe Ser Leu Gly Asn Glu Val Tyr Ile Asp Arg Ile Glu Phe
625                 630                 635                 640

Val Pro Val Glu Val Thr Tyr Glu Ala Glu Tyr Asp Leu Lys Lys Ala
                645                 650                 655

Gln Asp Glu Ile Thr Ala Met Phe Thr Ser Thr Asn Leu Arg Arg Leu
            660                 665                 670

Lys Thr Asn Val Thr Asp Cys His Ile Asp Gln Val Ser Asn Leu Val
        675                 680                 685

Glu Ser Leu Ser Asp Glu Phe Tyr Leu Asp Glu Lys Arg Glu Leu Phe
    690                 695                 700

Glu Ile Val Lys Tyr Ala Lys Gln Leu Asn Ile Glu Arg Asn Met
705                 710                 715
```